(12) United States Patent
Weeber et al.

(10) Patent No.: US 11,793,177 B2
(45) Date of Patent: Oct. 24, 2023

(54) ANIMAL MODEL OF ANGELMAN SYNDROME

(71) Applicants: UNIVERSITY OF SOUTH FLORIDA, Tampa, FL (US); THE REGENTS OF THE UNIVERSITY OF CALIFORNIA, Oakland, CA (US); THE TEXAS A&M UNIVERSITY SYSTEM, College Station, TX (US)

(72) Inventors: Edwin John Weeber, Apollo Beach, FL (US); David J. Segal, Davis, CA (US); Henriette O'Geen, Davis, CA (US); Benjamin Pyles, Davis, CA (US); Scott V. Dindot, College Station, TX (US)

(73) Assignees: UNIVERSITY OF SOUTH FLORIDA, Tampa, FL (US); THE REGENTS OF THE UNIVERSITY OF CALIFORNIA, Oakland, CA (US); THE TEXAS A&M UNIVERSITY SYSTEM, College Station, TX (US)

( * ) Notice: Subject to any disclaimer, the term of this patent is extended or adjusted under 35 U.S.C. 154(b) by 85 days.

(21) Appl. No.: 16/330,871

(22) PCT Filed: Oct. 3, 2017

(86) PCT No.: PCT/US2017/054992
§ 371 (c)(1),
(2) Date: Mar. 6, 2019

(87) PCT Pub. No.: WO2018/067608
PCT Pub. Date: Apr. 12, 2018

(65) Prior Publication Data
US 2019/0208752 A1    Jul. 11, 2019

Related U.S. Application Data

(60) Provisional application No. 62/403,463, filed on Oct. 3, 2016.

(51) Int. Cl.
*A01K 67/027* (2006.01)
*C12N 9/10* (2006.01)
*A61K 49/00* (2006.01)

(52) U.S. Cl.
CPC ........ *A01K 67/0276* (2013.01); *A01K 67/027* (2013.01); *A61K 49/0008* (2013.01); *C12N 9/104* (2013.01); *A01K 2217/054* (2013.01); *A01K 2227/105* (2013.01); *A01K 2267/0356* (2013.01)

(58) Field of Classification Search
CPC ................................................ A01K 67/0276
See application file for complete search history.

(56) References Cited

U.S. PATENT DOCUMENTS

2013/0058915 A1    3/2013   Greenberg et al.
2013/0317018 A1   11/2013   Philpot et al.
2016/0257957 A1    9/2016   Greenberg et al.

OTHER PUBLICATIONS

Jiang et al. (2010, PLoS One, vol. 5(8), pp. 1-14), (Year: 2010).*
Jiang et al. (1998, Neuron, vol. 21, pp. 799-811) (Year: 1998).*
Garcia-Arocena D. (2014, The Jackson Laboratory, Same Mutation, Different Phenotype?) (Year: 2014).*
Heimain-Patterson et al. (2011, Amyotrophic Lateral Schlerosis, vol. 00, pp. 1-8) (Year: 2011).*
Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2008, Theriogenology, vol. 69, pp. 1159-1164) (Year: 2008).*
Gomez et al. (2010, Theriogenology, vol. 74, pp. 498-515) (Year: 2010).*
Buta et al. (2013, Stem Cell Res., vol. 11, pp. 552-562) (Year: 2013).*
Tong et al. (2010, Nature, vol. 467(7312), pp. 211-213) (Year: 2010).*
Hong et al. (2012, Stem Cells and Development, vol. 21(9), pp. 1571-1586) (Year: 2012).*
Valente et al. (2013, Epilepsy Res., vol. 105, pp. 234-239). (Year: 2013).*
Judson et al. (2014, J. Comp. Neurol., vol. 522(8), pp. 1874-1896). (Year: 2014).*
Abbott A. (2004, Nature, vol. 428, pp. 464-466). (Year: 2004)*
Lasalle, J.M. et al. "Epigenetic regulation of UBE3A and roles in human neurodevelopmental disorders" *Epigenomics*, 2015, pp. 1213-1228, vol. 7, No. 7.
Bailus, B. J. et al. "Protein Delivery of an Artificial Transcription Factor Restores Widespread Ube3a Expression in an Angelman Syndrome Mouse Brain" *Mol. Ther.*, 2016, pp. 548-555, vol. 24, No. 3.
Yamasaki, K. et al. "Neurons but not glial cells show reciprocal imprinting of sense and antisense transcripts of Ube3a" *Hum. Mol. Genet.*, 2003, pp. 837-847, vol. 12, No. 8.
Leung, K. N. et al. "Imprinting regulates mammalian snoRNA-encoding chromatin decondensation and neuronal nucleolar size" *Hum. Mol. Genet.*, 2009, pp. 4227-4238, vol. 18, No. 22.
Buiting, K. et al. "Angelman syndrome—insights into a rare neurogenetic disorder" *Nat. Rev. Neurol.* 12, 2016, pp. 584-593, vol. 12.

(Continued)

*Primary Examiner* — Anoop K Singh
*Assistant Examiner* — David A Montanari
(74) *Attorney, Agent, or Firm* — QUARLES AND BRADY, LLP

(57) ABSTRACT

The present invention concerns non-human animals with cells having a genome that is lacking the entire E3 ubiquitin ligase (Ube3a) gene (including all isoforms and alternative promoters). These animals are useful for modeling Angelman Syndrome. The invention also includes methods for assessing the effect of an agent, such as potential therapeutics, on an animal model by exposing the animal or cells, tissues, or organs isolated therefrom, to an agent of interest.

10 Claims, 12 Drawing Sheets

Specification includes a Sequence Listing.

(56) References Cited

OTHER PUBLICATIONS

Winter, J. "MicroRNAs of the miR379-410 cluster: New players in embryonic neurogenesis and regulators of neuronal function" *Neurogenesis*, 2015, e1004970, vol. 2, No. 1.
Valdmanis, P. N et al. "Upregulation of the microRNA cluster at the Dlk1-Dio3 locus in lung adenocarcinoma" *Oncogene*, 2015, pp. 94-103, vol. 34, No. 1.
Stelzer, Y. et al. "The noncoding RNA IPW regulates the imprinted DLK1-DIO3 locus in an induced pluripotent stem cell model of Prader-Willi syndrome" *Nature Genetics*, 2014, pp. 551-557, vol. 46, No. 6.
Jones, K. A. et al. "Persistent neuronal Ube3a expression in the suprachiasmatic nucleus of Angelman syndrome model mice" *Sci. Rep.*, 2016, pp. 1-13, 6:28238.
Greer, P. L. et al. "The Angelman Syndrome Protein Ube3A Regulates Synapse Development by Ubiquitinating Arc" *Cell*, 2010, pp. 704-716, vol. 140, No. 5.
Filonova, I. et al. "Activity-dependent changes in MAPK activation in the Angelman Syndrome mouse model" *Learning & memory*, 2014, pp. 98-104, vol. 21.
Valluy, J. et al. "A coding-independent function of an alternative Ube3a transcript during neuronal development" *Nature Neuroscience*, 2015, pp. 666-676, Vo. 18, No. 5.
Jiang, Y. H. et al. "Mutation of the Angelman Ubiquitin Ligase in Mice Causes Increased Cytoplasmic p53 and Deficits of Contextual Learning and Long-Term Potentiation" *Neuron*, Oct. 1998, pp. 799-811, vol. 21.
Yashiro, K. et al. "Ube3a is required for experience-dependent maturation of the neocortex" *Nature Neuroscience*, 2009, pp. 777-783, vol. 12, No. 6.
Sun, J. et al. "UBE3A Regulates Synaptic Plasticity and Learning and Memory by Controlling SK2 Channel Endocytosis" *Cell Reports*, 2015, pp. 449-461, vol. 12, No. 3.
Godavarthi, S. K. et al. "Defective glucocorticoid hormone receptor signaling leads to increased stress and anxiety in a mouse model of Angelman syndrome" *Human Molecular Genetics*, 2012, pp. 1824-1834, vol. 21, No. 8.
Grier, M. D. et al. "Of mothers and myelin: Aberrant myelination phenotypes in mouse model of Angelman Syndrome are dependent on maternal and dietary influences" *Behav. Brain Res.*, 2015, pp. 260-267, vol. 291.
Wolyniec, K. et al. "The E6AP E3 ubiquitin ligase regulates the cellular response to oxidative stress" *Oncogene*, 2013, pp. 3510-3519, vol. 32.
Numata, K. et al. "Highly parallel SNP genotyping reveals high-resolution landscape of mono-allelic Ube3a expression associated with locus-wide antisense transcription" *Nucleic Acids Research*, 2011, pp. 2649-2657, vol. 39, No. 7.
Meng, L. et al. "Ube3a-ATS is an atypical RNA polymerase II transcript that represses the paternal expression of Ube3a" *Human Molecular Genetics*, 2012, pp. 3001-3012, vol. 21, No. 13.
Burette, A. C. et al. "The subcellular organization of UBE3A in neurons" *J Comp Neurol*, 2017, pp. 233-251, vol. 525, No. 2.
Powell, W. T. et al. "R-loop formation at Snord116 mediates topotecan inhibition of Ube3a-antisense and allele-specific chromatin decondensation" *Proceedings of the National Academy of Sciences of the United States of America*, 2013, pp. 13938-13943, vol. 110, No. 34.
Ciernia, A. V. et al. "Early motor phenotype detection in a female mouse model of Rett syndrome is improved by cross-fostering" *Human Molecular Genetics*, 2017, pp. 1839-1854, vol. 26, No. 10.
Matsuura, T. et al. "De novo truncating mutations in E6-AP ubiquitin-protein ligase gene (UBE3A) in Angelman syndrome" *Nat. Genet.*, 1997, pp. 74-77, vol. 15.
Kishino, T. et al. "UBE3A/E6-AP mutations cause Angelman syndrome" *Nat. Genet.*, 1997, pp. 70-73, vol. 15.

Gabriel, J. M. et al. "A transgene insertion creating a heritable chromosome deletion mouse model of Prader-Willi and Angelman syndromes" *Proc. Natl. Acad. Sci. USA*, Aug. 1999, pp. 9258-9263, vol. 96.
Albrecht, U. et al. "Imprinted expression of the murine Angelman syndrome gene, Ube3a, in hippocampal and Purkinje neurons" *Nature Genetics*, Sep. 1997, pp. 75-78, vol. 17.
Jana, N. "Understanding the Pathogenesis of Angelman Syndrome through Animal Models" *Neural Plasticity*, 2012, pp. 1-10.
Loon, L. H. et al. "Angelman Syndrome: Proteomics Analysis of an UBE3A Knockout Mouse and Its Implications" *Advanced Topics in Neurological Disorders*, 2012, pp. 159-184.
Kishino, T. et al. "Genomic Organization of the UBE3A/E6-AP Gene and Related Pseudogenes" *Genomics*, 1998, pp. 101-107, vol. 47, No. 1.
Fang, P. et al. "The spectrum of mutations in UBE3A causing Angelman syndrome" *Human Molecular Genetics*, 1999, pp. 129-135, vol. 8, No. 1.
Van Erp, P. et al. "The history and market impact of CRISPR RNA-guided nucleases" *Current Opinion in Virology*, 2015, pp. 85-90, vol. 12.
Maggio, I. et al. "Genome editing at the crossroads of delivery, specificity, and fidelity" *Trends in Biotechnology*, 2015, pp. 280-291, vol. 33, No. 5.
Rath, D. et al. "The CRISPR-Cas immune system: Biology, mechanisms and Applications" *Biochimie*, 2015, pp. 119-128, vol. 117.
Freedman, B. S. et al. "Modelling kidney disease with CRISPR-mutant kidney organoids derived from human pluripotent epiblast spheroids" *Nature Communications*, 2015, 6:8715(1-10).
Unniyampurath, U. et al. "RNA Interference in the Age of CRISPR: Will CRISPR Interfere with RNAi?" *International Journal of Molecular Sciences*, 2016, pp. 1-15, 17:291.
Boettcher, M. et al. "Choosing the Right Tool for the Job: RNAi, TALEN, or CRISPR" *Mol. Cell*, 2015, pp. 575-585, vol. 58, No. 4.
Carlson, D. F. et al. "Efficient TALEN-mediated Gene Knockout in Livestock" *PNAS*, Oct. 23, 2012, pp. 17382-17387, vol. 109, No. 43.
Heidenreich, M. et al. "Applications of CRISPR-Cas Systems in Neuroscience" *Nat. Rev. Neurosci.*, 2016, pp. 36-44, vol. 17, No. 1.
Jiang, Y. H. et al. "Altered Ultrasonic Vocalization and Impaired Learning and Memory in Angelman Syndrome Mouse Model with a Large Maternal Deletion from Ube3a to Gabrb3" *PLoS One*, Aug. 20, 2010, vol. 5, No. 8, e12278 (internal pp. 1-14) See p. 2; Abstract.
Meng, L. et al. "Truncation of Ube3a-ATS Unsilences Paternal Ube3a and Ameliorates Behavioral Defects in the Angelman Syndrome Mouse Model" *PLOS Genetics*, Dec. 26, 2013, vol. 9, No. 12, e1004039 (internal pp. 1-13) See pp. 2, 5 and 7; Abstract.
Godavarthi, S. K. et al. "Reversal of reduced parvalbumin neurons in hippocampus and amygdala of Angelman syndrome model mice by chronic treatment of fluoxetine" *Journal of Neurochemistry*, Apr. 25, 2014, pp. 444-454, vol. 130, No. 3.
Bird, L. M. "Angelman syndrome: review of clinical and molecular aspects" *The Application of Clinical Genetics*, 2014, pp. 93-104, vol. 7.
Tomaić, V. et al. "Angelman syndrome-associated ubiquitin ligase UBE3A/E6AP mutants interfere with the proteolytic activity of the proteasome" *Cell Death and Disease*, 2015, vol. 6, e1625.
Ding, F. et al. "Lack of Pwcr1/MBII-85 snoRNA is critical for neonatal lethality in Prader-Willi syndrome mouse models" *Mammalian Genome*, 2005, 16:424-431.
Kuroda, Y. et al. "Deletion of UBE3A in brothers with Angelman syndrome at the breakpoint with an inversion at 15q11.2" *Am. J. Med. Genet. Part A*, 2014, 164A:2873-2878.
Mabb, A. et al. "Angelman syndrome: insights into genomic imprinting and neurodevelopmental phenotypes" *Trends in Neurosci.*, 2011, 34(6):293-303.
Wang, L. et al. "Large genomic fragment deletion and functional gene cassette knock-in via Cas9 protein mediated genome editing in one-cell rodent embryos" *Scientific Reports*, 2015, 5:17517.

* cited by examiner

| WGBS | |
|---|---|
| GO Biological Process | |
| Term | *q*-value |
| Axon guidance | 4.68E-06 |
| Behavior | 2.86E-02 |
| Protein autophosphorylation | 1.53E-03 |
| GO Cellular Component | |
| Membrane raft | 1.32E-05 |
| Adherens junction | 4.76E-04 |
| Synapse part | 2.00E-03 |
| GO Molecular Function | |
| Protein serine/threonine kinase activity | 1.50E-03 |
| Receptor signaling protein activity | 4.74E-03 |
| Kinase binding | 1.48E-02 |

| RNA-seq | |
|---|---|
| GO Biological Process | |
| Term | *q*-value |
| Translation | 5.70E-08 |
| Protein localization to organelle | 2.23E-05 |
| Response to oxidative stress | 1.45E-02 |
| GO Cellular Component | |
| Mitochondrial membrane | 7.98E-08 |
| Focal adhesion | 6.94E-03 |
| Synapse part | 2.39E-02 |
| GO Molecular Function | |
| Structural constituent of ribosome | 6.71E-07 |
| Peptidase activator activity | 4.98E-02 |
| Oxidoreductase activity, acting on NAD(P)H | 4.98E-02 |

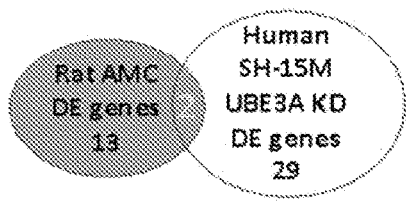
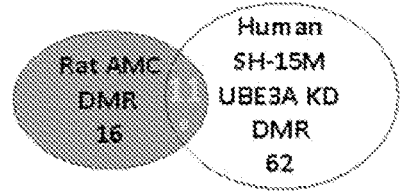
FIG. 8
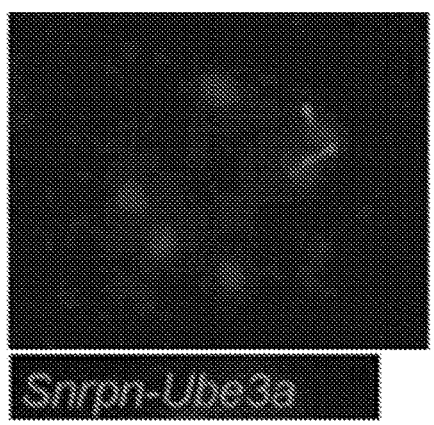
FIG. 9A　　　　　　　　　　　FIG. 9C
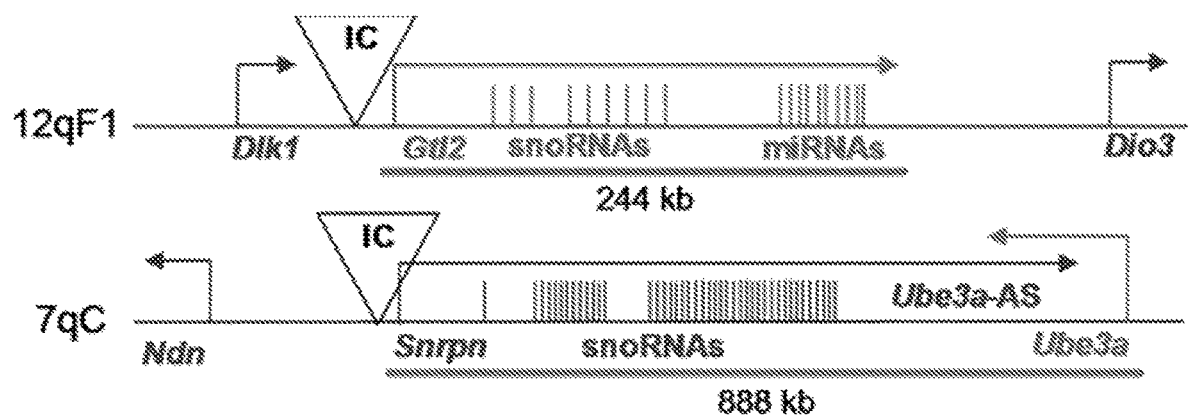
FIG. 9D

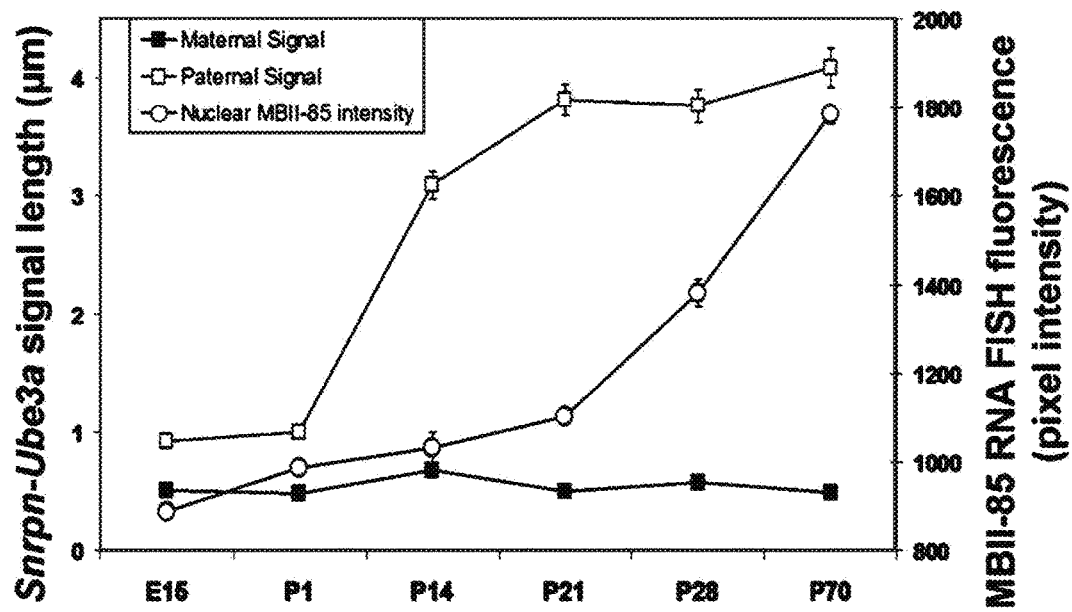
FIG. 9B
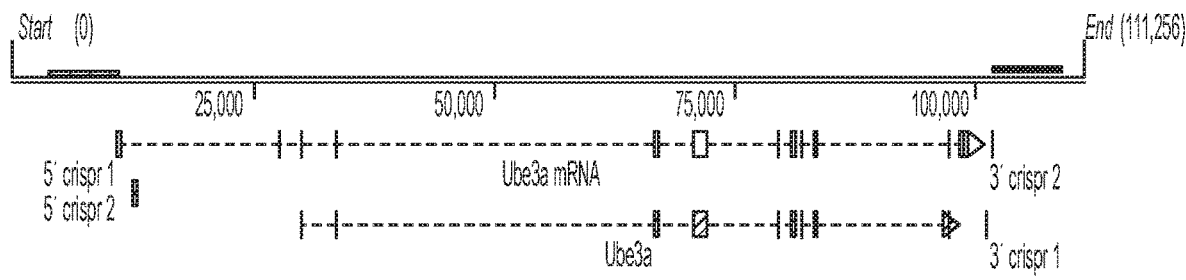
FIG. 10A
Founder 1: Del 90457bp/ins8bp
CCAAGAGCGAAGGCGAACTAGAGTAGGGCCCTGCAGAGAT---TAAATAAA----TCCCAGGCCCCCCAGAATT
*Founder 2: Del 90476bp/ins 1bp*
CCAAGAGCGAAGGCGAACTAGAGTAGGGCCCC---G---CAGAATTAAATAATTGATGATGATGATGATGATG
FIG. 10B

SEQUENCE LISTING

```
<160> NUMBER OF SEQ ID NOS: 26

<210> SEQ ID NO 1
<211> LENGTH: 875
<212> TYPE: PRT
<213> ORGANISM: Homo sapiens

<400> SEQUENCE: 1

Met Glu Lys Leu His Gln Cys Tyr Trp Lys Ser Gly Glu Pro Gln Ser
1               5                   10                  15

Asp Asp Ile Glu Ala Ser Arg Met Lys Arg Ala Ala Ala Lys His Leu
            20                  25                  30

Ile Glu Arg Tyr Tyr His Gln Leu Thr Glu Gly Cys Gly Asn Glu Ala
        35                  40                  45

Cys Thr Asn Glu Phe Cys Ala Ser Cys Pro Thr Phe Leu Arg Met Asp
    50                  55                  60

Asn Asn Ala Ala Ala Ile Lys Ala Leu Glu Leu Tyr Lys Ile Asn Ala
65                  70                  75                  80

Lys Leu Cys Asp Pro His Pro Ser Lys Lys Gly Ala Ser Ser Ala Tyr
                85                  90                  95

Leu Glu Asn Ser Lys Gly Ala Pro Asn Asn Ser Cys Ser Glu Ile Lys
            100                 105                 110

Met Asn Lys Lys Gly Ala Arg Ile Asp Phe Lys Asp Val Thr Tyr Leu
        115                 120                 125
```

```
Thr Glu Glu Lys Val Tyr Glu Ile Leu Glu Leu Cys Arg Glu Arg Glu
    130                 135                 140

Asp Tyr Ser Pro Leu Ile Arg Val Ile Gly Arg Val Phe Ser Ser Ala
145                 150                 155                 160

Glu Ala Leu Val Gln Ser Phe Arg Lys Val Lys Gln His Thr Lys Glu
                165                 170                 175

Glu Leu Lys Ser Leu Gln Ala Lys Asp Glu Asp Lys Asp Glu Asp Glu
            180                 185                 190

Lys Glu Lys Ala Ala Cys Ser Ala Ala Met Glu Glu Asp Ser Glu
        195                 200                 205

Ala Ser Ser Ser Arg Ile Gly Asp Ser Ser Gln Gly Asp Asn Leu
210                 215                 220

Gln Lys Leu Gly Pro Asp Asp Val Ser Val Asp Ile Asp Ala Ile Arg
225                 230                 235                 240

Arg Val Tyr Thr Arg Leu Leu Ser Asn Glu Lys Ile Glu Thr Ala Phe
                245                 250                 255

Leu Asn Ala Leu Val Tyr Leu Ser Pro Asn Val Glu Cys Asp Leu Thr
                260                 265                 270

Tyr His Asn Val Tyr Ser Arg Asp Pro Asn Tyr Leu Asn Leu Phe Ile
        275                 280                 285

Ile Val Met Glu Asn Arg Asn Leu His Ser Pro Glu Tyr Leu Glu Met
        290                 295                 300

Ala Leu Pro Leu Phe Cys Lys Ala Met Ser Lys Leu Pro Leu Ala Ala
305                 310                 315                 320

Gln Gly Lys Leu Ile Arg Leu Trp Ser Lys Tyr Asn Ala Asp Gln Ile
                325                 330                 335

Arg Arg Met Met Glu Thr Phe Gln Gln Leu Ile Thr Tyr Lys Val Ile
                340                 345                 350

Ser Asn Glu Phe Asn Ser Arg Asn Leu Val Asn Asp Asp Ala Ile
            355                 360                 365

Val Ala Ala Ser Lys Cys Leu Lys Met Val Tyr Tyr Ala Asn Val Val
370                 375                 380

Gly Gly Glu Val Asp Thr Asn His Asn Glu Glu Asp Asp Glu Glu Pro
385                 390                 395                 400

Ile Pro Glu Ser Ser Glu Leu Thr Leu Gln Glu Leu Leu Gly Glu Glu
                405                 410                 415

Arg Arg Asn Lys Lys Gly Pro Arg Val Asp Pro Leu Glu Thr Glu Leu
                420                 425                 430

Gly Val Lys Thr Leu Asp Cys Arg Lys Pro Leu Ile Pro Phe Glu Glu
            435                 440                 445

Phe Ile Asn Glu Pro Leu Asn Glu Val Leu Glu Met Asp Lys Asp Tyr
450                 455                 460

Thr Phe Phe Lys Val Glu Thr Glu Asn Lys Phe Ser Phe Met Thr Cys
465                 470                 475                 480

Pro Phe Ile Leu Asn Ala Val Thr Lys Asn Leu Gly Leu Tyr Tyr Asp
                485                 490                 495

Asn Arg Ile Arg Met Tyr Ser Glu Arg Arg Ile Thr Val Leu Tyr Ser
            500                 505                 510

Leu Val Gln Gly Gln Gln Leu Asn Pro Tyr Leu Arg Leu Lys Val Arg
                515                 520                 525

Arg Asp His Ile Ile Asp Asp Ala Leu Val Arg Leu Glu Met Ile Ala
530                 535                 540

Met Glu Asn Pro Ala Asp Leu Lys Lys Gln Leu Tyr Val Glu Phe Glu
```

```
                545                 550                 555                 560
        Gly Glu Gln Gly Val Asp Glu Gly Gly Val Ser Lys Glu Phe Phe Gln
                        565                 570                 575

Leu Val Val Glu Glu Ile Phe Asn Pro Asp Ile Gly Met Phe Thr Tyr
                        580                 585                 590

Asp Glu Ser Thr Lys Leu Phe Trp Phe Asn Pro Ser Ser Phe Glu Thr
                        595                 600                 605

Glu Gly Gln Phe Thr Leu Ile Gly Ile Val Leu Gly Leu Ala Ile Tyr
                        610                 615                 620

Asn Asn Cys Ile Leu Asp Val His Phe Pro Met Val Val Tyr Arg Lys
        625                 630                 635                 640

Leu Met Gly Lys Lys Gly Thr Phe Arg Asp Leu Gly Asp Ser His Pro
                        645                 650                 655

Val Leu Tyr Gln Ser Leu Lys Asp Leu Leu Glu Tyr Glu Gly Asn Val
                        660                 665                 670

Glu Asp Asp Met Met Ile Thr Phe Gln Ile Ser Gln Thr Asp Leu Phe
                        675                 680                 685

Gly Asn Pro Met Met Tyr Asp Leu Lys Glu Asn Gly Asp Lys Ile Pro
                        690                 695                 700

Ile Thr Asn Glu Asn Arg Lys Glu Phe Val Asn Leu Tyr Ser Asp Tyr
        705                 710                 715                 720

Ile Leu Asn Lys Ser Val Glu Lys Gln Phe Lys Ala Phe Arg Arg Gly
                        725                 730                 735

Phe His Met Val Thr Asn Glu Ser Pro Leu Lys Tyr Leu Phe Arg Pro
                        740                 745                 750

Glu Glu Ile Glu Leu Leu Ile Cys Gly Ser Arg Asn Leu Asp Phe Gln
                        755                 760                 765

Ala Leu Glu Glu Thr Thr Glu Tyr Asp Gly Gly Tyr Thr Arg Asp Ser
                        770                 775                 780

Val Leu Ile Arg Glu Phe Trp Glu Ile Val His Ser Phe Thr Asp Glu
        785                 790                 795                 800

Gln Lys Arg Leu Phe Leu Gln Phe Thr Thr Gly Thr Asp Arg Ala Pro
                        805                 810                 815

Val Gly Gly Leu Gly Lys Leu Lys Met Ile Ile Ala Lys Asn Gly Pro
                        820                 825                 830

Asp Thr Glu Arg Leu Pro Thr Ser His Thr Cys Phe Asn Val Leu Leu
                        835                 840                 845

Leu Pro Glu Tyr Ser Ser Lys Glu Lys Leu Lys Glu Arg Leu Leu Lys
        850                 855                 860

Ala Ile Thr Tyr Ala Lys Gly Phe Gly Met Leu
        865                 870                 875

<210> SEQ ID NO 2
<211> LENGTH: 4491
<212> TYPE: DNA
<213> ORGANISM: Homo sapiens

<400> SEQUENCE: 2
acagatcagg agaacctcag tctgacgaca ttgaagctag ccgaatgaag cgagcagctg     60
caaagcatct aatagaacgc tactaccacc agttaactga gggctgtgga aatgaagcct    120
gcacgaatga gttttgtgct tcctgtccaa cttttcttcg tatggataat aatgcagcag    180
ctattaaagc cctcgagctt tataagatta atgcaaaact ctgtgatcct catccctcca    240
agaaaggagc aagctcagct taccttgaga actcgaaagg tgcccccaac aactcctgct    300
```

```
ctgagataaa aatgaacaag aaaggcgcta gaattgattt taaagatgtg acttacttaa    360
cagaagagaa ggtatatgaa attcttgaat tatgtagaga aagagaggat tattcccctt    420
taatccgtgt tattggaaga gttttttcta gtgctgaggc attggtacag agcttccgga    480
aagttaaaca acacaccaag gaagaactga aatctcttca agcaaaagat gaagacaaag    540
atgaagatga aaaggaaaaa gctgcatgtt ctgctgctgc tatggaagaa gactcagaag    600
catcttcctc aaggataggt gatagctcac agggagacaa caatttgcaa aaattaggcc    660
ctgatgatgt gtctgtggat attgatgcca ttagaagggt ctacaccaga ttgctctcta    720
atgaaaaaat tgaaactgcc tttctcaatg cacttgtata tttgtcacct aacgtggaat    780
gtgacttgac gtatcacaat gtatactctc gagatcctaa ttatctgaat ttgttcatta    840
tcgtaatgga gaatagaaat ctccacagtc ctgaatatct ggaaatggct ttgccattat    900
tttgcaaagc gatgagcaag ctacccctttg cagcccaagg aaaactgatc agactgtggt    960
ctaaatacaa tgcagaccag attcggagaa tgatggagac atttcagcaa cttattactt    1020
ataaagtcat aagcaatgaa tttaacagtc gaaatctagt gaatgatgat gatgccattg    1080
ttgctgcttc gaagtgcttg aaaatggttt actatgcaaa tgtagtggga ggggaagtgg    1140
acacaaatca caatgaagaa gatgatgaag agcccatccc tgagtccagc gagctgacac    1200
ttcaggaact tttgggagaa gaagaagaa acaagaaagg tcctcgagtg gacccctgg    1260 aaactgaact tggtgttaaa accctggatt gtcgaaaacc acttatccct tttgaagagt    1320
ttattaatga accactgaat gaggttctag aaatggataa agattatact tttttcaaag    1380
tagaaacaga gaacaaattc tcttttatga catgtccctt tatattgaat gctgtcacaa    1440
agaatttggg attatattat gacaatagaa ttcgcatgta cagtgaacga gaatcactg    1500 ttctctacag cttagttcaa ggacagcagt tgaatccata tttgagactc aaagttagac    1560
gtgaccatat catagatgat gcacttgtcc ggctagagat gatcgctatg gaaaatcctg    1620
cagacttgaa gaagcagttg tatgtggaat ttgaaggaga acaaggagtt gatgagggag    1680
gtgtttccaa agaattttt cagctggttg tggaggaaat cttcaatcca gatattggta    1740
tgttcacata cgatgaatct acaaaattgt tttggtttaa tccatcttct tttgaaactg    1800
agggtcagtt tactctgatt ggcatagtac tgggtctggc tatttacaat aactgtatac    1860
tggatgtaca ttttcccatg gttgtctaca ggaagctaat ggggaaaaaa ggaacttttc    1920
gtgacttggg agactctcac ccagttctat atcagagttt aaaagattta ttggagtatg    1980
aagggaatgt ggaagatgac atgatgatca ctttccagat atcacagaca gatctttttg    2040
gtaacccaat gatgtatgat ctaaaggaaa atggtgataa aattccaatt acaaatgaaa    2100
acaggaagga atttgtcaat ctttattctg actacattct caataaatca gtagaaaaac    2160
agttcaaggc ttttcggaga ggttttcata tggtgaccaa tgaatctccc ttaaagtact    2220
tattcagacc agaagaaatt gaattgctta tatgtggaag ccggaatcta gatttccaag    2280
cactagaaga aactacagaa tatgacggtg gctataccag ggactctgtt ctgattaggg    2340
agttctggga aatcgttcat tcatttacag atgaacagaa aagactcttc ttgcagttta    2400
caacgggcac agacagagca cctgtgggag gactaggaaa attaaagatg attatagcca    2460
aaatggcccc agacacagaa aggttaccta catctcatac ttgctttaat gtgcttttac    2520
ttccggaata ctcaagcaaa gaaaaactta aagagagatt gttgaaggcc atcacgtatg    2580
ccaaaggatt tggcatgctg taaaacaaaa caaaacaaaa taaaacaaaa aaaaggaagg    2640
```

```
aaaaaaaaag aaaaaattta aaaaatttta aaaatataac gagggataaa ttttggtgg      2700 tgatagtgtc ccagtacaaa aaggctgtaa gatagtcaac cacagtagtc acctatgtct      2760
gtgcctccct tctttattgg ggacatgtgg gctggaacag cagatttcag ctacatatat      2820
gaacaaatcc tttattatta ttataattat tttttgcgt gaaagtgtta catattcttt       2880
cacttgtatg tacagagagg ttttctgaa tatttatttt aagggttaaa tcacttttgc       2940
ttgtgtttat tactgcttga ggttgagcct tttgagtatt taaaaaatat ataccaacag      3000
aactactctc ccaaggaaaa tattgccacc atttgtagac cacgtaacct tcaagtatgt     3060 gctactttt tgtccctgta tctaactcaa atcaggaact gtatttttt taatgatttg       3120 cttttgaaac ttgaagtctt gaaaacagtg tgatgcaatt actgctgttc tagcccccaa     3180
agagttttct gtgcaaaatc ttgagaatca atcaataaag aaagatggaa ggaagggaga    3240
aattggaatg ttttaactgc agccctcaga actttagtaa cagcacaaca aattaaaaac    3300
aaaaacaact catgccacag tatgtcgtct tcatgtgtct tgcaatgaac tgtttcagta     3360
gccaatcctc tttcttagta tatgaaagga cagggatttt tgttcttgtt gttctcgttg     3420
ttgttttaag tttactgggg aaagtgcatt tggccaaatg aaatggtagt caagcctatt    3480
gcaacaaagt taggaagttt gttgtttgtt tattataaac aaaaagcatg tgaaagtgca   3540
cttaagatag agttttatt aattacttac ttattaccta gatttaaat agacaatcca       3600 aagtctcccc ttcgtgttgc catcatcttg ttgaatcagc cattttatcg aggcacgtga    3660
tcagtgttgc aacataatga aaaagatggc tactgtgcct tgtgttactt aatcatacag    3720
taagctgacc tggaaatgaa tgaaactatt actcctaaga attacattgt atagccccac   3780
agattaaatt taattaatta attcaaaaca tgttaaacgt tactttcatg tactatggaa    3840
aagtacaagt aggtttacat tactgatttc cagaagtaag tagtttcccc tttcctagtc   3900
ttctgtgtat gtgatgttgt taatttcttt tattgcatta taaaataaaa ggattatgta   3960
tttttaacta aggtgagaca ttgatatatc cttttgctac aagctatagc taatgtgctg   4020
agcttgtgcc ttggtgattg attgattgat tgactgattg ttttaactga ttactgtaga   4080
tcaacctgat gatttgtttg tttgaaattg gcaggaaaaa tgcagctttc aaatcattgg   4140
ggggagaaaa aggatgtctt tcaggattat tttaattaat ttttttcata attgagacag   4200
aactgtttgt tatgtaccat aatgctaaat aaaaactgtgg cacttttcac cataatttaa  4260
tttagtggaa aaagaagaca atgctttcca tattgtgata aggtaacatg gggttttct    4320 gggccagcct ttagaacact gttagggtac atacgctacc ttgatgaaag ggaccttcgt   4380
gcaactgtag tcatcttaaa ggcttctcat ccactgtgct tcttaatgtg taattaaagt    4440
gaggagaaat taaatactct gagggcgttt tatataataa attcgtgaag a             4491
```

<210> SEQ ID NO 3
<211> LENGTH: 868
<212> TYPE: PRT
<213> ORGANISM: Rattus norvegicus

<400> SEQUENCE: 3

Met Ala Thr Ala Cys Lys Arg Ser Ser Gly Glu Ser Gln Ser Glu Asp
1               5                   10                  15

Ile Glu Ala Ser Arg Met Lys Arg Ala Ala Ala Lys His Leu Ile Glu
            20                  25                  30

Arg Tyr Tyr His Gln Leu Thr Glu Gly Cys Gly Asn Glu Ala Cys Thr
        35                  40                  45

-continued

```
Asn Glu Phe Cys Ala Ser Cys Pro Thr Phe Leu Arg Met Asp Asn Asn
 50                  55                  60

Ala Ala Ala Ile Lys Ala Leu Glu Leu Tyr Lys Ile Asn Ala Lys Leu
 65                  70                  75                  80

Cys Asp Pro His Pro Ser Lys Lys Gly Ala Ser Ser Ala Tyr Leu Glu
                 85                  90                  95

Asn Ser Lys Gly Ala Ser Asn Asn Ser Glu Ile Lys Met Asn Lys Lys
            100                 105                 110

Glu Glu Phe Lys Glu Val Asp Tyr Leu Thr Glu Lys Val Tyr Glu
            115                 120                 125

Ile Tyr Glu Phe Cys Arg Glu Arg Glu Asp Tyr Ser Pro Leu Ile Arg
130                 135                 140

Val Ile Gly Arg Ile Phe Ser Ser Ala Glu Ala Leu Val Gln Ser Phe
145                 150                 155                 160

Arg Lys Val Lys Gln His Thr Lys Glu Glu Leu Lys Ser Leu Gln Glu
                165                 170                 175

Lys Asp Glu Asp Lys Asp Glu Asp Glu Lys Glu Lys Ala Ala Cys Ser
            180                 185                 190

Ala Ala Ala Met Glu Glu Asp Ser Glu Ala Ser Ser Ser Arg Met Gly
            195                 200                 205

Asp Ser Ser Gln Gly Asp Asn Asn Val Gln Lys Leu Gly Pro Asp Asp
210                 215                 220

Val Thr Val Asp Ile Asp Ala Ile Arg Arg Val Tyr Ser Ser Leu Leu
225                 230                 235                 240

Ser Asp Glu Lys Ile Glu Thr Ala Phe Leu Asn Ala Leu Val Tyr Leu
                245                 250                 255

Ser Pro Asn Val Glu Cys Asp Leu Thr Tyr His Asn Val Tyr Thr Arg
            260                 265                 270

Asp Pro Asn Tyr Leu Asn Leu Phe Ile Ile Val Met Glu Asn Arg Asn
            275                 280                 285

Leu His Ser Pro Glu Tyr Leu Glu Met Ala Leu Pro Leu Phe Cys Lys
290                 295                 300

Ala Met Ser Lys Leu Pro Leu Ala Ala Gln Gly Lys Leu Ile Arg Leu
305                 310                 315                 320

Trp Ser Lys Tyr Ser Ala Asp Gln Ile Arg Arg Met Met Glu Thr Phe
                325                 330                 335

Gln Gln Leu Ile Thr Tyr Lys Val Ile Ser Asn Glu Phe Asn Ser Arg
            340                 345                 350

Asn Leu Val Asn Asp Asp Ala Ile Val Ala Ser Lys Cys Leu
            355                 360                 365

Lys Met Val Tyr Tyr Ala Asn Val Val Gly Gly Asp Val Asp Thr Asn
370                 375                 380

His Asn Glu Glu Asp Glu Glu Pro Ile Pro Glu Ser Ser Glu Leu
385                 390                 395                 400

Thr Leu Gln Glu Leu Leu Gly Glu Glu Arg Arg Asn Lys Lys Gly Pro
                405                 410                 415

Arg Val Asp Pro Leu Glu Thr Glu Ile Gly Val Lys Thr Leu Asp Cys
            420                 425                 430

Arg Lys Pro Leu Ile Ser Phe Glu Phe Ile Asn Glu Pro Leu Asn
            435                 440                 445

Asp Val Leu Glu Met Asp Lys Asp Tyr Thr Phe Phe Lys Val Glu Thr
450                 455                 460

Glu Asn Lys Phe Ser Phe Met Thr Cys Pro Phe Ile Leu Asn Ala Val
```

```
            465                 470                 475                 480
        Thr Lys Asn Leu Gly Leu Tyr Tyr Asp Asn Arg Ile Arg Met Tyr Ser
                        485                 490                 495

Glu Arg Arg Ile Thr Val Leu Tyr Ser Leu Val Gln Gly Gln Gln Leu
                        500                 505                 510

Asn Pro Tyr Leu Arg Leu Lys Val Arg Arg Asp His Ile Ile Asp Asp
                        515                 520                 525

Ala Leu Val Arg Leu Glu Met Ile Ala Met Glu Asn Pro Ala Asp Leu
                        530                 535                 540

Lys Lys Gln Leu Tyr Val Glu Phe Glu Gly Glu Gln Gly Val Asp Glu
        545                 550                 555                 560

Gly Gly Val Ser Lys Glu Phe Phe Gln Leu Val Val Glu Glu Ile Phe
                        565                 570                 575

Asn Pro Asp Ile Gly Met Phe Thr Tyr Asp Glu Ala Thr Arg Leu Phe
                        580                 585                 590

Trp Phe Asn Pro Ser Ser Phe Glu Thr Glu Gly Gln Phe Thr Leu Ile
                        595                 600                 605

Gly Ile Val Leu Gly Leu Ala Ile Tyr Asn Asn Cys Ile Leu Asp Val
                        610                 615                 620

His Phe Pro Met Val Val Tyr Arg Lys Leu Met Gly Lys Lys Gly Thr
        625                 630                 635                 640

Phe Cys Asp Leu Gly Asp Ser His Pro Ile Leu Tyr Gln Ser Leu Lys
                        645                 650                 655

Asp Leu Leu Glu Tyr Glu Gly Asn Val Glu Asp Asp Met Met Ile Thr
                        660                 665                 670

Phe Gln Ile Ser Gln Thr Asp Leu Phe Gly Asn Pro Met Met Tyr Asp
                        675                 680                 685

Leu Lys Glu Asn Gly Asp Lys Ile Pro Ile Thr Asn Glu Asn Arg Lys
                        690                 695                 700

Glu Phe Val Ser Leu Tyr Ser Asp Tyr Ile Leu Asn Lys Ser Val Glu
        705                 710                 715                 720

Lys Gln Phe Lys Ala Phe Arg Arg Gly Phe His Met Val Thr Asn Glu
                        725                 730                 735

Ser Pro Leu Lys Tyr Leu Phe Arg Pro Glu Glu Ile Glu Leu Leu Ile
                        740                 745                 750

Cys Gly Ser Arg Asn Leu Asp Phe Gln Ala Leu Glu Glu Thr Thr Glu
                        755                 760                 765

Tyr Asp Gly Gly Tyr Thr Arg Glu Ser Val Val Ile Arg Glu Phe Trp
        770                 775                 780

Glu Ile Val His Ser Phe Thr Asp Glu Gln Lys Arg Leu Phe Leu Gln
        785                 790                 795                 800

Phe Thr Thr Gly Thr Asp Arg Ala Pro Val Gly Gly Leu Gly Lys Leu
                        805                 810                 815

Lys Met Ile Ile Ala Lys Asn Gly Pro Asp Thr Glu Arg Leu Pro Thr
                        820                 825                 830

Ser His Thr Cys Phe Asn Val Leu Leu Leu Pro Glu Tyr Ser Ser Lys
                        835                 840                 845

Glu Lys Leu Lys Glu Arg Leu Leu Lys Ala Ile Thr Tyr Ala Lys Gly
        850                 855                 860

Phe Gly Met Leu
        865

<210> SEQ ID NO 4
```

<211> LENGTH: 5795
<212> TYPE: DNA
<213> ORGANISM: Rattus norvegicus

<400> SEQUENCE: 4

```
gtcgggatac tcggtccgcc cacctagtct tctcgtcctc gttcgcgaga tccgtgtttc    60
tcccaagatg gtggcgctcc tctttgggtg actacaggag acgacagggc ctttcgtctt   120
cgcaagtacc tcgccgcccc tcctgcgttc gctcgcgcac cgggccacgc agctgttcac   180
cgcctcatca cgactctcct cgttcgacca gtcgcggacg gtggcgcctc cttctgcttc   240
tcttcggagt tgctcgccac cctcgccccc caccgtggac agatcgcggc agcagccgtt   300
cagcgccgac ttcaaggttg cccaggcgcc cggcctcccg gcctcagttt cctgaggaga   360
agcgcgggtc ccgcatgaga cccggcggtg gcgccagcga agggaacga  ggcggtggcg   420
ggcggcggcg gtggacgagg gcgacaagga ccagtgaggc ggccgcagct gcgagggccg   480
cagcccacgc gcggggggcga ggacaggtta aaaatctgta agagcctgat tttagagttc   540
accagctcct cagaagtttg gcgaaatatg aattattaag cctacgttca gatcaagtta   600
gcagctagac tggtgtgaca acctgttttt aatcagtgac tcaaagctgt tatcaccctg   660
atgtcaccga atggccacag cttgtaaaag atcatcagga gaatcccagt ctgaggacat   720
tgaagctagc cgaatgaagc gagcagctgc aaagcatcta atagagcgct actaccatca   780
gttaactgag ggctgtggaa atgaggcctg cacgaatgag ttctgtgctt cctgtccaac   840
ttttcttcgt atggataaca atgcagcagc tattaaagct cttgagcttt ataaaattaa   900
tgcaaaactc tgtgatcctc atccctccaa gaaaggagca agctcagctt accttgagaa   960
ctcaaaaggt gcatctaaca actcagagat aaaaatgaac aagaaggaag agtttaaaga  1020
ggtggactac ctaactgaag agaaagtata tgaaatttat gaattttgta gggagagaga  1080
ggattactcc cctttaattc gtgtaattgg aagaatattt tctagtgctg aggcactggt  1140
tcagagcttt cggaaagtca acagcacac taaggaggaa ttgaaatctc ttcaagagaa  1200
ggatgaagac aaggatgaag atgaaaagga aaaagctgcg tgttctgctg ctgctatgga  1260
agaagactca gaagcatctt cttcaaggat gggtgatagc tcacagggag acaacaatgt  1320
acaaaaatta ggtcctgatg atgtgactgt ggatattgat gctataagaa gggtctacag  1380
cagtttgctc tctgatgaaa aaatagaaac tgccttcctg aatgcacttg tatatctgtc  1440
acctaacgtg gaatgtgatt tgacatatca taatgtgtac actcgagacc ctaattatct  1500
caatttgttc attattgtaa tggaaaatag aatctccac agtcctgaat atctggaaat  1560
ggcattgccg ttattttgca agctatgag taagctaccc cttgcagctc aaggaaaact  1620
gattaggctg tggtctaaat acagtgctga ccagattcgg agaatgatgg aaacatttca  1680
gcaacttatt acctacaaag tcataagcaa tgaatttaat agccgaaatc tagtgaatga  1740
tgatgatgcc attgttgctg cttcaaagtg tttgaaaatg gtttactatg caaatgtagt  1800
gggagggac gtggacacaa atcataatga ggaagatgat gaagagccta tacctgagtc  1860
cagtgaattg acacttcagg agcttctggg agaggaaaga agaaataaga aggtcctcg  1920
agtggatcca ctagaaaccg aaattggcgt taaaactcta gattgtcgaa accacttat  1980
ctccttgaa gaattcatta tgaaccact gaatgatgtt ctagaaatgg acaaagatta  2040
tacttttttc aaagttgaaa cagagaacaa attctctttt atgacatgtc cctttatatt  2100
gaatgctgtc acaaagaatc tgggattgta ttatgacaat agaattcgca tgtacagtga  2160
aagaagaatc actgttcttt acagcctagt tcaaggacag cagttgaatc catatttgag  2220
```

```
acttaaagtc agacgtgacc atattataga tgatgcactt gtccggctag agatgatcgc    2280
tatggaaaat cctgcagact tgaagaaaca gttgtatgtg gaatttgaag gagaacaagg    2340
agtagatgag ggaggcgttt ccaaagagtt ttttcagttg gttgtggagg aaatctttaa    2400
tccagatatt ggtatgttca catacgatga agctacaaga ttattttggt ttaatccatc    2460
ttcttttgaa actgagggtc aatttactct gattggcata gtcctgggtc tggctattta    2520
caataactgt atactggatg tccattttcc catggttgtg tacaggaagc taatggggaa    2580
aaaaggaacg ttttgtgact tgggagactc tcacccaatc ttatatcaga gtttaaagga    2640
tttattggaa tatgaaggga atgtggaaga tgatatgatg atcactttcc agatatcaca    2700
gacagatctt tttggtaacc caatgatgta tgatctaaaa gaaaatggtg ataaaattcc    2760
aattacaaat gaaaacagga aggaatttgt cagtctctat tcagactaca ttctcaataa    2820
atctgtagaa aaacaattca aggcatttcg cagaggtttt catatggtga ctaatgaatc    2880 accccttaaaa tacttattca gaccagaaga aattgaatta cttatatgtg gaagccggaa    2940
tctcgatttc caggcactag aagaaactac agagtatgat ggtggctata cgagagaatc    3000
tgttgtgatt ggggagttct gggaaattgt tcattcgttt acagatgaac agaaaagact    3060
tttcctgcag tttacaacag gcacagacag agcacctgtt ggaggactcg gaaaattgaa    3120
gatgattata gccaaaaatg gcccagacac agaaaggtta cctacatctc atacttgctt    3180
taatgtcctt ttacttccgg aatattcaag caaagaaaaa cttaaagaga gattgctgaa    3240
ggccatcaca tatgccaaag gatttggcat gctgtaaaca aaacaaaaac aaaaagaaaa    3300
aaagaaaaaa gtcaaaaaac ttaataaata taagagggat aatttgatgg taatagtgtc    3360
ccagttcaaa aaggctgtaa gatagtgaac cacagtactc atctatgtct gtgcctccct    3420
tcttcattgg ggacattgtg ggctggaaca gcagatttca gctgcatata tgaacaaatc    3480
ctttattatt attataatta ttttttttgcg tgaaagtgtt acatattctt tcacttgtat    3540
gtacagagag gttttctga atatttattt taagggttaa atcacttttg cttgtgttta    3600
ttactgcttg aggttgagcc ttttttgagta tttaaaatat atataccaac gaaactattc    3660
tcgcaaggaa aacattgcca ccatttgtag accatgtaat cttcaagtat gtgttttttt    3720
ttggccctgt atctaagtca aatcaggaac ttttttttaa ccatttgctt ttgaaacttg    3780
aagttaagga aacagtgtgg tgcaagtact gctgttctag cccccaagga gttttctgta    3840
caaaattttg agaatcaata aagatggaag ggagaatttg gaatgtttga accacagccc    3900
tcagaacttt agtaacagca caacaaatta aaacaactca tgccacagta cgttgtcttc    3960
atgtgtcttg caatgaactg tttcagtagc caatcctttt agtatatgaa aggacaggga    4020
tcttttttat tgttgttgtt gttgttgttg ttgttgttgt tgtttttgtt gtttaagttt    4080
actggggaaa gtgcatctgg ccaaatgata ggatagtcaa gcctattgca acaaaattag    4140
aaagtttgtt gtataaataa gcatgtaaaa gtgcacttaa aatgaatctt tattattccc    4200
gagattttaa atagacaatc caaagtctcc ccttctcttg ccatcatctt gtttaatcaa    4260 ctattttttca aggcactcga tcagtgttgc agcataatag aaagtccagc tactgtgcct    4320
tgtgttattt atttacacag taaacaggcc tggaaatgaa tggaactagt actcctgaga    4380
attaaattgt atatcctcca aattaaaatt tacttcaaaa gtgttaaaga attcatgtcc    4440
tatatataaa atacaaatag gcttagattg ctggacattt aatgtagttt cccatcccta    4500
gtcttttatg tttgtgatgt taatttcttt tgttgcataa caaaataaaa gaattatgta    4560
```

```
ttttttaacta aggagagaca tactggtata tcatttact  acaagctaca gatatcctgt    4620
tgagcttgtg ccttgattgt tttcacaact agtacaaatc aacctgatgt tttaaattgg    4680
cagggaataa ttaattgtag ctttcaaatc attggaaggg gaaaaggatg tcttttagga    4740
ttattttcct tcttgtagta gttgaggcag agctattatt tactgtaatg ctaaatgaaa    4800
cagtggctta aatactttaa tgggaaaaaa gaacacagtg cgttccatat tgtgataagg    4860
taatgtgagg tttttccttt tttttctgag ctagcccttta gaacactgtt gtggtatgta    4920
tgctaccttg attataggac cccctaaatg tgactatagt catcataatg ggcatctagt    4980
ccactgtgct tcttatgtat tatgaaagtg ataagaagac aaattaagtg ggtatatttt    5040
ataaaataaa ttcatgaaga gatttgtgtt cttcagttct caagtttatt atcactacag    5100
tattgaagta gttgtgatac tatatctgtg tgaaagttt  gaaatggtaa tatagattat    5160
caaacagaag taacatcagt atatttaaaa gaaagtgaaa acaaataaac ctaaaatgtt    5220
ttcagaggta aaaatacatt ctcacttgct tcctagtcag ttttcttgg catgttgcca    5280 cattattatg gctgccttt catcattgct tttctagatt gtcatggaac aatatttccg    5340
agttaaaaaa atacctcttg ctatagtaga acatttcaaa attacagcat aaaagcacag    5400
tctggagcaa aattttctg  gagacttggc agctgcagca aacaaattga gtgtctgtac    5460
atattgtggt ctataagtta attgtgtgat caaattcatt tgtaataacc ttacctttat    5520
ttggaagtac atccctgtgt aggaacgtat atatcaaaag aaacctataa atgagggttc    5580
agagaaccgg ttcatattga catgtggcac atgcatcact gggcagcatc actccctgtt    5640
tccataaggt ggctatgctg aaatcaacct cttaaagaat tattttctca agaatccata    5700
taacctagaa aaagaagtgt tttactgagg ctactctttc tgatgttcat cctttaactt    5760
cttatcccaa gacttattt  tatcctttct accct                              5795
```

<210> SEQ ID NO 5
<211> LENGTH: 872
<212> TYPE: PRT
<213> ORGANISM: Macaca mulatta

<400> SEQUENCE: 5

```
Met Ala Thr Ala Cys Lys Arg Ser Gly Glu Pro Gln Ser Asp Asp Ile
1               5                   10                  15

Glu Ala Ser Arg Met Lys Arg Ala Ala Ala Lys His Leu Ile Glu Arg
            20                  25                  30

Tyr Tyr His Gln Leu Thr Glu Gly Cys Gly Asn Glu Ala Cys Thr Asn
        35                  40                  45

Glu Phe Cys Ala Ser Cys Pro Thr Phe Leu Arg Met Asp Asn Asn Ala
    50                  55                  60

Ala Ala Ile Lys Ala Leu Glu Leu Tyr Lys Ile Asn Ala Lys Leu Cys
65                  70                  75                  80

Asp Pro His Pro Ser Lys Lys Gly Ala Ser Ser Ala Tyr Leu Glu Asn
                85                  90                  95

Ser Lys Gly Ala Pro Asn Asn Ser Cys Ser Glu Ile Lys Met Asn Lys
            100                 105                 110

Lys Gly Thr Arg Ile Asp Phe Lys Asp Val Thr Tyr Leu Thr Glu Glu
        115                 120                 125

Lys Val Tyr Glu Ile Leu Glu Leu Cys Arg Glu Arg Glu Asp Tyr Ser
    130                 135                 140

Pro Leu Ile Arg Val Ile Gly Arg Val Phe Ser Ser Ala Glu Ala Leu
145                 150                 155                 160
```

-continued

```
Val Gln Ser Phe Arg Lys Val Lys Gln His Thr Lys Glu Glu Leu Lys
                165                 170                 175

Ser Leu Gln Ala Lys Asp Glu Asp Lys Asp Glu Asp Lys Glu Lys
            180                 185                 190

Ala Ala Cys Ser Ala Ala Ala Met Glu Glu Asp Ser Glu Ala Ser Ser
            195                 200                 205

Ser Arg Ile Gly Asp Ser Ser Gln Gly Asp Asn Asn Leu Gln Lys Val
            210                 215                 220

Gly Pro Asp Asp Val Ser Val Asp Ile Asp Ala Ile Arg Arg Val Tyr
225                 230                 235                 240

Thr Arg Leu Leu Ser Asn Glu Lys Ile Glu Thr Ala Phe Leu Asn Ala
                245                 250                 255

Leu Val Tyr Leu Ser Pro Asn Val Glu Cys Asp Leu Thr Tyr His Asn
            260                 265                 270

Val Tyr Ser Arg Asp Pro Asn Tyr Leu Asn Leu Phe Ile Ile Val Met
            275                 280                 285

Glu Asn Arg Asn Leu His Ser Pro Glu Tyr Leu Glu Met Ala Leu Pro
    290                 295                 300

Leu Phe Cys Lys Ala Met Ser Lys Leu Pro Leu Ala Ala Gln Gly Lys
305                 310                 315                 320

Leu Ile Arg Leu Trp Ser Lys Tyr Asn Ala Asp Gln Ile Arg Arg Met
                325                 330                 335

Met Glu Thr Phe Gln Gln Leu Ile Thr Tyr Lys Val Ile Ser Asn Glu
            340                 345                 350

Phe Asn Ser Arg Asn Leu Val Asn Asp Asp Ala Ile Val Ala Ala
            355                 360                 365

Ser Lys Cys Leu Lys Met Val Tyr Tyr Ala Asn Val Val Gly Gly Glu
    370                 375                 380

Val Asp Thr Asn His Asn Glu Glu Asp Glu Glu Pro Ile Pro Glu
385                 390                 395                 400

Ser Ser Glu Leu Thr Leu Gln Glu Leu Leu Gly Glu Arg Arg Asn
                405                 410                 415

Lys Lys Gly Pro Arg Val Asp Pro Leu Glu Thr Glu Leu Gly Val Lys
            420                 425                 430

Thr Leu Asp Cys Arg Lys Pro Leu Ile Pro Phe Glu Glu Phe Ile Asn
            435                 440                 445

Glu Pro Leu Asn Glu Val Leu Glu Met Asp Lys Asp Tyr Thr Phe Phe
    450                 455                 460

Lys Val Glu Thr Glu Asn Lys Phe Ser Phe Met Thr Cys Pro Phe Ile
465                 470                 475                 480

Leu Asn Ala Val Thr Lys Asn Leu Gly Leu Tyr Tyr Asp Asn Arg Ile
                485                 490                 495

Arg Met Tyr Ser Glu Arg Arg Ile Thr Val Leu Tyr Ser Leu Val Gln
            500                 505                 510

Gly Gln Gln Leu Asn Pro Tyr Leu Arg Leu Lys Val Arg Arg Asp His
            515                 520                 525

Ile Ile Asp Asp Ala Leu Val Arg Leu Glu Met Ile Ala Met Glu Asn
    530                 535                 540

Pro Ala Asp Leu Lys Lys Gln Leu Tyr Val Glu Phe Glu Gly Glu Gln
545                 550                 555                 560

Gly Val Asp Glu Gly Gly Val Ser Lys Glu Phe Phe Gln Leu Val Val
                565                 570                 575
```

| | | | | | | | | | | | |
|---|---|---|---|---|---|---|---|---|---|---|---|
|Glu|Glu|Ile|Phe|Asn|Pro|Asp|Ile|Gly|Met|Phe|Thr|Tyr|Asp|Glu|Ser|
| | | |580| | | |585| | | |590| | | | |
|Thr|Lys|Leu|Phe|Trp|Phe|Asn|Pro|Ser|Ser|Phe|Glu|Thr|Glu|Gly|Gln|
| | |595| | | | |600| | | | |605| | | |
|Phe|Thr|Leu|Ile|Gly|Ile|Val|Leu|Gly|Leu|Ala|Ile|Tyr|Asn|Asn|Cys|
| |610| | | | |615| | | | |620| | | | |
|Ile|Leu|Asp|Val|His|Phe|Pro|Met|Val|Val|Tyr|Arg|Lys|Leu|Met|Gly|
|625| | | | |630| | | | |635| | | | |640|
|Lys|Lys|Gly|Thr|Phe|Arg|Asp|Leu|Gly|Asp|Ser|His|Pro|Val|Leu|Tyr|
| | | | |645| | | | |650| | | | |655| |
|Gln|Ser|Leu|Lys|Asp|Leu|Leu|Glu|Tyr|Glu|Gly|Asn|Val|Glu|Asp|Asp|
| | | |660| | | | |665| | | | |670| | |
|Met|Met|Ile|Thr|Phe|Gln|Ile|Ser|Gln|Thr|Asp|Leu|Phe|Gly|Asn|Pro|
| | |675| | | | |680| | | | |685| | | |
|Met|Met|Tyr|Asp|Leu|Lys|Glu|Asn|Gly|Asp|Lys|Ile|Pro|Ile|Thr|Asn|
| |690| | | | |695| | | | |700| | | | |
|Glu|Asn|Arg|Lys|Glu|Phe|Val|Asn|Leu|Tyr|Ser|Asp|Tyr|Ile|Leu|Asn|
|705| | | | |710| | | | |715| | | | |720|
|Lys|Ser|Val|Glu|Lys|Gln|Phe|Lys|Ala|Phe|Arg|Arg|Gly|Phe|His|Met|
| | | | |725| | | | |730| | | | |735| |
|Val|Thr|Asn|Glu|Ser|Pro|Leu|Lys|Tyr|Leu|Phe|Arg|Pro|Glu|Glu|Ile|
| | | |740| | | | |745| | | | |750| | |
|Glu|Leu|Leu|Ile|Cys|Gly|Ser|Arg|Asn|Leu|Asp|Phe|Gln|Ala|Leu|Glu|
| | |755| | | | |760| | | | |765| | | |
|Glu|Thr|Thr|Glu|Tyr|Asp|Gly|Gly|Tyr|Thr|Arg|Asp|Ser|Val|Leu|Ile|
| |770| | | | |775| | | | |780| | | | |
|Arg|Glu|Phe|Trp|Glu|Ile|Val|His|Ser|Phe|Thr|Asp|Glu|Gln|Lys|Arg|
|785| | | | |790| | | | |795| | | | |800|
|Leu|Phe|Leu|Gln|Phe|Thr|Thr|Gly|Thr|Asp|Arg|Ala|Pro|Val|Gly|Gly|
| | | | |805| | | | |810| | | | |815| |
|Leu|Gly|Lys|Leu|Lys|Met|Ile|Ile|Ala|Lys|Asn|Gly|Pro|Asp|Thr|Glu|
| | | |820| | | | |825| | | | |830| | |
|Arg|Leu|Pro|Thr|Ser|His|Thr|Cys|Phe|Asn|Val|Leu|Leu|Leu|Pro|Glu|
| | |835| | | | |840| | | | |845| | | |
|Tyr|Ser|Ser|Lys|Glu|Lys|Leu|Lys|Glu|Arg|Leu|Leu|Lys|Ala|Ile|Thr|
| |850| | | | |855| | | | |860| | | | |
|Tyr|Ala|Lys|Gly|Phe|Gly|Met|Leu| | | | | | | | |
|865| | | |870| | | | | | | | | | | |

<210> SEQ ID NO 6
<211> LENGTH: 2882
<212> TYPE: DNA
<213> ORGANISM: Macaca mulatta

<400> SEQUENCE: 6

```
gcggaggcgg cgggcgaggg cgacgacgac cagtgaggcg gccgccgcag cccaggcgcg     60
ggggcgacga caggttaaaa atctgtaaga gcctgatttt agaattcacc agctcctcag    120
aagtttggcg aaatatgagt tattaagcct acgctcagat caaggtagca gctagactgg    180
tgtgacaacc tgttttttaat cagtgactca aagctgtgat caccctgatg tcaccgaatg    240
gccacagctt gtaaaagatc aggagaacct cagtctgacg acattgaagc tagccgaatg    300
aagcgagcag ctgcaaagca tctaatagaa cgctactacc accagttaac tgagggctgt    360
ggaaatgaag cctgcacgaa tgagttttgt gcttcctgtc caacttttct tcgtatggat    420
```

| | |
|---|---|
| aataatgcag cagctattaa agccctcgag ctttataaga ttaatgcaaa actctgtgat | 480 |
| cctcatccct ccaagaaagg agcaagctca gcttaccttg agaactcgaa aggtgccccc | 540 |
| aacaactcct gctctgagat aaaaatgaac aagaaaggca ctagaattga ttttaaagat | 600 |
| gtgacttact taacagaaga gaaggtatat gaaattcttg aattatgtag agaaagagag | 660 |
| gattattccc ctttaattcg tgttattgga agagtttttt ctagtgctga ggcattggta | 720 |
| cagagcttcc ggaaagttaa acaacatacc aaggaagaac tgaaatctct tcaagcaaaa | 780 |
| gatgaagaca aggatgaaga tgaaaaggaa aaagctgcat gttctgctgc tgctatggaa | 840 |
| gaagactcag aagcatcttc ctcaaggata ggtgatagct cacagggaga caacaatttg | 900 |
| cagaaagtag gccctgatga tgtgtctgtg gatattgatg ccattagaag ggtctacacc | 960 |
| agattgctgt ctaatgaaaa aattgaaact gcctttctca atgcacttgt atatttgtca | 1020 |
| cctaacgtgg aatgtgactt gacgtatcac aatgtatact ctcgagatcc taattatctg | 1080 |
| aatttgttca ttatcgtaat ggagaataga atctccaca gtcctgaata tctggaaatg | 1140 |
| gctttgccat tattttgcaa agcaatgagc aagctacccc ttgcagccca aggaaaactg | 1200 |
| atcagactgt ggtctaaata caatgcagac cagattcgga gaatgatgga gacatttcag | 1260 |
| caacttatta cttacaaagt cataagcaat gaatttaaca gtcgaaatct agtgaacgat | 1320 |
| gatgatgcca ttgttgctgc ttcgaagtgc ttgaaaatgg tttactatgc aaatgtagtg | 1380 |
| ggaggggaag tggacacaaa tcacaatgaa gaagatgatg aagagcccat ccctgaatcc | 1440 |
| agtgagctga cacttcagga gcttttggga gaagaaagaa gaaacaagaa aggtcctcga | 1500 |
| gtggaccccc tggaaactga acttggtgtt aaaaccctgg attgtcgaaa accacttatc | 1560 |
| cctttttgaag agtttattaa tgaaccactg aatgaggttc tagaaatgga taagattat | 1620 |
| acttttttca aagtagaaac agagaacaaa ttctcttta tgacatgtcc ctttatatta | 1680 |
| aatgctgtca caagaatttt gggattatat tatgacaata gaattcgcat gtacagtgaa | 1740 |
| cgaagaatca ctgttctcta cagcttagtt caaggacagc agttgaatcc atattgaga | 1800 |
| ctcaaagtta gacgtgacca tatcatagat gatgcacttg tccggctaga gatgatcgct | 1860 |
| atggaaaatc ctgcagactt gaagaagcag ttgtatgtgg aatttgaagg agaacaagga | 1920 |
| gttgatgaag gagtgtttc caaagaattt tttcagctgg ttgtggagga atcttcaat | 1980 |
| ccagatattg gtatgttcac atacgatgaa tctacaaaat tgttttggtt taatccgtct | 2040 |
| tcttttgaaa ctgagggtca gtttactctg attggcatag tactgggtct ggctatttac | 2100 |
| aataactgta tactggatgt acattttccc atggttgtct acagaaagct aatggggaaa | 2160 |
| aaaggaactt ttcgtgactt gggagactct cacccagttc tgtatcagag tttaaaagat | 2220 |
| ttattggagt atgaagggaa tgtggaagac gacatgatga tcactttcca gatatcacag | 2280 |
| acagatcttt ttggtaaccc aatgatgtat gatctaaagg aaaatggtga taaaattcca | 2340 |
| attacaaatg aaaacaggaa ggaattgtc aatctttatt ctgactacat tctcaataaa | 2400 |
| tcagtagaaa aacagttcaa ggcttttcgg agaggttttc atatggtgac caatgaatct | 2460 |
| cccttaaagt acttattcag accagaagaa attgaattgc ttatatgtgg aagccggaat | 2520 |
| ctagatttcc aagcattaga agaaactaca gaatatgacg tggctatac cagggactct | 2580 |
| gttctgatta gggagttctg ggaaatcgtt cattcattta cagatgaaca gaaaagactc | 2640 |
| ttcttgcagt ttacaacggg cacagacaga gcacctgtgg gaggactagg aaaattaaag | 2700 |
| atgattatag ccaaaaatgg cccagacaca gaaaggttac ctacatctca tacttgcttt | 2760 |
| aatgtgcttt tacttccgga atattcaagc aaagaaaaac ttaaagagag attgttgaag | 2820 |

```
gccatcacgt atgccaaagg atttggcatg ctgtaaaaca aaacaaaata aaacaaaaaa    2880
aa                                                                  2882
```

<210> SEQ ID NO 7
<211> LENGTH: 856
<212> TYPE: PRT
<213> ORGANISM: Xenopus tropicalis

<400> SEQUENCE: 7

```
Met Lys Arg Ala Ala Lys His Leu Ile Glu Arg Tyr Tyr His Gln
1               5                   10                  15

Leu Thr Glu Gly Cys Gly Asn Glu Thr Cys Thr Asn Glu Phe Cys Ala
                20                  25                  30

Ser Cys Pro Thr Phe Leu Arg Met Asp Asn Asn Ala Ala Ala Ile Lys
            35                  40                  45

Ala Leu Glu Leu Tyr Lys Val Asn Ala Lys Leu Cys Asp Pro His Pro
        50                  55                  60

Ser Lys Lys Gly Thr Ser Ser Tyr Leu Glu Asn Asn Ser Lys Ser
65                  70                  75                  80

Ala His Asn Asn Ser Cys Thr Glu Arg Lys Met Asn Lys Lys Asp Leu
                85                  90                  95

His Gly Pro Arg Asp Asp Phe Lys Asp Val Thr Phe Leu Ser Glu Glu
            100                 105                 110

Lys Val Tyr Glu Ile Leu Glu Leu Cys Arg Glu Lys Glu Asp Tyr Ser
        115                 120                 125

Pro Leu Ile Arg Val Ile Gly Arg Val Phe Ser Ser Ala Glu Ala Leu
    130                 135                 140

Val Gln Ser Phe Arg Lys Ala Lys His His Thr Lys Glu Glu Leu Lys
145                 150                 155                 160

Ser Leu Gln Glu Lys Asp Glu Asp Lys Asp Glu Asp Glu Lys Glu Lys
                165                 170                 175

Ala Ala Ser Ser Ala Ala Ala Met Glu Glu Asp Ser Gly Ala Ser Ser
            180                 185                 190

Ser Arg Leu Ser Asp Asn Ser Gln Gly Asp Asn Asn Ile Gln Lys Leu
        195                 200                 205

Gly Pro Glu Glu Val Ser Leu Asp Ile Glu Ala Val Arg Arg Val Tyr
    210                 215                 220

His Arg Leu Leu Ser Asn Glu Lys Ile Glu Thr Ala Phe Leu Asn Ala
225                 230                 235                 240

Leu Val Tyr Leu Ser Pro Asn Val Glu Cys Asp Leu Thr Tyr His Asn
                245                 250                 255

Val Tyr Ser Arg Asp Pro Asn Tyr Leu Asn Leu Phe Ile Ile Val Met
            260                 265                 270

Glu Asn Gly Asn Leu His Ser Pro Glu Tyr Leu Glu Met Ala Leu Pro
        275                 280                 285

Leu Phe Cys Lys Ala Met Ser Lys Leu Pro Leu Ala Ala Gln Ala Lys
    290                 295                 300

Leu Ile Arg Leu Trp Ser Lys Tyr Ser Ala Glu Gln Ile Arg Arg Met
305                 310                 315                 320

Met Glu Thr Phe Gln Gln Leu Ile Thr Tyr Lys Val Ile Ser Asn Glu
                325                 330                 335

Phe Asn Ser Arg Asn Leu Val Asn Asp Asp Ala Ile Val Ala Ala
            340                 345                 350
```

-continued

```
Thr Lys Cys Leu Lys Met Val Tyr Tyr Ser Asn Val Gly Gly Glu
            355                 360                 365
Ile Glu Thr Asp His Asn Glu Glu Asp Glu Pro Val Pro Glu
370                 375                 380
Ser Ser Glu Leu Thr Leu Gln Glu Leu Leu Gly Glu Glu Arg Arg Asn
385                 390                 395                 400
Lys Lys Gly Pro Arg Val Asp Pro Leu Glu Thr Glu Leu Gly Val Lys
                405                 410                 415
Ser Ile Asp Cys Arg Lys Pro Leu Ile Pro Phe Glu Glu Phe Val Asn
            420                 425                 430
Glu Pro Leu Asn Asp Val Leu Glu Met Asp Lys Asp Tyr Thr Phe Phe
            435                 440                 445
Lys Val Glu Thr Glu Asn Lys Phe Ser Phe Met Thr Cys Pro Phe Ile
450                 455                 460
Leu Asn Ala Val Thr Lys Asn Leu Gly Leu Tyr Tyr Asp Asn Arg Ile
465                 470                 475                 480
Arg Met Tyr Ser Glu Arg Arg Ile Thr Val Leu Tyr Ser Leu Val Gln
                485                 490                 495
Gly Gln Gln Leu Asn Pro Tyr Leu Arg Leu Lys Val Arg Arg Asp His
            500                 505                 510
Ile Ile Asp Asp Ala Leu Val Arg Leu Glu Met Ile Ala Met Glu Asn
        515                 520                 525
Pro Ala Asp Leu Lys Lys Gln Leu Tyr Val Glu Phe Glu Gly Glu Gln
            530                 535                 540
Gly Val Asp Glu Gly Gly Val Ser Lys Glu Phe Phe Gln Leu Val Val
545                 550                 555                 560
Glu Glu Ile Phe Asn Pro Asp Ile Gly Met Phe Thr Tyr Asp Glu Ser
                565                 570                 575
Thr Lys His Ser Trp Phe Asn Pro Ser Ser Phe Glu Thr Glu Gly Gln
            580                 585                 590
Phe Thr Leu Ile Gly Ile Val Leu Gly Leu Ala Ile Tyr Asn Asn Cys
            595                 600                 605
Ile Leu Asp Val His Phe Pro Met Val Val Tyr Arg Lys Leu Met Gly
610                 615                 620
Lys Lys Gly Thr Phe Arg Asp Leu Ala Asp Ser His Pro Val Leu Tyr
625                 630                 635                 640
Gln Ser Leu Lys Glu Leu Leu Glu Tyr Glu Gly Asn Val Glu Glu Asp
                645                 650                 655
Met Met Met Thr Phe Gln Ile Ser Gln Thr Asp Leu Phe Gly Asn Pro
            660                 665                 670
Leu Met His Asp Leu Lys Glu Asn Gly Asp Lys Ile Pro Ile Thr Asn
            675                 680                 685
Glu Asn Arg Lys Glu Phe Val Ser Leu Tyr Thr Asp Tyr Ile Leu Asn
690                 695                 700
Lys Ser Val Glu Lys Gln Phe Lys Ala Phe Arg Arg Gly Phe His Met
705                 710                 715                 720
Val Thr Asn Glu Ser Pro Leu Lys Tyr Leu Phe Arg Pro Glu Glu Ile
                725                 730                 735
Glu Leu Leu Ile Cys Gly Ser Arg Asn Leu Asp Phe Gln Ala Leu Lys
            740                 745                 750
Asp Thr Thr Glu Tyr Asp Gly Gly Tyr Thr Arg Asp Ser Asn Ile Ile
            755                 760                 765
Lys Glu Phe Trp Glu Ile Val Asn Ser Phe Thr Glu Glu Gln Lys Arg
```

|     |     |     |     | 770 |     |     |     | 775 |     |     |     | 780 |     |     |
| --- | --- | --- | --- | --- | --- | --- | --- | --- | --- | --- | --- | --- | --- | --- |
| Leu | Phe | Leu | Gln | Phe | Thr | Thr | Gly | Thr | Asp | Arg | Ala | Pro | Val | Gly | Gly |
| 785 |     |     |     |     | 790 |     |     |     |     | 795 |     |     |     |     | 800 |

Leu Gly Lys Leu Lys Met Ile Ile Ala Lys Asn Gly Pro Asp Thr Asp
            805                 810                 815

Arg Leu Pro Thr Ser His Thr Cys Phe Asn Val Leu Leu Pro Glu
        820                 825                 830

Tyr Ser Asn Lys Glu Lys Leu Lys Glu Arg Leu Leu Lys Ala Ile Thr
        835                 840                 845

Tyr Ala Lys Gly Phe Gly Met Leu
    850                 855

<210> SEQ ID NO 8
<211> LENGTH: 2948
<212> TYPE: DNA
<213> ORGANISM: Xenopus tropicalis

<400> SEQUENCE: 8

| ctctcgcgag atgagacttt tgacgtcggg attagctgtc cggcaggggc caggaatctg | 60 |
| --- | --- |
| ggtattatcg gcgttgcggg acgtttaagc agcaatctgg gactgcgggc tgtgtttaaa | 120 |
| aattcgggtg tgttgggcgg tatgcagtag tgctgtggtt tagattgggg gtctcgcatg | 180 |
| agttccccgg acaagaggtg gcagcaggag agagagggag ccccggagcc cgaggagagg | 240 |
| aggaccaaca ccccccgcag cagcccggga cacagccctg aaggagacag atcaccagga | 300 |
| gacccttatt cagaaaatct agaaaatagc cgaatgaagc gagcagctgc aaagcatcta | 360 |
| atagaacgct actaccacca gttaactgag ggttgtggaa atgaaacctg cacgaatgaa | 420 |
| ttttgtgctt cctgtcccac tttttcttcgt atggataaca atgcagcagc cattaaggcc | 480 |
| ctcgagttat ataaggttaa tgcaaaactc tgtgatcctc atccctccaa gaaaggaaca | 540 |
| agctcatctt atctagagaa caattcgaaa agtgcccata caactcctg cacagaaaga | 600 |
| aagatgaata agaaagacct tcatggaccc agagatgact ttaaagatgt cactttcctg | 660 |
| tctgaagaaa aagtgtatga aattcttgaa ttgtgtagag aaaaagagga ctactcgcct | 720 |
| ttaattcggg tgatcgggag agtatttttcc agtgcagaag ctttggttca gagtttccga | 780 |
| aaagcaaagc accatacaaa ggaggagcta aaatccttgc aagaaaagga tgaagataag | 840 |
| gatgaagatg aaaaggaaaa agctgcatca tctgctgctg caatggaaga ggattctgga | 900 |
| gcatcatcct caaggttaag tgacaactca caaggagaca acaacataca gaaactaggc | 960 |
| cctgaagaag tgtctctaga tatagaagca gttcgacggg tgtatcacag gttactttct | 1020 |
| aatgagaaaa tagaaactgc ctttctgaat gcacttgtgt accttctcc taatgtggaa | 1080 |
| tgtgacttaa cttatcataa tgtttattca cgagatccca actatctcaa tttgtttata | 1140 |
| atcgtcatgg agaatggtaa tctccatagt cctgaatacc tggaaatggc tttaccgttg | 1200 |
| ttttgcaaag caatgagtaa attgccatta gcagcgcaag caaagttgat ccgtctttgg | 1260 |
| tcaaagtaca gcgctgagca gattcgccga atgatggaaa catttcagca gcttataacc | 1320 |
| tataaagtta taagtaacga gttcaacagt cgaaatttag tcaatgatga tgatgctatt | 1380 |
| gttgcagcaa caaagtgctt aaaaatggtt tactattcaa atgttgttgg tggagagatt | 1440 |
| gaaactgacc ataatgaaga ggaagatgat gaacctgttc ctgagtccag tgagttaact | 1500 |
| ctgcaggagc tgctagggga agaacgaaga aacaaaaaag ccctcgagt agatccctt | 1560 |
| gaaaccgaac ttggtgttaa aagcattgat tgcaggaaac ctctcatccc tttcgaggaa | 1620 |

| | |
|---|---|
| ttcgttaacg aaccactaaa tgatgttcta gaaatggaca agattatac tttcttttaaa | 1680 |
| gtagagactg aaaacaaatt ctcttttatg acttgcccct ttatcctgaa tgcagttaca | 1740 |
| aagaatcttg gtctgtatta tgacaacaga atccgcatgt acagtgaaag gcgaataact | 1800 |
| gttctgtata gtctagtgca aggacagcaa cttaacccct atttgaggct caaagtacgg | 1860 |
| cgagatcaca tcattgacga tgctcttgtt aggcttgaga tgattgccat ggaaaatcct | 1920 |
| gcagatttga agaagcaatt atatgtggaa tttgagggag aacaaggagt tgacgaagga | 1980 |
| ggtgtttcta aagagttttt ccaattagtt gttgaagaaa ttttcaaccc tgatattggt | 2040 |
| atgtttacgt atgatgagtc cactaaacac tcttggttca atccatcatc ttttgagaca | 2100 |
| gaaggacagt ttacacttat tggcattgtg ctgggccttg caatttacaa taattgcatt | 2160 |
| ctagatgtgc attttccaat ggttgtatat agaaaactaa tggggaaaaa aggaaccttc | 2220 |
| cgtgaccttg ctgattctca tcctgttctt tatcagagtt taaagaatt gttggagtat | 2280 |
| gaaggcaatg ttgaagaaga tatgatgatg actttccaga tctctcagac tgacctcttt | 2340 |
| ggaaatcctt taatgcacga cttaaaggaa atggagata aaatccccat acaaatgag | 2400 |
| aacagaaagg aatttgtcag tctatacaca gactatattc taaataaatc agtggaaaag | 2460 |
| caatttaaag ccttcagaag gggctttcac atggttacca atgaatcgcc tctgaaatat | 2520 |
| ctgtttagac cagaggagat tgaacttctt atttgtggaa gtaggaattt agatttccaa | 2580 |
| gctctgaaag atactacgga atatgatggt ggctatacca gagattcaaa tataataaag | 2640 |
| gagttttggg aaattgtaaa ttcttttcaca gaggaacaaa aaagattgtt cttgcaattt | 2700 |
| acaacaggca cggacagagc acctgtaggt gggctaggca aattaaagat gattatagcc | 2760 |
| aaaaacggcc ctgatacaga caggttacca acatctcata cttgctttaa tgtccttttg | 2820 |
| cttccggagt actcaaataa agagaaactg aaggagagat tgttaaaggc catcacttat | 2880 |
| gctaaggggt ttggtatgct ctaaaaacaa aggcaagcgt gctaaaaaaa aataaaaaaa | 2940 |
| aaaaaaaa | 2948 |

<210> SEQ ID NO 9
<211> LENGTH: 857
<212> TYPE: PRT
<213> ORGANISM: Danio rerio

<400> SEQUENCE: 9

Met Lys Arg Ala Ala Ala Lys His Leu Ile Glu Arg Tyr Tyr His Gln
1               5                   10                  15

Leu Thr Glu Gly Cys Gly Asn Glu Ala Cys Thr Asn Glu Ala Cys Gly
            20                  25                  30

Ser Ser Pro Gly Phe Gln Arg Met Asp Asn Asn Ala Ala Ala Ile Lys
        35                  40                  45

Ala Leu Glu Leu Tyr Lys Asn Asn Ala Lys Leu Cys Asp Pro His Pro
    50                  55                  60

Ser Lys Lys Gly Ala Ser Ser Ala Phe Pro Glu Asn Ser Ala Lys Gly
65                  70                  75                  80

Ala His Asn Phe Ser Ala Cys Ser Asn Gly Lys Met Asn His Lys Asp
                85                  90                  95

Leu Pro Pro Thr Arg Glu Asp Phe Arg Asp Leu Asn Phe Leu Thr Glu
            100                 105                 110

Asp Lys Val Tyr Glu Ile Leu Ser Ile Cys Ser Glu Thr Glu Asp Tyr
        115                 120                 125

Ser Pro Leu Ile Arg Val Ile Gly Arg Val Phe Ser Ser Ala Glu Ser

```
            130                 135                 140
Leu Val Gln Ser Phe Arg Lys Ala Lys Gln His Thr Lys Glu Glu Leu
145                 150                 155                 160

Lys Ser Leu Gln Ala Lys Asp Glu Asp Lys Asp Glu Asp Lys Glu
                165                 170                 175

Thr Ala Ser Gly Ser Ser Thr Ala Met Glu Val Glu Pro Glu Ala Ser
                180                 185                 190

Ala Ser Ser Gly Asp Gly Ser Ser His Gly Glu Asn Asn Val Gln Lys
                195                 200                 205

Leu Gly Pro Val Glu Val Ser Val Asp Ile Asp Ala Val Arg Arg Val
210                 215                 220

Tyr Asp Arg Leu Leu Ser Asn Glu Lys Ile Glu Ala Ala Phe Leu Asn
225                 230                 235                 240

Ala Leu Val Tyr Leu Ser Pro Asn Val Glu Cys Asp Leu Thr Tyr His
                245                 250                 255

Asn Val Tyr Ala Ala Asp Pro Asn Tyr Leu Asn Val Phe Ile Ile Val
                260                 265                 270

Met Glu Asn Ser Asn Leu His Ser Pro Glu Tyr Leu Glu Ile Ala Leu
                275                 280                 285

Pro Gln Phe Cys Lys Ala Met Ser Lys Leu Pro Leu Pro Ala Leu Ala
290                 295                 300

Lys Leu Ala Arg Leu Trp Ser Gln Tyr Gly Val Asp Gln Ile Arg Arg
305                 310                 315                 320

Leu Val Glu Thr Phe Gln Gln Leu Ile Thr Tyr Thr Val Ile Ser Asn
                325                 330                 335

Glu Phe Ser Ser Asp Asn Leu Val Asn Glu Asp Asp Gly Val Val Ala
                340                 345                 350

Ala Thr Lys Cys Leu Lys Ile Val Tyr Tyr Ala Asn Val Leu Gly Gly
                355                 360                 365

Asp Leu Asp Thr Asp His Asn Glu Glu Asp Asp Glu Pro Ile Pro
                370                 375                 380

Glu Ser Ser Glu Leu Thr Leu Gln Glu Leu Leu Gly Glu Glu Arg Arg
385                 390                 395                 400

Asn Lys Lys Gly Pro Arg Val Asp Pro Leu Glu Thr Glu Met Gly Ile
                405                 410                 415

Arg Ala Ser Asp Cys Arg Lys Pro Leu Ile Pro Phe Glu Glu Phe Ile
                420                 425                 430

Asn Glu Pro Leu Asn Glu Val Leu Glu Met Asp Lys Asp Tyr Thr Phe
                435                 440                 445

Phe Lys Val Glu Thr Glu Ser Lys Phe Ser Phe Met Thr Cys Pro Phe
450                 455                 460

Ile Leu Asn Ala Val Thr Lys Asn Leu Gly Leu Tyr Tyr Asp Asn Arg
465                 470                 475                 480

Ile Arg Met Tyr Ser Glu Arg Arg Ile Thr Ala Leu Tyr Ser Leu Val
                485                 490                 495

Gln Gly Gln Gln Leu Asn Pro Tyr Leu Arg Leu Lys Val Arg Arg Asp
                500                 505                 510

His Ile Ile Asp Asp Ala Leu Val Arg Leu Glu Met Ile Ala Met Glu
                515                 520                 525

Asn Pro Ala Asp Leu Lys Lys Gln Leu Tyr Val Glu Phe Glu Gly Glu
                530                 535                 540

Gln Gly Val Asp Glu Gly Gly Val Ser Lys Glu Phe Phe Gln Leu Val
545                 550                 555                 560
```

Val Glu Glu Ile Phe Asn Pro Asp Ile Gly Met Phe Thr Tyr Asp Glu
                565                 570                 575

Ser Thr Lys Leu Phe Trp Phe Asn Pro Ser Ser Phe Glu Asn Glu Gly
            580                 585                 590

Gln Phe Thr Leu Ile Gly Ile Val Leu Gly Leu Ala Ile Tyr Asn Asn
        595                 600                 605

Cys Ile Leu Asp Val His Phe Pro Met Val Ile Tyr Arg Lys Leu Met
    610                 615                 620

Gly Lys Lys Gly Thr Phe Arg Asp Leu Ala Asp Ser His Pro Val Leu
625                 630                 635                 640

Phe Gln Ser Leu Lys Asp Leu Met Glu Tyr Glu Gly Asn Val Glu Glu
                645                 650                 655

Asp Met Met Ile Thr Phe Gln Ile Ser Gln Thr Asp Leu Phe Gly Asn
            660                 665                 670

Pro Leu Met Tyr Asp Leu Lys Glu Ser Gly Asp Lys Ile Pro Val Thr
        675                 680                 685

Asn Glu Asn Arg Lys Asp Phe Val Ala Leu Tyr Ala Glu Tyr Met Leu
    690                 695                 700

Asn Lys Ser Val Glu Lys Gln Phe Lys Ala Phe Arg Arg Gly Phe His
705                 710                 715                 720

Met Val Thr Asn Glu Ser Pro Leu Lys Tyr Leu Phe Arg Pro Glu Glu
                725                 730                 735

Ile Glu Leu Leu Ile Cys Gly Ser Arg Asn Leu Asp Phe Gln Ala Leu
            740                 745                 750

Glu Glu Ser Thr Glu Tyr Asp Gly Gly Tyr Asn Lys Asp Ser Arg Ile
        755                 760                 765

Ile Arg Asp Phe Trp Glu Thr Val His Ser Phe Glu Gln Glu Lys Lys
    770                 775                 780

Arg Leu Phe Leu Gln Phe Thr Thr Gly Thr Asp Arg Ala Pro Val Gly
785                 790                 795                 800

Gly Leu Gly Lys Leu Lys Met Ile Ile Ala Lys Asn Gly Pro Asp Ser
                805                 810                 815

Asp Arg Leu Pro Thr Ser His Thr Cys Phe Asn Val Leu Leu Leu Pro
            820                 825                 830

Glu Tyr Ser Thr Val Glu Lys Leu Lys Glu Arg Leu Leu Lys Ala Ile
        835                 840                 845

Thr Tyr Ala Lys Gly Phe Gly Met Leu
    850                 855

<210> SEQ ID NO 10
<211> LENGTH: 4093
<212> TYPE: DNA
<213> ORGANISM: Danio rerio

<400> SEQUENCE: 10
caagatggcc gcgaatattt tgtggagggg ttggagttga atacacgccg cactagaagc      60
gattgtgatg ttgagagacc agattcattc gtcagcatca gaacacctcc aaaagattgc     120
tacctgacaa ccttttgggtc tctttgagtt cagaaccgta gaagagtgtg atattggaaa    180
ctttaaagca agtctaatga agcgagcggc tgcaaagcat ttaattgagc gctactacca    240
ccagttaaca gagggctgtg gaaatgaggc ctgcacgaat gaggcttgtg gctcttctcc    300
gggtttccag cgcatggata caatgcagc agccatcaag gccctggagt tatataagaa     360
taatgccaaa ctgtgtgatc ctcatccctc taagaaagga gccagttcag ccttcccgga    420

```
gaacagtgcc aaaggagctc acaacttctc tgcttgcagc aacgaaaga tgaaccataa    480 ggacctgcca cccacaaggg aggactttag agatctgaat ttcttgactg aggataaggt    540
gtatgaaatc ctgagcatct gcagtgagac agaggactat tctcctctaa tccgtgttat    600
tggtcgggtt ttctcaagtg cagagagtct agtccagagt ttccgcaaag caaacaaca    660 caccaaggaa gagctcaagt cccttcaggc caaggatgaa gacaaagatg aagatgagaa    720
agaaacggct tctggttcat ccacagcaat ggaggtggaa ccagaagctt cagcatcaag    780
tggagacggg tcatctcatg gggagaacaa cgtccaaaag ttgggtcctg tagaagtttc    840
tgtagacatt gatgctgtaa gaagagtgta cgacagatta ttatcgaatg agaagattga    900
ggcagctttc ctcaacgcgt tagtctattt gtcgcccaac gtagagtgtg acctcaccta    960
tcacaatgtg tacgccgctg accctaatta cctgaacgtc ttcatcattg tgatggagaa   1020
cagtaacctc cacagtcccg aatacttaga aatcgccttg ccacagttct gcaaggccat   1080
gagcaagcta cctcttccgg ctctggccaa gcttgcacgg ttgtggtcgc agtacggtgt   1140
ggaccagatc cgacgtttgg tcgagacttt ccagcagctt attacctaca cggtcatcag   1200
caacgagttc agcagtgata acctagtcaa tgaggatgat ggtgtggtgg cagccaccaa   1260
gtgcttgaaa atcgtctact atgcaaacgt gctgggcggc gacctagaca cggatcacaa   1320
tgaggaggac gacgatgaac cgatccctga gtcaagtgag ctgacgctgc aggagctgct   1380
gggagaggag agacgcaata aaaaaggccc tcgagtggat ccgctggaga cagaaatggg   1440
catccgtgcc tcggactgtc gaaaaccct catcccattc gaggagttca tcaatgaacc   1500
actcaatgag gtgctggaaa tggacaaaga ctataccttc ttcaaggtgg agacagagag   1560
caagttctcc tttatgacct gcccttccat acttaacgct gtgactaaga atctgggcct   1620
gtactacgac aaccggatcc gcatgtatag cgagcgcagg attactgccc tctatagttt   1680
ggtgcaagga cagcaactaa acccttatct gcgactcaaa gtgcgcagag accacatcat   1740
agacgatgct cttgtcaggt tggagatgat tgccatggaa aaccctgcag acttgaagaa   1800
gcaactgtat gtggagtttg agggtgagca aggagtagat gagggaggag tatccaaaga   1860
attctttcaa ctggtagtag aggagatctt caacccagat ataggcatgt ttacctatga   1920
tgaaagcaca aaacttttct ggttcaaccc ttcatcattt gagaatgaag gccagttcac   1980
tttgataggc atcgtcctgg gcctagctat ctacaataac tgcattctgg atgtgcattt   2040
ccctatggtg atttacagaa aactaatggg aaagaaagga acgtttcgag accttgcaga   2100
ctctcatccg gttctttttc agagtctgaa agatctcatg gagtatgaag caatgttga   2160 agaagacatg atgattacct tccagatctc gcaaacagac ctgtttggaa acccactaat   2220
gtacgattta aaggaaagcg tgataaaat ccctgttacc aatgagaaca gaaggattt   2280 tgtggcgctc tatgcagagt acatgctgaa caaaagtgtg gagaaacagt ttaaggcctt   2340
tagaagagga ttccacatgg tcactaatga gtctccactg aaatatctgt ttcgaccgga   2400
ggagattgag ctgcttatat gtggcagcag gaaccttgac ttccaagcac ttgaagagag   2460
caccgaatat gatggaggat acaacaaaga ctcgcgcatt attagggatt tctgggagac   2520
ggtgcactca tttgagcagg agaagaagag actgtttctc cagttcacca ctggcacaga   2580
tagagctcca gttggaggtt taggcaaact caagatgatt attgccaaaa tggtcccga   2640 ctcagacagg ttacccacct ctcatacctg cttcaacgtg ctgctcctcc ccgaatactc   2700
caccgtggag aaacttaaag agagactcct taaagccatc acttacgcca aaggcttcgg   2760
```

```
catgctctga ggctaaagaa ctcactctag ccctcagagg agaatcagct acatccacaa    2820
ctaatcgtaa atatcaagtt taaatgtaag gcaacatgaa atgggttcaa aatggggaag    2880
ttctggtgac cgtgtgcctg tgcctaaaaa gtagataaaa ccacactgga ctcatggctc    2940
tctctctttc tctgtctctc tctctctccc tcttatgtaa gtgttcaggt tcccattttt    3000
ttgtatgcac tgagatatag cgttatttat tttaagggat gaaatctctt gtcatgtctg    3060
ccaggaattc cacacttttg ttgcttcata gtcataaaaa caggagggac ggttggaagt    3120
tttcaacggc tgcaggactg atcaccaact aaacttaata aaacaagatc aagggagga    3180 ggtggaactt tgttgtatta cggttgaact gtgaaagtgc acttaactct attcagaatg    3240
tctttgtttt attttttgatt ttttttttgtc aacccttagg cttttctttt tagttttggc    3300
tcgtgcttca ttggtcttcc ctagttcgtt cacatttgcg gcaatgtttg aaaggtacag    3360
agcagcctca gtctcagttt ggcatccagg aatctgtatt tattgagaat ctgcattgtt    3420
tgtaatgccg tcgtgctgct cgtttatggc cagtgttctg catttcgctt cagattcgac    3480 ttttttctctc cctcacacac aactgaccgg tttgctaaag atcacagtgg tgcactcctg    3540
ccgaaaacga gtagtgttat aaaggagaga tctcaacttc ctataaaact ctgtcagaag    3600
cttcctacta gtgtttgttt gttttgttat ctgtcttgtt ttaattcaag atggcagact    3660
tttagtccat gaatgctaat tgacggtgcc ccatgaagaa agcgttttag ttgcgctttt    3720 tttttcttt gctctgcaca gtgtctggcc cgatacattt ggatgaaaat gaggggaaat    3780
tggcacaagt cgtaccacta tcttgtcgtg ccaaacagtt atgctgagaa tcgccgctcc    3840
ggttttgttc aggcgtagct ggaaatccag attagtgatg ccctgttcac tttttttttt    3900
tttgtttatt ttgtttttcc ttattccctc ttgcagatta aatgtgactg tggtttgatc    3960
cactgctgat ggcgctaaca taaaggggg aaacagaact tgatattgag aatgacaaca    4020
tttgattgtt tcaagttatt cttaaataaa ttcaaaactg aaaacaaaa aaaaaaaaa    4080 aaaaaaaaaa aaa                                                       4093

<210> SEQ ID NO 11
<211> LENGTH: 20
<212> TYPE: DNA
<213> ORGANISM: Rattus norvegicus

<400> SEQUENCE: 11
ggccctgcag agatgcaatc                                                  20

<210> SEQ ID NO 12
<211> LENGTH: 17
<212> TYPE: DNA
<213> ORGANISM: Rattus norvegicus

<400> SEQUENCE: 12
ggagccctcc gccggca                                                     17

<210> SEQ ID NO 13
<211> LENGTH: 17
<212> TYPE: DNA
<213> ORGANISM: Rattus norvegicus

<400> SEQUENCE: 13
taccctcccc aggcccc                                                     17

<210> SEQ ID NO 14
<211> LENGTH: 20
```

```
<212> TYPE: DNA
<213> ORGANISM: Rattus norvegicus

<400> SEQUENCE: 14
gcatttctag tacatcatcc                                              20

<210> SEQ ID NO 15
<211> LENGTH: 20
<212> TYPE: DNA
<213> ORGANISM: Artificial
<220> FEATURE:
<223> OTHER INFORMATION: Ub3aDelF1 forward primer

<400> SEQUENCE: 15
aacaccaagc ctctctcagc                                              20

<210> SEQ ID NO 16
<211> LENGTH: 20
<212> TYPE: DNA
<213> ORGANISM: Artificial
<220> FEATURE:
<223> OTHER INFORMATION: Ub3aDelR1 reverse primer

<400> SEQUENCE: 16
accaggcctc aaaattgaca                                              20

<210> SEQ ID NO 17
<211> LENGTH: 20
<212> TYPE: DNA
<213> ORGANISM: Artificial
<220> FEATURE:
<223> OTHER INFORMATION: Ub3aDelF2 forward primer

<400> SEQUENCE: 17
ctcccgagta caccgaagac                                              20

<210> SEQ ID NO 18
<211> LENGTH: 20
<212> TYPE: DNA
<213> ORGANISM: Artificial
<220> FEATURE:
<223> OTHER INFORMATION: Ub3aDelR2 reverse primer

<400> SEQUENCE: 18
gggaacagca aaagacatgg                                              20

<210> SEQ ID NO 19
<211> LENGTH: 22
<212> TYPE: DNA
<213> ORGANISM: Artificial
<220> FEATURE:
<223> OTHER INFORMATION: Ub3aDelSpcfcF3 forward primer

<400> SEQUENCE: 19
gtaccaagaa gtcacatggc tc                                           22

<210> SEQ ID NO 20
<211> LENGTH: 23
<212> TYPE: DNA
<213> ORGANISM: Artificial
<220> FEATURE:
<223> OTHER INFORMATION: Ub3aDelSpcfcR3 reverse primer

<400> SEQUENCE: 20
gcaggctgct attacactaa gga                                          23
```

```
<210> SEQ ID NO 21
<211> LENGTH: 23
<212> TYPE: DNA
<213> ORGANISM: Artificial
<220> FEATURE:
<223> OTHER INFORMATION: Ub3aDelSpcfcF4 forward primer

<400> SEQUENCE: 21
acatggctct aaaagagttc agg                                            23

<210> SEQ ID NO 22
<211> LENGTH: 23
<212> TYPE: DNA
<213> ORGANISM: Artificial
<220> FEATURE:
<223> OTHER INFORMATION: Ub3aDelSpcfcR4 reverse primer

<400> SEQUENCE: 22
gtgattcact agggatatgc agg                                            23

<210> SEQ ID NO 23
<211> LENGTH: 24
<212> TYPE: RNA
<213> ORGANISM: Rattus norvegicus

<400> SEQUENCE: 23
uugugauucu gaacaguucu uggg                                           24

<210> SEQ ID NO 24
<211> LENGTH: 22
<212> TYPE: RNA
<213> ORGANISM: Rattus norvegicus

<400> SEQUENCE: 24
agcacuguac uacuaggggc uc                                             22

<210> SEQ ID NO 25
<211> LENGTH: 67
<212> TYPE: DNA
<213> ORGANISM: Rattus norvegicus

<400> SEQUENCE: 25
ccaagagcga aggcgaacta gagtagggcc ctgcagagat taaataaatc ccaggccccc    60
cagaatt                                                              67

<210> SEQ ID NO 26
<211> LENGTH: 67
<212> TYPE: DNA
<213> ORGANISM: Rattus norvegicus

<400> SEQUENCE: 26
ccaagagcga aggcgaacta gagtagggcc ccgcagaatt aaataattga tgatgatgat    60
gatgatg                                                              67
```

ANIMAL MODEL OF ANGELMAN SYNDROME

CROSS-REFERENCE TO RELATED APPLICATIONS

The present application is the National Stage of International Application No. PCT/US2017/054992, filed Oct. 3, 2017, which claims the benefit of U.S. Provisional Application Ser. No. 62/403,463, filed Oct. 3, 2016, each of which is hereby incorporated by reference herein in its entirety, including any figures, tables, nucleic acid sequences, amino acid sequences, or drawings.

SEQUENCE LISTING

The Sequence Listing for this application is labeled "2NR4499.TXT" which was created on Mar. 4, 2019 and is 66 KB. The entire contents of the sequence listing is incorporated herein by reference in its entirety.

BACKGROUND OF THE INVENTION

Angelman Syndrome (AS) is a devastating neurological disorder with a prevalence of 1 in 15,000. AS presents with ataxia, frequent smiling, and laughter, lack of speech, and severe, debilitating seizures. Epilepsy in AS is often refractory to many prescribed medications, and frequently involves many seizure types. Furthermore, chronic, intractable epilepsy is shown to cause hippocampal damage and is associated with cognitive decline.

Nearly all cases of AS result from the disruption of a single gene that encodes an E3 ubiquitin ligase, UBE3A, a protein involved in the ubiquitin mediated protein degradation pathway (Kishino T et al., *Nature Genetics*, 1997, 15:74-77). The absence of this protein results in the accumulation of regulatory proteins, such as arc and ephexin 5 in the postsynaptic density, which is believed to cause abnormal dendritic spine morphology (filopodial) and density in hippocampal pyramidal neurons leading to aberrant synaptic function. These alterations in spine morphology and synaptic function in neurons provides an explanation for the severe behavioral and cognitive manifestations of the syndrome.

Mouse models have been developed using different strategies to disrupt the Ube3a gene. One mouse line utilized an Epstein-Barr virus latent membrane protein 2A (Lmp2a) transgenic insertion to remove the entire equivalent AS critical region (J. M. Gabriel et al., *Proc Natl Acad Sci USA* 96, 9258 (1999); U. Albrecht et al., *Nat Genet* 17, 75 (1997)). Another mouse model utilized a specific maternal gene knockout in Ube3a via a null mutation (Y. H. Jiang et al., *Neuron* 21, 799 (1998)). While both of these mouse models effectively disrupt maternal Ube3a gene expression, there are advantages and disadvantages for both models.

BRIEF SUMMARY OF THE INVENTION

The present invention concerns ubiquitin-protein ligase E3A-deficient (UBE3A-deficient) animals that are useful in modeling Angelman Syndrome (AS). The animals can have a genome lacking the entire Ube3a gene (including all isoforms and alternative promoters), and may be used for basic research on the disease as well as applied research for pre-clinical testing of potential therapeutics.

A UBE3A-deficient rat was produced containing a large deletion (88 kb) of the entire Ube3a gene (including all isoforms and alternative promoters). To the inventors' knowledge, this is the first rat model of AS.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 5A, Genome-wide significant DMRs overlapped 5,284 annotated genes. Compared to a background set of control DMRs (same CpG density and number but not differentially methylated), AMC DMRs were significantly enriched for 5' upstream regions and introns and de-enriched for non-genic loci (Other). *$p<0.05$ by Fisher's exact test. FIG. 5B, Gene ontology (GO terms) significantly associated with AMC induced DMRs in P9 hypothalamus.

FIG. 6A, Circos plot of chromosome position (outer ring), DMRs ($2^{nd}$ ring), differentially expressed genes ($3^{rd}$ ring), and five differential miRNAs (interior lines) showing chromosome origin and target gene locations. FIG. 6B, heatmap represents fold-change differences for each sample (n=7 H, n=5 NH, all males) for the 5 AMC differential miRNAs. FIG. 6C, gene ontology (GO terms) significantly associated with 2,464 AMC induced differentially expressed genes in P9 hypothalamus.

FIGS. 7A, 7B-1, 7B-2, 7C. Isoform-specific changes in Ube3a in response to handling (AMC). FIG. 7A, three Ube3a isoforms, shown 5' (left) to 3' (right), share 9 exons in common but Ube3a-1 is the shortest, lacking the E3 ligase catalytic domain (right) and Ube3a-2 is the longest, with a unique N-terminus. The noncoding RNA Ube3a1 contains an alternative 3'UTR that binds miRNA134 [73]. qRT-PCR with isoform-specific primers (stars) was performed on RNA isolated from P9 rat hypothalamic from pups either handled for 15 min per day from P2-P8 or non-handled (FIGS. 7B-1 and 7B-2). N=19 handled, 10 non-handled, representing both males and females (no sex differences observed). ***P<0.001, *P<0.05. FIG. 7C shows that the Ube3a1 specific 3'UTR (SEQ ID NO:23) contains a predicted recognition site for miR-542-5p (SEQ ID NO:24), which was upregulated with AMC (FIG. 6).

FIG. 8. Overlapping imprinted genes altered by rat AMC and UBE3A siRNA knockdown in human Dup15q neurons. Venn diagrams show the number of imprinted differentially expressed genes (DE, genes, FIG. 8. left Venn diagram) or genes that overlap DMRs (FIG. 8, right Venn diagram) in handled vs nonhandled rat (AMC) or a comparison of human SH-15M Dup15q cells with either UBE3A siRNA vs control siRNA (UBE3A KD) [6] that are also within imprinted loci. Overlapping genes are listed below the Venn diagrams (Ube3a, Ano1, Magi2, Gnas, Osbp15, Ctnna3, maternal; Dlk1, Ndn, Rasgrf1, Grb10, paternal; Gabrb3, Ntm, biallelic expression). *P<0.05 by Fisher's exact test.

FIGS. 9A-9D. Examples of neonatal chromatin decondensation at two imprinted snoRNA/miRNA clusters detected by FISH in mouse hypothalamic neurons. Chromatin was detected by fluorescence in situ hybridization (FISH) See Leung et al., 2009 [22] for a more detailed explanation. Chromatin decondensation was observed by FISH to occur specifically in neurons at both Snrpn-Ube3a and G112 imprinted loci (location of FISH BAC probes shown). Paternal decondensation at Snrpn-Ube3a predominantly occurred within the first 2 weeks of life (P1-P14) and preceded the accumulation of snoRNAs encoded by Snord116 (HBII-85) in neuronal nucleoli.

FIGS. 10A-10D. Ube3a CRISPR deletion rat model. FIG. 10A, Rat Ube3a deletion CRISPR design and (FIG. 10B) sequences of 2 founders (SEQ ID NOs:25 and 26). FIG. 10C, Western blot of adult brain from Founder 2 line showing absence of UBE3A in homozygous deletion (KO) rats and a faintly detectable UBE3A band in maternal deletion (AS), as expected from paternal expression in glia. FIG. 10D, UBE3A Western blot of adult cortex (Founders 1&2) vs. two non-neuronal tissues where UBE3A is still paternally expressed, as expected.

FIG. 12A) Structure of TAT-S1 ATF protein, including maltose binding protein (MBP) and VP64 transcriptional activator cell penetrating peptide (TAT) cell penetrating peptide, mCherry and HA reporters, nuclear localization signal (NLS), 6 zinc finger modules directed to a 18-bp site within the PWS-IC (Snrpn promoter), and a KRAB repression domain. FIG. 12B) TAT-S1 and TAT-S6 localize to brain (red) within 1-8 hours after i.p. injection (FIG. 12C), but not a mock injection of mCherry without TAT. FIG. 12D) TAT-S1 or control (NT) proteins were injected i.p. (200 mg/kg, 3×/week, 4 weeks) in WT and AS adult mice. Quantitation of UBE3A IF in hippocampus shows a significant increase in UBE3A IF in AS mice (left 3) treated with TAT-S1 and in WT compared to NT-AS. FIG. 12E) Western blot results of brain cytosolic lysates from mice treated as described in (FIG. 12D) show that the increased expression of UBE3A in AS mice following TAT-S1 treatment was due to a smaller isoform of UBE3A detectable by 2 different antibodies. Details are provided in Bailus et al., 2016 [2], which is incorporated herein by reference in its entirety.

BRIEF DESCRIPTION OF THE SEQUENCES

SEQ ID NO:1 is an amino acid sequence of human ubiquitin-protein ligase E3A.
  DEFINITION Ubiquitin-protein ligase E3A.
  ACCESSION Q05086
  VERSION Q05086.4 GI:215274240
  SOURCE *Homo sapiens* (human)
SEQ ID NO:2 is an nucleotide sequence of human ubiquitin-protein ligase E3A.
  DEFINITION *Homo sapiens* ubiquitin protein ligase E3A (UBE3A), transcript variant 1, mRNA.
  ACCESSION NM_130838
  VERSION NM_130838.1 GI:19718761
  SOURCE *Homo sapiens* (human)
SEQ ID NO:3 is an amino acid sequence of rat ubiquitin-protein ligase E3A.
  DEFINITION ubiquitin-protein ligase E3A [*Rattus norvegicus*].
  ACCESSION NP_001178766 XP_341868
  VERSION NP_001178766.1 GI:300797458
  SOURCE *Rattus norvegicus* (Norway rat)
SEQ ID NO:4 is a nucleotide sequence of rat ubiquitin-protein ligase E3A.
  DEFINITION *Rattus norvegicus* ubiquitin protein ligase E3A (Ube3a), mRNA.
  ACCESSION NM_001191837 XM_341867
  VERSION NM_001191837.2 GI:394025712
  SOURCE *Rattus norvegicus* (Norway rat)
SEQ ID NO:5 is an amino acid sequence of Rhesus monkey ubiquitin-protein ligase E3A.
  DEFINITION ubiquitin-protein ligase E3A [*Macaca mulatta*].
  ACCESSION NP_001247969 XP_001108510 XP_001108562 XP_001108661 XP_002804732
  VERSION NP_001247969.1 GI:386782071
  SOURCE *Macaca mulatta* (Rhesus monkey)
SEQ ID NO:6 is a nucleotide sequence of Rhesus monkey ubiquitin-protein ligase E3A.
  DEFINITION *Macaca mulatta* ubiquitin protein ligase E3A (UBE3A), mRNA.
  ACCESSION NM_001261040 XM_001108510 XM_001108562 XM_001108661 XM_002804686
  VERSION NM_001261040.1 GI:386782070
  SOURCE *Macaca mulatta* (Rhesus monkey)
SEQ ID NO:7 is an amino acid sequence of tropical frog ubiquitin-protein ligase E3A.
  DEFINITION ubiquitin-protein ligase E3A [*Xenopus tropicalis*].
  ACCESSION NP_001001213
  VERSION NP_001001213.1 GI:47575738
  SOURCE *Xenopus tropicalis* (tropical clawed frog)
SEQ ID NO:8 is a nucleotide sequence of frog ubiquitin protein ligase E3A.
  DEFINITION *Xenopus tropicalis* ubiquitin protein ligase E3A (human papilloma virus E6-associated protein, Angelman syndrome) (ube3a), mRNA.
  ACCESSION NM_001001213
  VERSION NM_001001213.1 GI:47575737
  SOURCE *Xenopus tropicalis* (tropical clawed frog)

SEQ ID NO:9 is an amino acid sequence of frog ubiquitin protein ligase E3A.
  DEFINITION ubiquitin-protein ligase E3A [*Danio rerio*].
  ACCESSION  NP_001007319  XP_001331815  XP_001333994
  VERSION NP_001007319.1 GI:55925524
  SOURCE *Danio rerio* (zebrafish)

SEQ ID NO:10 is a nucleotide sequence of zebra fish ubiquitin protein ligase E3A.
  DEFINITION *Danio rerio* ubiquitin protein ligase E3A (ube3a), mRNA.
  ACCESSION  NM_001007318  XM_001331779  XM_001333958
  VERSION NM_001007318.1 GI:55925523
  SOURCE *Danio rerio* (zebrafish)

Figure 7A:
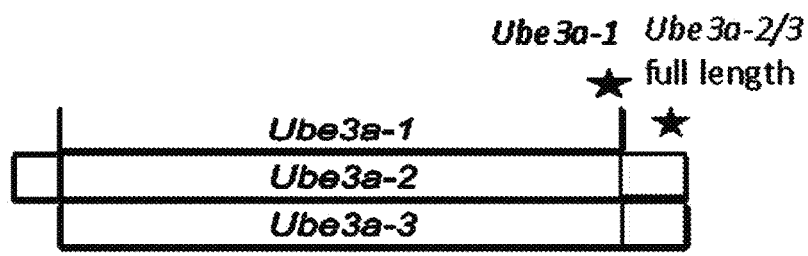
Figures 1, 7B:
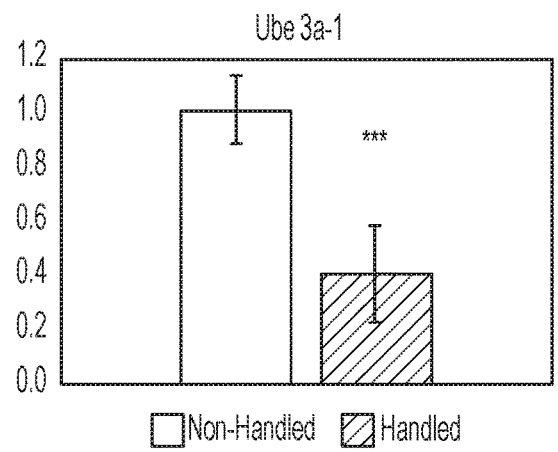
Figures 2, 7B:
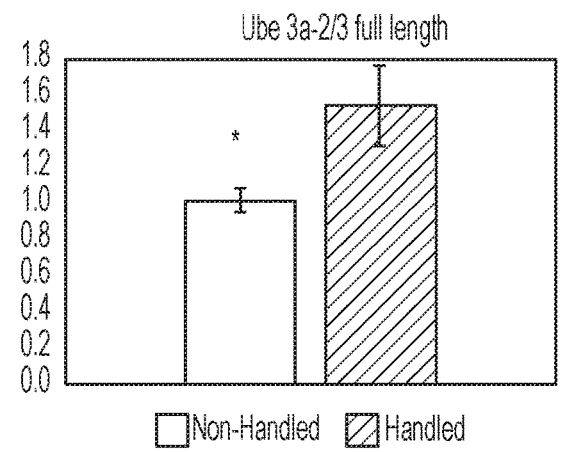
Figure 7C:
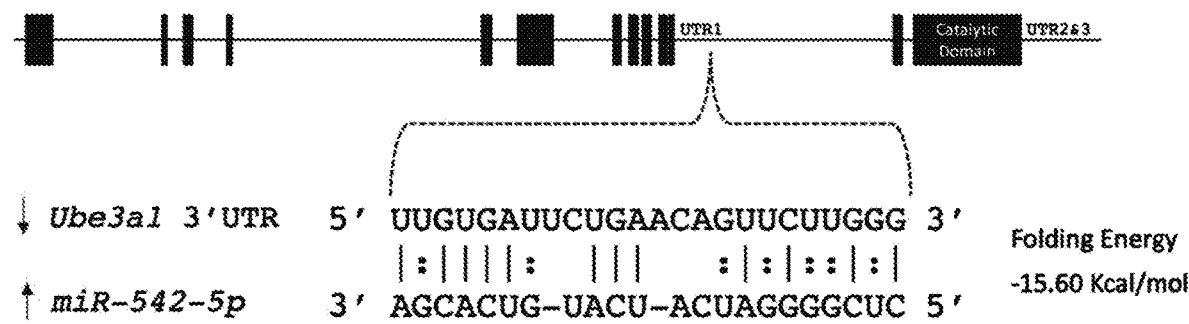
Figure 10C:
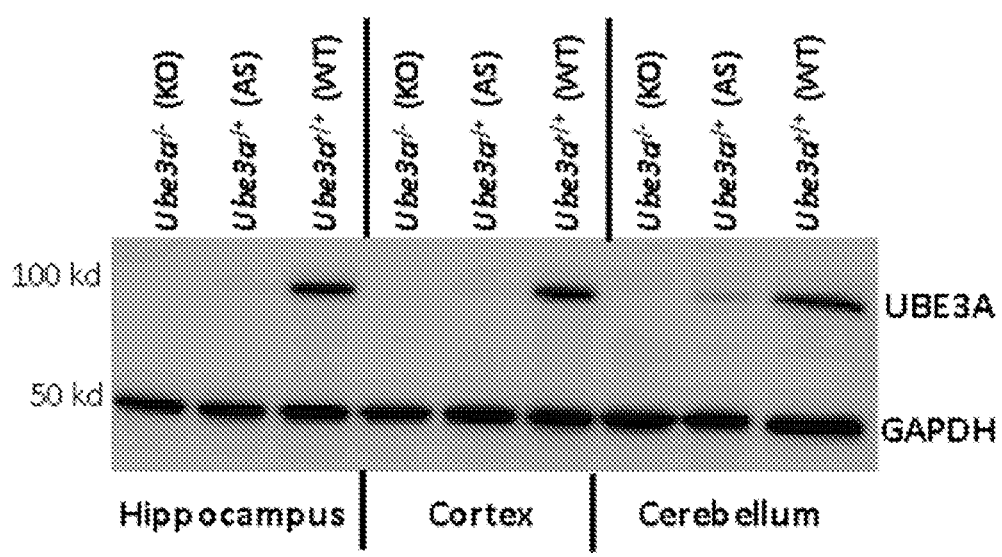

SEQ ID NO:11 is a 5' CRISPR target site.
SEQ ID NO:12 is a 5' CRISPR target site.
SEQ ID NO:13 is a 3' CRISPR target site.
SEQ ID NO:14 is a 3' CRISPR target site.
SEQ ID NO:15 is a forward primer, Ub3aDelF1.
SEQ ID NO:16 is a reverse primer, Ub3aDelR1.
SEQ ID NO:17 is a forward primer, Ub3aDelF2.
SEQ ID NO:18 is a reverse primer, Ub3aDelR2.
SEQ ID NO:19 is a forward primer, Ub3aDelSpcfcF3.
SEQ ID NO:20 is a reverse primer, Ub3aDelSpcfcR3.
SEQ ID NO:21 is a forward primer, Ub3aDelSpcfcF4.
SEQ ID NO:22 is a reverse primer, Ub3aDelSpcfcR4.
SEQ ID NO:23 is a Ube3a1 specific 3'UTR (FIG. 7C).
SEQ ID NO:24 is a predicted recognition site for microRNA miR-542-5p (FIG. 7C).
SEQ ID NO:25 is a rat Ube3a deletion CRISPR sequence of Founder 1: Del 90457 bp/ins 8 bp (FIG. 10B).
SEQ ID NO:26 is a rat Ube3a deletion CRISPR sequence of Founder 2: Del 90476 bp/ins 1bp (FIG. 10B).

DETAILED DESCRIPTION OF THE INVENTION

The present invention concerns knockout animals for the ubiquitin-protein ligase E3A gene, Ube3a, which are useful in modeling Angelman Syndrome. These animals, which lack the entire Ube3a gene (including all isoforms and alternative promoters), may be used for basic research on the disease as well as applied research for pre-clinical testing of potential therapeutics.

As used herein, the phrases "lacking an entire Ube3a gene" or "lacks an entire Ube3a gene" means lacking at least the coding sequence of the Ube3a gene, including each exon of the gene, e.g., by deletion. Lacking an entire Ube3a gene can also encompass lacking the other portions of the gene as well (introns, regulatory sequences, etc.). Various animals models of Angelman Syndrome have been developed using different strategies to disrupt the Ube3a gene (see, for example, Jana N R, *Neural Plasticity*, July 2012, 2012(2): 710943, and Loon L H et al., 2012, Angelman Syndrome: Proteomics Analysis of an UBE3A Knockout Mouse and Its Implications, Chapter 7, Advanced Topics in Neurological Disorders, Dr Ken-Shiung Chen (Ed.), which are each incorporated herein by reference in their entirety). The animals of the present invention that have the entire Ube3a gene deleted have advantages over existing mouse models in which the Ube3a gene is present but contains a mutation in an exon (e.g., to generate a stop codon or to result in shift of the open reading frame), as this genomic structure of the existing models potentially allows some isoforms to splice around the disrupted exon.

Depending upon the technique used to produce the animal, a subset of cells (e.g., a cell population) may lack the entire Ube3a gene, a tissue may lack the entire Ube3a gene, or the whole organism may lack entire Ube3a gene.

One aspect of the invention concerns a non-human animal comprising cells with a genome having a deletion of the entire Ube3a gene (lacking at least the coding sequence of the Ube3a gene). In some embodiments, one or more populations of the animal's cells have the deletion of the entire Ube3a gene. In some embodiments, the whole animal's genome has the deletion of the entire Ube3a gene.

In some embodiments, the animal is a non-human mammal. In some embodiments, the animal is a rodent, such as a rat or mouse. In some embodiments, the animal is a pig. Some animals, such as rats and pigs, have higher cognitive functions and more complex behaviors than mice, which is advantageous for the study of Angelman Syndrome. Such animals can also provide more materials (brain tissues, blood, etc.) for research than a mouse.

Optionally, animals of the invention may be evaluated to verify the absence of UBE3A production, including any isoform. Methods for detecting proteins may be used, such as immunoassays (e.g., ELISA, immunocytochemistry, Western blot) and mass spectrometry.

Optionally, animals of the invention may be evaluated to verify the presence of a phenotype that is useful for modeling Angelman Syndrome. Tests to assess phenotype should be appropriate for the species of the animal. As described in more detail below, four major phenotypes that may be evaluated in the animal include, but are not limited to: seizure, motor coordination, learning and memory, and synaptic function.

Optionally, the genome of cells, or the genome of the animal, may have further modifications (beyond deletion of the Ube3a gene). Alternatively, the genome of cells, or the genome of the animal may have no further genetic modification.

The Ube3a gene is located within the q11-q13 region on chromosome 15 in humans while it is found on the proximal region of chromosome 7 in mice (T. Kishino and J. Wagstaff, "Genomic organization of the UBE3A/E6-AP gene and related pseudogenes," *Genomics*, vol. 47, no. 1, pp. 101-107, 1998).

Angelman Syndrome in humans can arise from any disruption to the maternal UBE3A allele. This includes uniparental disomy, deletion, and mutation (Fang P et al., *Human Molecular Genetics*, 1999, 8(1):129-135). Each of these naturally occurring situations can be replicated in an animal. The Ube3a-deficient animals of the invention may be produced using any technique that results in lack of an entire Ube3a gene. In some embodiments, clustered regularly interspaced short palindromic repeats (CRISPR) is used. CRISPR simplifies creation of animals for research that mimic disease or show what happens when a gene is knocked down or mutated. CRISPR may be used at the germline level to recreate animals where the gene is changed (in this case, deleted), or it may be targeted at non-germline cells, such as brain cells (van Erp P B et al., *Current Opinion in Virology*, 2015, 12:85-90; Maggio I et al., *Trends in Biotechnology*, 2015, 33(5):280-291; Rath D et al., *Biochimi*, 2015, 117:119-128; and Freedman B S et al., *Nature Communications*, 2015, 6:8715, which are each incorporated herein by reference in their entirety).

The Ube3a gene can be knocked out using any method known in the art (e.g., homologous recombination). For example, knocking out the Ube3a gene can comprise deleting the gene from a genome of a non-human cell or animal.

The knockout can be accomplished with a plasmid, a bacterial artificial chromosome or other DNA construct, and proceeding to cell culture. Individual cells are genetically transfected with the DNA construct. Embryonic stem cells are genetically transformed and inserted into early embryos. Resulting animals with the genetic change in their germline cells can then pass the gene knockout to future generations.

It is also contemplated that knocking out the gene can include replacing the Ube3a gene in a genome with one or more nucleotides. Knocking out one or more genes can also comprise inserting a sequence in one or more genes thereby disrupting expression of the one or more genes. For example, inserting a sequence can generate a stop codon in the middle of one or more genes. Inserting a sequence can also shift the open reading frame of one or more genes.

The knockout can be done in any cell, organ, and/or tissue in a non-human animal. For example, the knockout can be a whole body knockout, e.g., expression of the Ube3a gene is eliminated in all cells of a non-human animal. The knockout can also be specific to one or more cells, tissues, and/or organs of a non-human animal. This can be achieved by conditional knockout, where expression of the Ube3a gene is selectively eliminated in one or more organs, tissues or types of cells. A conditional knockout can be performed by a Cre-lox system, where cre is expressed under the control of a cell, tissue, and/or organ specific promoter. For example, the Ube3a gene can be knocked out in one or more tissues, or organs, where the one or more tissues or organs can include brain, lung, liver, heart, spleen, pancreas, small intestine, large intestine, skeletal muscle, smooth muscle, skin, bones, adipose tissues, hairs, thyroid, trachea, gall bladder, kidney, ureter, bladder, aorta, vein, esophagus, diaphragm, stomach, rectum, adrenal glands, bronchi, ears, eyes, retina, genitals, hypothalamus, larynx, nose, tongue, spinal cord, or ureters, uterus, ovary, testis, and/or any combination thereof. Ube3a can also be knocked out in one types of cells, where one or more types of cells include trichocytes, keratinocytes, gonadotropes, corticotropes, thyrotropes, somatotropes, lactotrophs, chromaffin cells, parafollicular cells, glomus cells melanocytes, nevus cells, merkel cells, odontoblasts, cementoblasts corneal keratocytes, retina muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, Enterochromaffin-like cells, gastric chief cells, parietal cells, foveolar cells, K cells, D cells, I cells, paneth cells, enterocytes, microfold cells, hepatocytes, hepatic stellate cells (e.g., Kupffer cells from mesoderm), cholecystocytes, centroacinar cells, pancreatic stellate cells, pancreatic .alpha. cells, pancreatic .beta. cells, pancreatic .delta. cells, pancreatic F cells, pancreatic cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, and/or any combination thereof.

Conditional knockouts can be inducible, for example, by using tetracycline inducible promoters, development specific promoters. This can allow for eliminating or suppressing expression of a gene/protein at any time or at a specific time. For example, with the case of a tetracycline inducible promoter, tetracycline can be given to a non-human animal any time after birth. If a non-human animal is a being that develops in a womb, then the promoter can be induced by giving tetracycline to the mother during pregnancy. If a non-human animal develops in an egg, a promoter can be induced by injecting, or incubating in tetracycline. Once tetracycline is given to a non-human animal, the tetracycline will result in expression of cre, which will then result in excision of a gene of interest (Ube3a).

A cre/lox system can also be under the control of a developmental specific promoter. For example, some promoters are turned on after birth, or even after the onset of puberty. These promoters can be used to control cre expression, and therefore can be used in developmental specific knockouts.

It is also contemplated that any combination of knockout technology can be utilized. For example, tissue specific knockout can be combined with inducible technology, creating a tissue specific, inducible knockout. Furthermore, other systems such developmental specific promoter, can be used in combination with tissues specific promoters, and/or inducible knockouts.

Knocking out technology can also comprise gene editing. For example, gene editing can be performed using a nuclease, including CRISPR associated proteins (Cas proteins, e.g., Cas9), Zinc finger nuclease (ZFN), Transcription Activator-Like Effector Nuclease (TALEN), and maganucleases (see, for example, Unniyampurath U, R Pilankatta, and M Krishnan "RNA Interference in the Age of CRISPR: Will CRISPR Interfere with RNAi?", *International Journal of Molecular Sciences,* 2016, 17:291; Boettcher M and M T McManus, Choosing the Right Tool for the Job: RNAi, TALEN, or CRISPR, *Mol Cell,* 2015; 58(4):575-585; Carlson D F et al., "Efficient TALEN-mediated Gene Knockout in Livestock," *PNAS,* 109(43):17382-17387; and Heidenreich M and F. Zhang, "Applications of CRISPR-Cas Systems in Neuroscience," 2016, 17:36-44, which are each incorporated herein by reference in their entireties).

Nucleases can be naturally existing nucleases, genetically modified, and/or recombinant. For example, a CRISPR/cas system can be used as a gene editing system.

It is also contemplated that less than all alleles of the Ube3a gene be knocked out. For example, in diploid non-human animals, it is contemplated that one of two alleles are knocked out. However, it is also contemplated that all alleles of the Ube3a gene be knocked out.

Knocking out of the Ube3a gene can be validated by genotyping. Methods for genotyping can include sequencing, restriction fragment length polymorphism identification (RFLPI), random amplified polymorphic detection (RAPD), amplified fragment length polymorphism detection (AFLPD), PCR (e.g., long range PCR, or stepwise PCR), allele specific oligonucleotide (ASO) probes, and hybridization to DNA microarrays or beads. For example, genotyping can be performed by sequencing. In some cases, sequencing can be high fidelity sequencing. Methods of sequencing can include Maxam-Gilbert sequencing, chain-termination methods (e.g., Sanger sequencing), shotgun sequencing, and bridge PCR. In some cases, genotyping can be performed by next-generation sequencing. Methods of next-generation sequencing can include massively parallel signature sequencing, polony sequencing, pyrosequencing (e.g., pyrosequencing developed by 454 Life Sciences), single-molecule real-time sequencing, Ion semiconductor sequencing (e.g., by Ion Torrent semiconductor sequencing), sequencing by synthesis (e.g., by Solexa sequencing by Illumina), sequencing by ligation (e.g., SOLiD sequencing by Applied Biosystems), DNA nanoball sequencing, and heliscope single molecule sequencing. In some cases, genotyping of a non-human animal herein can comprise full genome sequencing analysis. In some cases, knocking out of a Ube3a gene in an animal can be validated by sequencing (e.g., next-generation sequencing) a part of the gene or the entire gene.

Another aspect of the invention concerns a method for assessing the effect of an agent on an animal model, or isolated cell, tissue, or organ isolated from the animal model, the method comprising exposing an animal of the invention to an agent; and determining the presence or absence of one or more effects on the animal, cell, tissue, or organ. The effect of the agent on one or more physiological and/or behavioral parameters associated with Angelman Syndrome may be determined, e.g., by comparing relevant parameters before and after exposure to the candidate agent. Furthermore, various metabolic studies concerning the delivery and bioavailability of the agent may be determined. Thus, the potential efficacy of the agent in treating Angelman Syndrome and potential adverse effects may be evaluated in the animal, cell, tissue, or organ.

The cell, tissue, or organ may be isolated from any region of the animal. In some embodiments, the cell is a brain cell or neural cell. In some embodiments, the tissue is brain tissue. In some embodiments, the organ is the brain.

It is expected that the animals of the invention will replicate features of Angelman Syndrome including cognitive and motor deficits, and will provide insight in understanding the pathogenic mechanism of the disease, as well as a useful tool for identifying and validating potential interventions for the disorder. Clinical features of Angelman Syndrome such as cognitive and motor deficits, sleep disturbance, feeding difficulties, EEG pattern, and altered synaptic plasticity, and their molecular or electrophysiological correlates may be evaluated in the animals of the invention before, during, and after exposure to potential therapeutic agents. The animals may be used to screen substances for therapeutic activity for treatment of Angelman Syndrome and other neurological disorders or conditions such as traumatic brain injury and stroke, and to identify potential adverse effects.

In determining effects of the candidate agent on the animal, various parameters and biomarkers associated with Angelman Syndrome may be evaluated to identify improvement, worsening, or no change. For example, general locomotor activity and function may be characterized. Motor function may be examined via the accelerating rotarod task, grip strength, and gait analysis in order to evaluate potential changes in motor coordination deficits. Learning and memory-related tasks may be performed in order to determine if there are differences in spatial learning (Morris water maze), working memory (T, Y, or radial arm maze), object recognition memory (novel object recognition), or associative learning (fear conditioning). Coinciding with differences in memory, hippocampal synaptic plasticity may be evaluated in the animal, including basal synaptic activity, presynaptic function, and post-synaptic responses to tetanic stimulation (long-term potentiation and depression). Anxiety and sensorimotor gating can be evaluated using the elevated plus maze/rat social interaction test and prepulse inhibition, respectively.

Four major phenotypes that may be evaluated in the animal include, but are not limited to: seizure, motor coordination, learning and memory, and synaptic function:
1) Seizure: seizure propensity may be evaluated using an audiogenic test with white noise.
2) Motor coordination: gait, balance and motor learning may be evaluated using open field, rotorod and grip strength tests.
3) Learning and memory: spatial and associative learning may be evaluated using the hidden platform water maze and fear conditioning tests.
4) Synaptic function: baseline synaptic transmission, short- and long-term potentiation may be determined using hippocampal field electrophysiology.

Any candidate agent may be assessed using the animal, cells, tissues, organs, and methods of the invention. The agents may be a substance such as small synthetic or naturally derived organic compounds, nucleic acids, polypeptides, antibodies, fragments, isoforms, variants, or other materials that may be used independently for such purposes. For example, an agent may be a small molecule (e.g., a small organic molecule). In some embodiments, an agent is a prodrug, derivative, analog of another compound. An agent may include a pharmaceutically acceptable carrier, excipient, and/or diluent. In some embodiments, an agent is in an isolated or purified state. In some embodiments, the agent comprises a small molecule, polypeptide, or nucleic acid. In some embodiments, the agent is a peptidomimetic. In some embodiments, the agent is a nucleic acid encoding polypeptide, such as a corrective Ube3a gene (e.g., a potential gene therapy). In some embodiments, the agent is a nucleic acid that inhibits expression of a gene (e.g., RNAi molecule such as siRNA or shRNA, antisense oligonucleotide, etc.). Nucleic acids may be administered in naked form, in plasmids, or in viral vectors (e.g., lentivirus, adeno-associated virus, etc.) or non-viral vectors (e.g., cationic lipid).

In some embodiments, the agent is a chemotherapeutic agent, such as a topoisomerase inhibitor (e.g., topotecan). In some embodiments, the agent is an artificial transcription factor (see, for example, Bailus et al., 2016 [2], which is incorporated herein by reference in its entirety). In some embodiments, the agent comprises an anti-seizure anticonvulsant agent (e.g., anti-epileptic drug (AED)), such as diazepam or midazolam.

In some embodiments, the agent is one that decreases neuronal excitation, such as by blockade of sodium channels (e.g., brivaracetam or other levetiracetam analogue, carisbamate (RWJ 333369)) or by inhibition of glutamate release/AMPA antagonism (e.g., NS 1209, BGG 492), or that enhances neuronal inhibition, such as ganalaxone, stiripentol, CPP 115 or other analogue of vigabatrin, or valrocemide or other derivative of valproic acid. In some embodiments, the agent is an anti-inflammatory agent such as belnacasan (e.g., VX 765), a prodrug of valproic acid (e.g., SPD 421, valnoctamide), potassium channel modulator (e.g., YKP 3089, ICA 105665), melatonin, a 5HT receptor agonist (e.g., naluzotan), or Na—K-2Cl co-transporter inhibitor such as bumetanide. In some embodiments, the agent comprises a PSD-95/PDZ-binding cyclic peptide, such as CN2097.

Optionally, agents may be coupled to a cell-penetrating peptide (CPP), such as the transduction domain of the HIV-transactivator protein (TAT), to facilitate cellular intake and/or delivery to the brain.

Optionally, agents may be coupled to a detectable moiety, such as a fluorescent protein, to permit imaging and visualization of the agent after it is brought into contact with the cell, tissue, organ, or animal.

The agent and the isolated cell, tissue, or organ, may be brought into contact in vitro or ex vivo, or the agent may be administered to the animal in vivo by any route effective in delivering the agent to the desired anatomical location or locations. Examples of routes of administration, devices and equipment, vehicles and formulations that may be utilized are provided in Turner P V et al., "Administration of Substances to Laboratory Animals: Routes of Administration and Factors to Consider, *Journal of the American Association for Laboratory Animal Science*, September 2011, 50(5):600-613; and Turner P V et al., "Administration of Substances to Laboratory Animals: Equipment Considerations, Vehicle Selection, and Solute Preparation, *Journal of the American Association for Laboratory Animal Science*, September 2011, 50(5):614-627, which are each incorporated herein by reference in their entireties.

Administration of agents may be enteral or parenteral. In some embodiments, the agent is administered systemically. In some embodiments, the agent is administered locally. In some embodiments, the agent is administered to the subject by a route selected from the group consisting of intravascular (e.g., intravenous or intra-arterial), intracranial, intrathecal, epidural, intraperitoneal, intramuscular, intracutaneous, oral, intragastric via gavage, intranasal, intratracheal, inhalational, intra-ocular, intrathoracic, intracardiac, topical, rectal, subcutaneous, intradermal, and transdermal.

In some embodiments, the agent is administered by infusion. In some embodiments, the animal ingests the agent (e.g., as a dietary supplement, as an additive in food and/or drinking water, etc.). The agent brought into contact with the cell, tissue, or organ, or administered to the animal, may be a combination of agents within the same composition or separate compositions, and brought into contact with the animal simultaneously or consecutively.

The animal may be on a standard diet, or non-standard diet, such as a ketogenic diet.

Optionally, the animal may have one or more other genetic modifications. Polynucleotides (e.g., genes) may be over-expressed or under-expressed (e.g., knocked out) in the animal.

Optionally, the animal may have no further genetic modifications.

Animals with various genetic backgrounds are known in the art and may be utilized to produce an animal of the invention, such as BALB substrains (e.g., CByJ.Cg-Foxn1$^{nu}$/J, or CBySmn.CB17-Prkdc$^{scid}$/J), C57BL/6J (e.g., B6; 129S7-Rag1$^{tm1Mom}$J, B6.129 S7-Rag1$^{tm1Mom}$/J, or B6.CB17-Prkdc$^{scid}$/SzJ), NOD/LtSzJ (e.g., NOD.129S7 (B6)-Rag1$^{tm1Mom}$/J, NOD.Cg-Rag1$^{tm1Mom}$Prf1$^{tm1Sdz}$/Sz, NOD.CB17-Prkdc$^{scid}$/SzJ, NOD.Cg-Prkdc$^{scid}$B2m$^{tm1Unc}$/J or NOD.Cg-Prkdc$^{scid}$Il2rg$^{tm1Wjlc}$/SzJ), and NU/J (The Jackson Laboratory, Bar Harbor, Me.). The animals may be immune-competent or immune-deficient.

EXEMPLIFIED EMBODIMENTS

Embodiment 1

A non-human animal comprising cells having a genome that is lacking an entire E3 ubiquitin ligase (Ube3a) gene.

Embodiment 2

The animal of embodiment 1, wherein the animal exhibits one or more physiological and/or behavioral features associated with Angelman Syndrome.

Embodiment 3

The animal of embodiment 1 or 2, wherein the animal is a mammal.

Embodiment 4

The animal of embodiment 3, wherein the mammal is a rodent.

Embodiment 5

The animal of embodiment 4, wherein the rodent is a rat.

Embodiment 6

The animal of embodiment 3, wherein the mammal is a pig.

Embodiment 7

The animal of any one of embodiments 1 to 6, wherein the genome of the cells has a further genetic modification.

Embodiment 8

The animal of any one of embodiments 1 to 6, wherein the genome of the cells has no further genetic modification.

Embodiment 9

A cell, tissue, or organ isolated from the animal of any one of embodiments 1 to 8.

Embodiment 10

A method for assessing the effect of an agent on an animal model, comprising exposing the animal of any one of embodiments 1 to 8, or the cell, tissue, or organ of embodiment 9, to the agent; and determining an effect of the agent on the animal, cell, tissue, or organ.

Embodiment 11

The method of embodiment 10, wherein the agent comprises of combination of two or more agents, and wherein the animal is exposed to the combination of agents simultaneously or consecutively.

Embodiment 12

The method of embodiment 10, wherein the agent comprises a small molecule, polypeptide, or nucleic acid.

Embodiment 13

The method of any one of embodiments 10-12, wherein said exposing comprises administering the agent to the animal by a route selected from the group consisting of intravascular (e.g., intravenous or intra-arterial), intracranial, intrathecal, epidural, intraperitoneal, intramuscular, intracutaneous, oral, intragastric via gavage, intranasal, intratracheal, inhalational, intra-ocular, intrathoracic, intracardiac, topical, rectal, subcutaneous, intradermal, and transdermal.

Embodiment 14

The method of any one of embodiments 10-13, wherein the animal ingests the agent.

Embodiment 15

The method of any preceding embodiment, wherein said determining comprises determining the effect of the agent on one or more physiological and/or behavioral parameters associated with Angelman Syndrome.

Embodiment 16

The method of embodiment 1415 wherein the one or more parameters comprises one or more from among seizure, motor coordination, learning, memory, and synaptic function.

Definitions

As used in this specification, the singular forms "a", "an", and "the" include singular and plural reference unless the context clearly dictates otherwise. Thus, for example, a reference to "a compound" includes a single compound and more than one such compound. A reference to "an agent" is inclusive of a single agent or more than one agent. Reference to "cell" is inclusive of a single cell and more than one such cell. A reference to "a treatment" includes a single treatment and more than one such treatment, and so forth.

As used herein, the term "administration" is intended to include, but is not limited to, the following delivery methods: intravascular (e.g., intravenous or intra-arterial), intracranial, intrathecal, epidural, intraperitoneal, intramuscular, intracutaneous, oral, intragastric via gavage, intranasal, intratracheal, inhalational, ocular, intrathoracic, intracardiac, topical, rectal, subcutaneous, intradermal, and transdermal. Administration can be local at a particular anatomical site, or systemic.

The term "agent", as used herein, refers to all materials that may be used as or in a pharmaceutical composition, or that may be a compound such as small synthetic or naturally derived organic compounds, nucleic acids, polypeptides, antibodies, fragments, isoforms, variants, or other materials that may be used independently for such purposes. For example, an agent may be a small molecule (e.g., a small organic molecule). In some embodiments, an agent is a prodrug, derivative, analog of another compound. An agent may include a pharmaceutically acceptable carrier, excipient, and/or diluent. In some embodiments, an agent is in an isolated or purified state.

The term "animal," as used herein, refers, unless specifically indicated otherwise, to any non-human animal, including, but not limited to, vertebrates such as mammals, non-mammals, domesticated animals (e.g., cows, sheep, cats, dogs, horses, pigs), primates (e.g., non-human primates such as monkeys), rabbits, fish, rodents (e.g., mice, rats, hamsters, guinea pigs), and non-vertebrates (e.g., *Drosophila melanogaster* and *Caenorhabditis elegans*). The terms "rodent" and "rodents" refer to all members of the phylogenetic order Rodentia (e.g., mice, rats, squirrels, beavers, woodchucks, gophers, voles, marmots, hamsters, guinea pigs, and agoutas) including any and all progeny of all future generations derived therefrom. The term "murine" refers to any and all members of the family Muridae, including without limitation, rats and mice. In some embodiments of the invention, the Ube3a gene is the rat gene and the animal is a rat. In some embodiments of the invention, the Ube3a gene is the pig gene and the animal is a pig. The animal may be of any life stage, e.g., embryonic, infant, adolescent, or adult, and any gender. In some embodiments, the animal is female. In some embodiments, the animal is male. The invention encompasses the various generations of progeny of animals in which the Ube3a gene deficiency is initially made.

The terms "comprising", "consisting of" and "consisting essentially of" are defined according to their standard meaning. The terms may be substituted for one another throughout the instant application in order to attach the specific meaning associated with each term.

The term "exposing", as used herein, in the context of exposing an animal, cell, tissue, or organ to an agent, refers to the act of bringing into contact an agent and an animal, cell, tissue, or organ, for any duration, in a manner that allows evaluation of one or more effects of the agent on the animal, cell, tissue, or organ. For example, one or more agents may be delivered (administered) to an animal by various administration routes, such as topical, oral, parenteral, subcutaneous, transdermal, transbuccal, intravascular (e.g., intravenous or intra-arterial), intrathecal, intramuscular, subcutaneous, intranasal, and intra-ocular, etc.

The terms "isolated" or "biologically pure" refer to material that is substantially or essentially free from components which normally accompany the material as it is found in its native state. Thus, isolated cells in accordance with the invention preferably do not contain materials normally associated with the cells in their in situ environment. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide).

The term "small molecule" refers to a composition that has a molecular weight of less than about 3 kilodaltons (kDa), less than about 1 kDa, or less than about 1 kDa. Small molecules may be nucleic acids, peptides, polypeptides, peptidomimetics, carbohydrates, lipids, or other organic (carbon-containing) or inorganic molecules. A "small organic molecule" is an organic compound (or organic compound complexed with an inorganic compound (e.g., metal), that has a molecular weight of less than about 3 kDa, less than about 1.5 kDa, or less than about 1 kDa.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

All patents, patent applications, provisional applications, and publications referred to or cited herein are incorporated by reference in their entireties, including all figures and tables, to the extent they are not inconsistent with the explicit teachings of this specification.

Following is an example that illustrates procedures for practicing the invention. The example should not be construed as limiting. All percentages are by weight and all solvent mixture proportions are by volume unless otherwise noted.

Example 1—Production of Ube3a-Deficient Rat

Two different alleles of the deletion were produced: del90457/ins8 and del90476/ins1. Founder animals were born, followed by F1 progeny, and genetic transmission of the deletion to the F1 progeny was confirmed.

Figure 1:
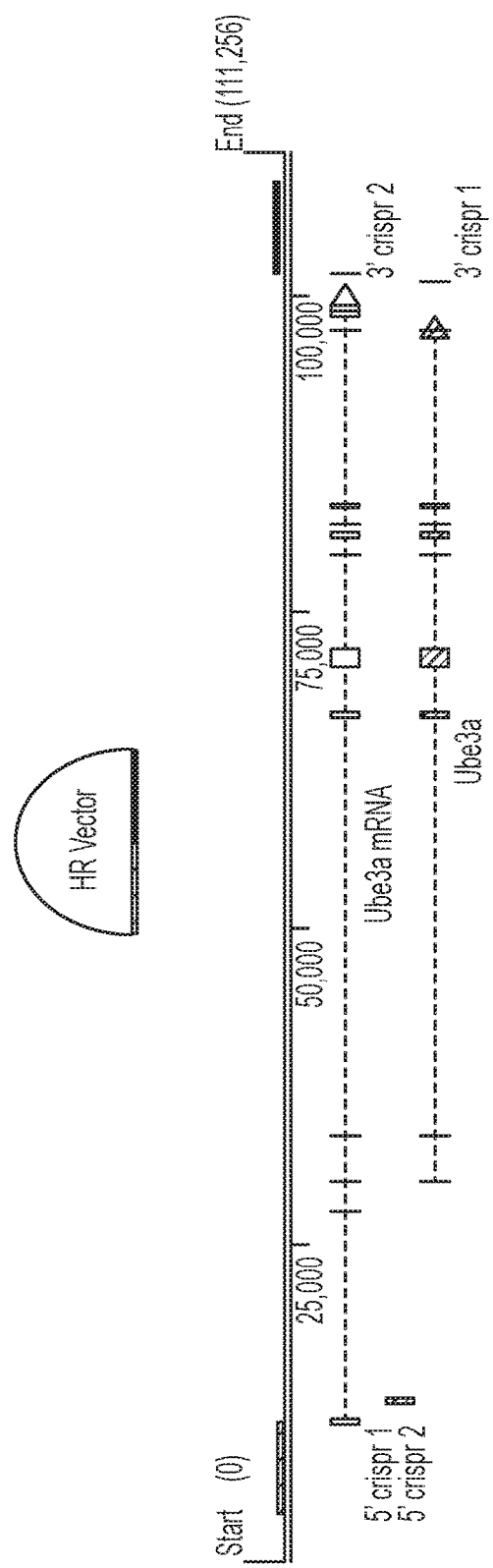
FIG. 1 is a schematic showing the sites of CRISPR design and size of the Ube3a deletion.

FIG. 1 is a schematic showing the sites of CRISPR design and size of the Ube3a deletion. Four CRISPR guide RNAs were designed. Specifically, two each to areas that flank the entire Ube3a genomic region. The production of these specific CRISPR sites were to effectively delete approximately 90 kb of genomic sequence. An additional vector that contained arms of homology that spanned the region to be deleted was also included in order to facilitate the deletion.

```
Reagent Design & Production:
5' CRISPR-1 Target site
                              (SEQ ID NO: 11)
GGCCCTGCAGAGATGCAATC 5' CRISPR-2 Target site
                              (SEQ ID NO: 12)
GGAGCCCTCCGCCGGCA 3' CRISPR-1 Target site
                              (SEQ ID NO: 13)
TACCCTTCCCAGGCCCC 3CRISPR-2 Target site
                              (SEQ ID NO: 14)
GCATTTCTAGTACATCATCC
```

Founder Screening:

Screening for the deletion was performed by isolation of genomic DNA and probing with primers (shown below) that span the deleted region. These primers will anneal upstream of the 5' most CRISPR cut site and downstream of the 3' most CRISPR cut site. The size depends on the nature of the deletion/integration.

TABLE 1

| Primers spanning deleted region | | |
|---|---|---|
| Ub3aDelF1 | AACACCAAGCCTCTCTCAGC (SEQ ID NO: 15) | 500-920 bp |
| Ub3aDelR1 | ACCAGGCCTCAAAATTGACA (SEQ ID NO: 16) | |
| Ub3aDelF2 | CTCCCGAGTACACCGAAGAC (SEQ ID NO: 17) | |
| Ub3aDelR2 | GGGAACAGCAAAAGACATGG (SEQ ID NO: 18) | |

Rat pups positive for the above PCR were further analyzed using primers that span the deleted region and anneal outside of the arms of the vector. Only pups that had deleted the entire 90 kb would show amplification. WT gDNA is used as a control (FIG. 2).

TABLE 2

| Primers spanning deleted region and annealing outside of vector arms | | |
|---|---|---|
| Ub3aDelSpcfcF3 | GTACCAAGAAGTCACATGGCTC (SEQ ID NO: 19) | 1869 bp |
| Ub3aDelSpcfcR3 | GCAGGCTGCTATTACACTAAGGA (SEQ ID NO: 20) | |
| Ub3aDelSpcfcF4 | ACATGGCTCTAAAAGAGTTCAGG (SEQ ID NO: 21) | 1875 bp |
| Ub3aDelSpcfcR4 | GTGATTCACTAGGGATATGCAGG (SEQ ID NO: 22) | |

Figure 2:
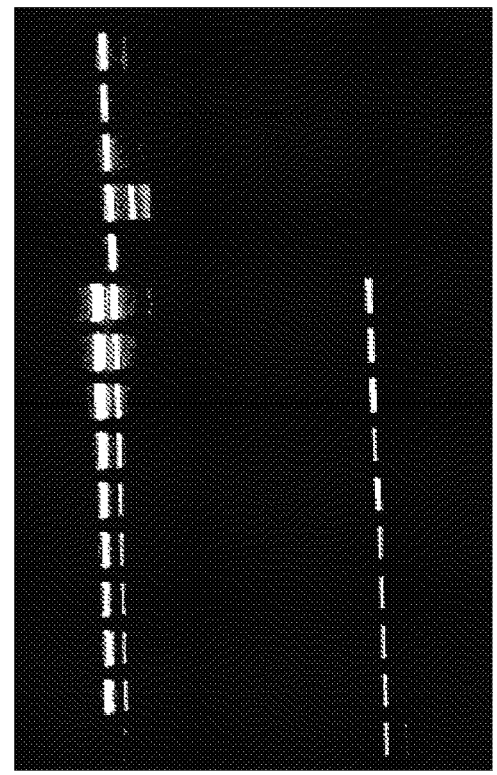
FIG. 2 is a gel showing the approximate size (depending on allele) of 900 bp (for AS band), 400 bp (for WT band); Cycling: 95 deg-30 sec/59 deg-45 sec/72 deg-1.5 minute/35 cycles.

FIG. 2 is a gel showing the approximate size (depending on allele) of 900 bp (for AS band), 400 bp (for WT band); Cycling: 95 deg-30 sec/59 deg-45 sec/72 deg-1.5 minute/35 cycles.

As rats tend to have developed increased behavioral complexity compared to mice, similar improvements in learning and memory, social, and motor-related tasks, are expected, but potentially to a greater extent. It is likely that changes similar to Angelman syndrome in learning, motor, seizure, and social/anxiety-related tasks will be observed.

General locomotor activity and function will be characterized, using an open field test. Additionally, motor function will be examined via the accelerating rotarod task, grip strength, and gait analysis in order to evaluate potential motor coordination deficits. Learning and memory-related tasks will be performed in order to determine if there are differences in spatial learning (Morris water maze), working memory (T, Y, or radial arm maze), object recognition memory (novel object recognition), or associative learning (fear conditioning). Coinciding with differences in memory, hippocampal synaptic plasticity will be evaluated in the rat, including basal synaptic activity, presynaptic function, and post-synaptic responses to tetanic stimulation (long-term potentiation and depression). Anxiety and sensorimotor gating can be evaluated using the elevated plus maze/rat social interaction test and prepulse inhibition, respectively.

There are 4 major phenotypes that will be evaluated in the rat:

1) Seizure. Seizure propensity will be evaluated using an audiogenic test with a 120 dB white noise.
2) Motor coordination. Gait, balance and motor learning will be evaluated using open field, rotorod and grip strength tests.
3) Learning and memory. Spatial and associative learning will be evaluated using the hidden platform water maze and fear conditioning tests.
4) Synaptic function. Baseline synaptic transmission, short- and long-term potentiation will be determined using hippocampal field electrophysiology.

Example 2—Imprinting of Ube3a in Early Life Resiliency Due to Augmented Maternal Care While genetic and environmental risk factors for mental health disorders are highly investigated, the biological underpinnings of long-lived resilience from early life experience are poorly understood. Epigenetic mechanisms such as DNA methylation and noncoding RNA act at the interface of genetic and environmental risk and protective factors for developing mental health disorders. Parental imprinting is an epigenetic inheritance pattern characterized by parent-of-origin differences in DNA methylation, chromatin, and gene expression. Imprinting is hypothesized to be an adaptive mechanism predominantly in mammalian species to promote maternal investment in offspring. Understanding imprinting and other epigenetic mechanisms establishing resilience in early life could result in the development of diagnostic tools and treatments targeted to children with adverse early life experiences to prevent life-long mental health problems. This work utilizes a rat model of augmented maternal care to test the hypothesis that maternal care in early life interacts with cross-regulatory imprinted gene networks involving the maternally expressed ubiquitin E3 ligase gene Ube3a in postnatal neurons. Increased hypothalamic Ube3a expression induced by augmented maternal care within the first week of life corresponds to genome-wide alterations to DNA methylation, as well as other imprinted genes and miRNAs. The proposed experiments will test the hypothesis that paternally expressed noncoding transcripts regulating Ube3a expression and isoform usage in early postnatal neurons are central to the global methylation and transcriptional differences in the hypothalamus resulting from augmented maternal care. Hypothalamus samples from a novel Ube3a deletion rat model will be investigated by molecular analyses of the coding and noncoding isoforms of Ube3a selectively from the maternal or paternal alleles. Genome-wide analyses will investigate the effects of Ube3a deletion and maternal care on methylation and transcription. Behavioral analyses will compare rats with paternal Ube3a deletion to wild-type rats with or without augmented maternal care. In addition, an artificial transcription factor that modulates paternal expression of Ube3a through inhibition of the noncoding antisense transcript will be tested as a potential modulator of the behaviors resulting from suboptimal maternal care in early life. Sex differences will be directly investigated in the proposed experiments and are expected in epigenetic mechanisms, behavioral tests, and response to treatment. Results from these studies are expected to improve understanding of the nature of resilience acquired from early life maternal care at the whole genome level and uncover the role of epigenetic regulators, including Ube3a and noncoding RNAs, in the process of establishing epigenetic marks of early life experience.

Mental health disorders are increasingly common, debilitating, and costly to the US population. Prevention and preemptive interventions are the most straightforward and least costly solutions, but understudied compared to risk assessments. This proposal utilizes a rat model of enhanced maternal care that results in alterations in genes regulating stress pathways in hypothalamus in early life, which affect resilience to stress and improved memory throughout life. This experience-dependent, resilience rat model will enable the molecular understanding of specific gene pathways in the hypothalamus in response to this protective pathway. In addition, this study proposes a treatment strategy in young rat pups to determine if suboptimal maternal care in early life could be corrected by modulating Ube3a expression in young rats. Furthermore, the results from these studies will be comparable to human genetic studies from psychiatric disorders, gene pathway and drug target databases, as well as existing epigenome roadmaps for translational relevance to human mental health.

Mental health disorders are estimated to affect an average of 20% of the US population, with the highest rate observed at young adulthood. The risk factors for mental health disorders are numerous and involve complex interactions between genes, environment, psychosocial stress, and development, with a particularly sensitive window in early life. Males and females have differing rates of mental health disorders, including anxiety, depression, schizophrenia, and bipolar disorders, but the reasons for sex differences in response to similar stressors are poorly understood. Epigenetic mechanisms represent a potential unifying convergence at the interface of genetic and environmental factors determining a person's state of mental health because they can explain how early life environment and experiences are encoded on top of one's DNA. Since epigenetic marks are tissue-dependent and human brain is not accessible, progress in identifying epigenetic pathways relevant to risk and resilience for psychiatric conditions or sex differences in mental health has been limited.

Imprinting is an epigenetic mechanism that selectively marks maternal and paternal alleles of specific genes based on DNA methylation and chromatin marks established in the gametes. Imprinting has evolved within mammals from either a conflict or coadaptation between the differing interests of paternal and maternal genomes [16,17]. The paternal genome is predicted to direct the extraction of maternal resources, both in utero and as directed maternal care of offspring in early postnatal life [18-20]. How specific imprinted genes or paternal-maternal co-adaptive mechanisms influence stress resilience acquired in early life is currently unexplored.

The long-term goal of this work is to prevent and develop preemptive interventions for mental health disorders through an approach that integrates protective gene transcription patterns acquired early in life with molecular mechanisms leading to long-term changes in behavior. A well-established rat model of augmented maternal care (AMC) is utilized in which experimenter handling of pups for 15 min per day from postnatal days 2-8 (P2-P8) increases the quality and quantity of maternal care behaviors in response to the separation, resulting in long-lived differences in stress resiliency and cognition in the offspring compared to non-handled pups [11-15]. Standard undisturbed rat housing can therefore be considered poor conditions for maternal care, perhaps equivalent to a human single mother confined alone with her newborn baby, without support or life options.

To investigate AMC-related epigenetic changes within the hypothalamic-pituitary-adrenal (HPA) axis, a genome-wide screen of hypothalamic genes demonstrated significant and reproducible changes in imprinted genes, including Ube3a, encoding a E3 ubiquitin ligase implicated in multiple human disorders [1]. A global reduction in DNA methylation was also observed in the P9 hypothalamus in AMC compared to control pups, consistent with observed results in UBE3A duplications in human brain and neurons [5,6]. It is proposed that the transition from biallelic to imprinted expression of Ube3a in neurons within the first week of life [21-23] is mechanistically involved in the experience-dependent acquisition of AMC resiliency. The aims proposed herein seek to fill critical gaps in knowledge about the Ube3a isoforms expressed from the maternal versus paternal alleles in the early postnatal hypothalamus in response to the AMC experience.

A first objective (Aim 1) is to investigate augmented maternal care effects on imprinted expression of Ube3a and the downstream impacts of altered UBE3A levels on transcription and methylation genome-wide. This will test the hypothesis that the maternal versus paternal alleles of Ube3a differentially express noncoding transcripts and protein isoforms of Ube3a/UBE3A in response to handling from P2 to P8. Since increased UBE3A in human neurons corresponds to large-scale DNA hypomethylation over synaptic genes [6], a pattern that was also observed in the hypothalamus in response to augmented maternal care, whole genome bisulfite sequencing will be performed and integrated with transcriptomic, in situ, and protein analyses.

A second objective (Aim 2) is to investigate the necessity of the paternal Ube3a allele in behavioral outcomes following AMC. To test the hypothesis that the paternally expressed noncoding RNAs and truncated protein isoforms of Ube3a/UBE3A are critical to the long-lasting behavioral outcomes from AMC, rat littermates will be bred to inherit either paternal Ube3a deletion or the wild-type allele and compared for response to P2-P8 handling in a series of behavioral tasks designed to test social, emotional, and cognitive measurements of resilience prior to adulthood. Tissues from littermates in these experiments will also be examined for molecular changes in Ube3a isoforms and genome-wide alterations to the transcriptome and DNA methylome.

A third objective (Aim 3) is to modulate paternal Ube3a expression in weanling rats who did not receive AMC from P2-P8. To test the hypothesis that therapeutic modulation of paternal Ube3a expression may mimic the effects of early life AMC, weanling rats (P9-P23) will be injected with an artificial transcription factor (ATF) that specifically increases paternal Ube3a by reducing antisense expression. Behavioral outcomes and molecular expression analyses will be performed on rats prior to adulthood, with or without handling, treated with either Ube3a or control ATF. The results of these experiments are expected to improve understanding of the dynamics of imprinted Ube3a isoforms on the establishment of resiliency in early life that could be beneficial for preventing or treating mental health problems in humans in the future.

A. Epigenetics and Imprinting in Human Neurodevelopment and Postnatal Neuronal Maturation The dynamic epigenome allows for varying degrees of regulation of the inherited and static genome. The methylation of CpG dinucleotides is the first layer of epigenetic modification that is orchestrated by DNA methyltransferases that "write" the methylome as well as methyl binding proteins that "read" the presence of methylated cytosines and recruit additional reader and writer protein complexes that further alter chromatin state and structure [24]. An additional layer of epigenetics comes post-transcriptionally through the influence of noncoding RNAs; miRNAs regulate transcript stability and long noncoding RNA alter chromatin structure [25].

Not surprisingly, dysfunctions in neuronal epigenetic processes lead to human disorders [26]. Hence, two well-characterized epigenetic mechanisms, parental imprinting and X chromosome inactivation, are involved in several autism-spectrum disorders, including Angelman (AS), Prader-Willi (PWS), 15q duplication (Dup15q), Rett, and Fragile-X syndromes [27]. In addition, epigenetic mechanisms such as DNA methylation can respond to environmental factors [28,29] and represent an important interface between genetic and environmental risk factors in complex mental disorders such as autism and schizophrenia [27,30-35]. Mutations in MECP2, encoding methyl CpG binding protein 2, an abundant nuclear protein involved in reading genome-wide DNA methylation patterns [36], prevent neuronal maturation in response to neuronal activity [37-39] and result in Rett syndrome [40].

Figure 3:
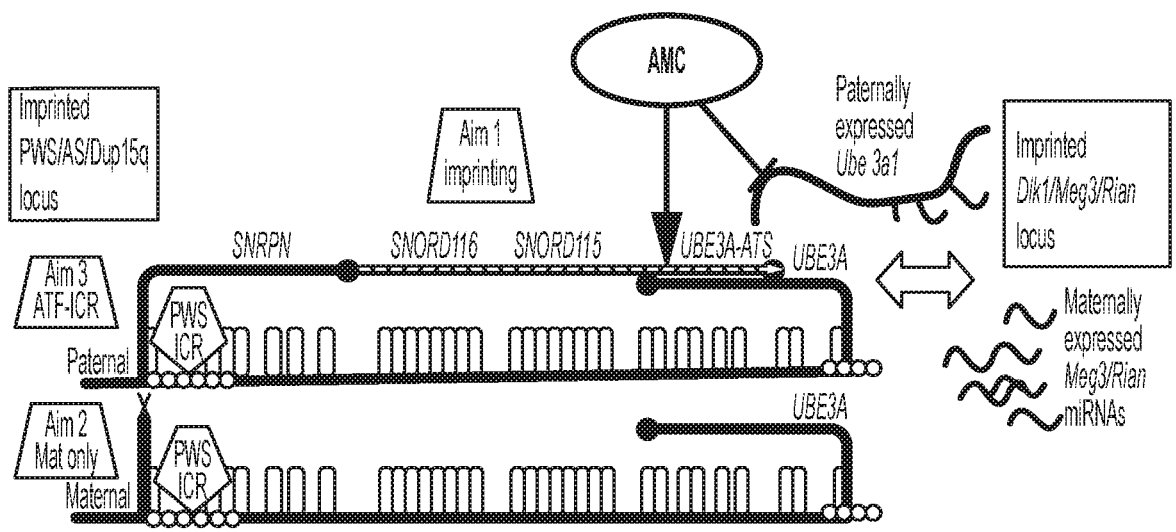
FIG. 3. Scientific premise and hypotheses. AMC is predicted to regulate paternal Ube3a expression and cross-talk between at least two imprinted loci. A first objective (Aim 1) will explore allelic expression patterns of multiple Ube3a isoforms following AMC, with the prediction that AMC promotes full length paternal Ube3a and reduces the Ube3a1 transcript with a unique 3'UTR that binds and blocks mi134 (Meg3/Rian locus) from promoting neuronal dendritogenesis. A second objective (Aim 2) will be to investigate the behavioral and molecular consequences of AMC in the absence of paternal Ube3a. A third objective (Aim 3) will be to modulate paternal Ube3a sense and antisense transcription to mimic AMC.

Imprinting is thought to have arisen as a specialized use of epigenetic mechanisms as either a conflict or cooperation between the paternal and maternal genomes in mammals [17,41,42]. Unlike the default state of biallelic expression, imprinted genes are selectively silenced on either the maternal or paternal allele by epigenetic differences including DNA methylation, noncoding RNAs, and repressive histone modifications. Imprinted genes are clustered in several discrete chromosomal locations and are usually regulated by a central imprinting control region (ICR), such as the PWS-ICR, in which methylation is diagnostic for AS, PWS, and Dup15q disorders (FIG. 3). Some imprinted genes exhibit tissue-specific or developmental-specific imprinting patterns regulated by long noncoding RNAs, such as the UBE3A-ATS which is specific to mature neurons [1,43]. Furthermore, the largest conserved cluster of microRNA (miRNA) in the mammalian genome is found within the Dlk1-Dio3 locus and is responsible for regulating neuronal maturation and growth pathways [44,45]. Experimental evidence is emerging for regulatory cross-talk between different imprinted gene loci [46-49], but how early postnatal maternal care influences the emerging "imprinted gene network" hypothesis [50-53] has not been previously explored.

B. The Promise of Behavioral Epigenetics for Prevention and Treatment of Mental Health Disorders Early life experiences in rodents and primates impart enduring effects on mental health and social behaviors into adulthood. Given that the early life experience of mammalian infants is primarily comprised of mother-infant interactions, maternal behavior paradigms have been used to investigate these issues. Maternal behavioral paradigms in rats have been best characterized by investigations of DNA methylation at the promoters of single candidate genes involved in the hypothalamic-pituitary-adrenal (HPA) responses that modulate corticosteroid stress responses in brain [54,55]. Natural variations in maternal care have been characterized by the amount of time rat dams spend licking and grooming (LG) pups and in the arched-back nursing (ABN) posture [56]. High frequency of LG and ABN behaviors results in increased serotonin activity, activation of cAMP-dependent kinases, and increased hippocampal transcription of nerve growth factor-inducible protein A (NGFI-A, encoded by Egr1) in the brains of developing offspring [57]. Early activation gene Egr1 was required for serotonin-induced DNA demethylation at the glucocorticoid receptor (GR) promoter [58].

Human studies have reinforced the usefulness of early life behavioral paradigms in rodents to uncover epigenetic changes relevant to human mental health. Depressed and anxious mothers have newborns with increased promoter methylation of the GR gene (NR3C1) in cord blood cells [59]. Postmortem hippocampus samples from suicide victims showed higher NR3C1 promoter methylation and reduced transcript levels in individuals with a history of childhood abuse [60].

An important caveat of maternal care studies is that genome-wide effects, which include imprinted gene networks and sex differences, have not been considered despite their importance. Genome-wide, the first year of human life is marked by age-correlated neuronal epigenomic changes of ~600 genes with reduced activating H3K4me3 marks in the prefrontal cortex, compared to ~100 genes with increased H3K4me3 during aging, highlighting the importance of early childhood for chromatin changes [61]. Although the effects of gonadal hormones on brain sexual differentiation has long been known [62], it is becoming clear this process is also independently influenced by sex chromosomes [63]. There is growing evidence that sex differences in epigenetic modifiers and modifications are established during normal neurodevelopment [64-66].

The ultimate promise of Behavioral Epigenetics is that adverse early life experiences of humans may be reversible through epigenetic therapy. Rodent studies have shown that treatment with the histone deacetylase inhibitor TSA in adulthood reversed the repressive histone and methylation marks and increased GR levels in the hippocampus [67]. The DNA methylation inhibitor Zebularine reversed the effects of maltreatment on Bdnf hypermethylation in adult rats [68]. However, the drugs used in these studies are not gene-specific and may have many deleterious side effects [69]. The challenge for future development of therapeutic reversals of epigenetic effects is to find specific targets for pharmacotherapy. Accordingly, it would be advantageous to develop preemptive interventions for mental health disorders using state-of-the-art epigenomic methodologies and novel hypotheses about imprinted gene network modulation in response to early life experiences.

C. Maternal UBE3A in Early Life Epigenetics, Oxidative Stress, and Neuronal Activity The E3 ubiquitin ligase protein UBE3A, also known as E6-AP, has a multitude of ascribed functions and targets relevant to human health and disease. Epigenetic regulation of the UBE3A locus by parentally imprinted noncoding transcription within human chromosome 15q11.2-q13.3 is responsible for the maternal-specific effects of 15q11.2-q13.3 deletion (AS) or duplication (Dup15q) disorders [1,43]. UBE3A is epigenetically silenced on the paternal allele in early postnatal neurons through a paternally encoded long transcript that initiates at the PWS imprinting control region and ends as an antisense transcript (UBE3A-ATS). Interestingly, while UBE3A is imprinted and expressed only from the maternal allele in most regions of the adult hypothalamus, within the superchiasmatic nucleus (SCN) region, UBE3A is also expressed from the paternal allele [70]. Despite the apparent escape from imprinting in some tissues, only maternally inherited Ube3a mutant mice show an apparent AS-like phenotype in adulthood [130, 131]. In addition to these imprinting effects, Ube3a expression is responsive to neuronal activity [71,72]. Ube3a is dynamically expressed from both parental alleles following membrane depolarization or glutamate treatment in cultured hippocampal neurons, or following a novel environment or fear conditioning in vivo [71,72]. Ube3a isoform 1 (Ube3a1, see FIGS. 3 and 7 diagrams), which utilizes an alternative polyadenylation site was also induced by social isolation in juvenile rat hippocampus [73]. From this study, the truncated Ube3a1 transcript was shown to act as a competitor noncoding RNA of activity-dependent miR134 that modulates dendritic growth [73]. Interestingly, miR134 is also parentally imprinted and localizes to a cluster of miRNAs downstream of the only other site of clustered snoRNAs in the mammalian genome that undergo neuron-specific chromatin decondensation (Dlk1/Gtl2/Meg3), similar to the PWS/AS locus [22]. Maternally deficient Ube3a mice show deficits in hippocampal synaptic plasticity and learning [71,74-76]. Defective GR receptor signaling was thought to be responsible for increased stress and anxiety in this AS mouse model [77], and non-genetic maternal effects on myelin and GR expression phenotypes were observed in both mutant and wild-type offspring of AS mice [78]. Furthermore, as a E3 ubiquitin ligase, expression of Ube3a is responsive to oxidative stress [79,80], and Ube3a deficient cells show impaired senescence in response to high doses of oxidative stress [81]. Together, these results implicate UBE3A as an epigenetic modulator of maternal genetic and environmental interactions during neuronal activity and stress responses in early postnatal life.

D. Augmented Maternal Care in Rats Models an Early Life Experience Leading to Resiliency In order to find epigenetic signatures of early life experiences relevant to human mental health, it is necessary to use an appropriate animal model that can be experimentally controlled to first identify genes and genetic pathways with distinct epigenomic signatures. Non-human primates show strong behavioral effects of early life stress and maternal care [82,83], but collecting brain samples from animal replicates is more expensive and time consuming than in rodents. Maternal care paradigms in rat are much more reproducible than in mouse, and the most common background for knockout mice (C57Bl6/J) have poor maternal care behaviors [84]. Also, rat brain is larger, rat litters are larger, and Sprague Dawley rats are genetically outbred, similar to humans, eliminating a problem with mouse strain specific behaviors. A robust behavioral paradigm in rats was chosen that is relevant to human early life experiences and to resilience for mental health disorders. Several rat models have demonstrated that the effects of early life experience such as maternal handling [85], separation [86,87], and maltreatment [88] have long lasting-effects on adult behavior.

The "handling" (augmented maternal care, AMC) paradigm has been characterized across five decades and replicated by several lab groups [11-15]. It is thought that the effects of handling on the brain and behavior are a consequence of the intensive increase in maternal care that occurs when dams are reunited with pups [89]. The repeated neonatal handling from P2 to P8 results in lifelong attenuation of the hypothalamic-pituitary-adrenal (HPA) axis responses to stressors. The release of corticotropin-releasing hormone (CRH) from the hypothalamic paraventricular nucleus (PVN), adrenocorticotropic hormone (ACTH) from the pituitary gland, and corticosterone from the adrenal glands are all attenuated following an acute stressor in the adult handled animals. The attenuation of Crh expression in the PVN occurs by the end of the neonatal handing procedure (P9) and lasts into adulthood. In contrast, handling-induced altered glucocorticoid receptor levels in the hippocampus do not occur until P45. Attenuation of ACTH and corticosterone in handled animals following a stressor first occurs at P23 and lasts through adulthood [90]. The decrease in CRH expression in the PVN requires multiple days of the handling procedure, suggesting that repeated experience-dependent activation of the PVN is required for the long-term impact on transcription [91]. The burst of maternal care upon return of the pups to the dam produces an increase in gene expression in several regions of the pup's brain including the amygdala, bed nucleus of the stria terminals (BnST) and the PVN [91]. With repeated days of handling the combinatorial output from these circuit results in decreased activation of the PVN and decreased CRH expression [92]. Together, these results indicate that the hypothalamus is central to the neuroplasticity observed in response to AMC that sets the stage for long-lived adaptive changes to neuroplasticity in other brain regions.

Pups raised by dams selected for high levels of LG and ABN have behavioral phenotypes that resemble AMC rat pups randomly assigned to dams and handled daily [93]. Handling of rat pups increases maternal licking/grooming behavior, decreases glucocorticoid responses and decreases measures of anxiety-like behavior in adult offspring [14,94] that correspond to methylation changes including Nr3c1 (GR gene) and Grm1 (metabotropic glutamate receptor 1) in hippocampus [54,95]. The handling paradigm also has been shown to enhance memory formation in the Morris water maze and for novel object recognition [96] as well as to prevent age-related impairments in Morris water maze performance [97]. Brief periods of separation between infant Squirrel monkeys and mothers also dampened cortisol responses and stress vocalizations at 3 years of age [98] and rhesus macaques peer raised in nurseries showed more social deviant behaviors than those raised by mothers [83], suggesting that maternal rat studies provide direct insights relevant to primates. Lastly, a prior comparison of rat vs. human brain samples for maternal care induced methylation changes has shown strong conservation [10], suggesting a direct translational relevance of rat studies to humans.

Imprinting mechanisms within the first week of postnatal life regulate a switch to maternal expression of Ube3a and the cross-regulation of Ube3a with global DNA methylation levels and other imprinted genes. It is hypothesized that Ube3a is mechanistically involved in the establishment of early life resiliency from AMC (FIG. 3), supported by published [1,22,73,77,99,100] and preliminary data shown in FIGS. 4-10.

Understanding the mechanistic basis of the benefits of positive early life experiences such as augmented maternal care has potential for translation to humans in both policy recommendations as well as potential diagnostic and therapeutic benefits for those with adverse early life experiences. For instance, the results could provide a mechanistic scientific basis for the economic benefits of funding social worker support programs for new mothers in communities at high risk for the development of mental health disorders. Secondly, since the inventors will be attempting to achieve a modulation of a paternal Ube3a isoform to mimic the molecular mechanisms of augmented maternal care, this research could eventually be designed for human therapies. Since these experiments will reveal novel insights into the epigenetic regulation of Ube3a, the basic science findings of this work are also expected to benefit Angelman syndrome and Dup15q syndrome research, as well as the more general research into UBE3A mechanisms involved in autism and cancer [1,101].

This work is designed to address several major gaps in knowledge that currently limit a molecular understanding of the effects of maternal care on resiliency at both the genome-wide level and the Ube3a locus. This work seeks to determine how augmented maternal care epigenetically programs cognitive resiliency rather than pursuing risk models of stress or UBE3A's role only in rare genetic disorders. Despite the widespread acceptance of the rat AMC model of resiliency [11-15], there have been no prior genome-wide analyses of transcription and epigenetic differences from this model. This work also utilizes a novel Ube3a deletion model in rat that has been generated by CRISPR/Cas9 technology. No equivalent Ube3a deletion model exists in mouse, as existing AS models are mutant or multi-gene deletions. Therefore, this study is experimentally positioned to answer critical questions about Ube3a imprinting and isoform expression in early postnatal life with and without augmented maternal care. This work repurposes an artificial transcription factor designed to treat AS in order to modify paternal Ube3a levels after the critical window for AMC in an effort to improve behavioral resilience in offspring. Sex differences in epigenomic profiles and transcriptomic differences will be addressed directly and correlated with behavioral differences to understand sex differences in resiliency epigenetics.

E. Data on Genome-Wide and Imprinting Impacts of AMC in Rat Hypothalamus

Figure 4:
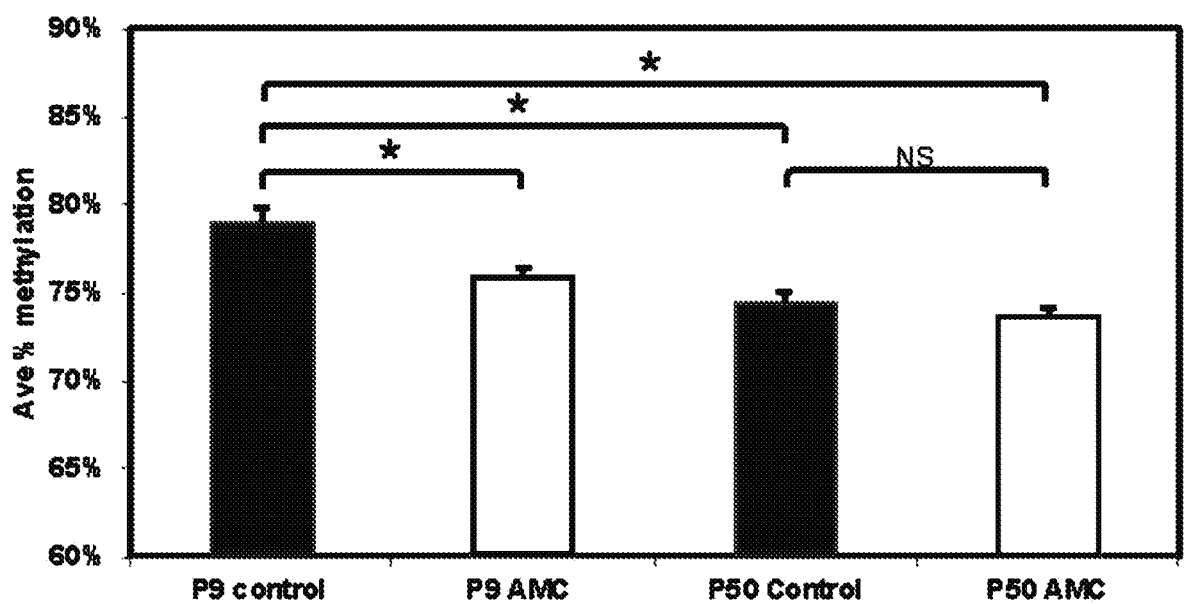
FIG. 4. Global hypomethylation following augmental maternal care in P9 male hypothalamus. WGBS summary of average % CpG methylation genome-wide showing a significant 3.0% methylation difference with AMC at P9 not P50 hypothalamus. CpH methylation levels were not significantly different with AMC (not shown). AMC CpG hypomethylation was observed on every chromosome except chrY. *$p<0.05$; NS, not significant by ANOVA followed by post hoc t-test.
Figures 5A, 5B:
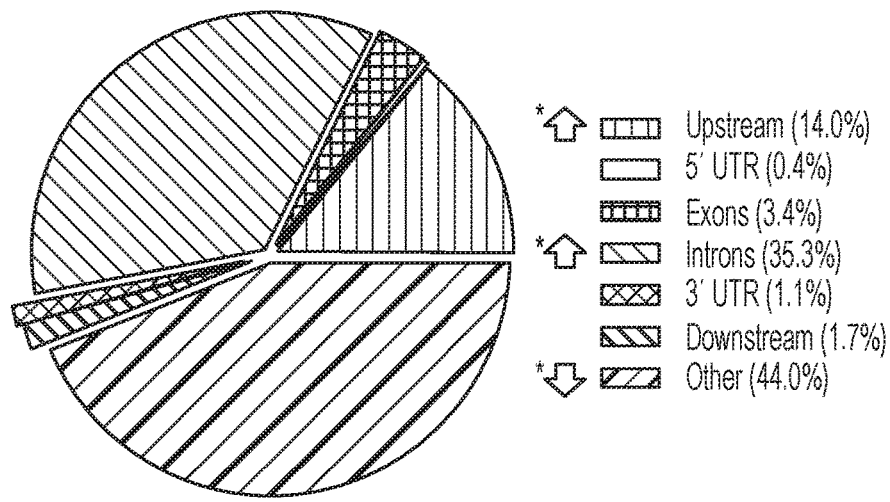
FIGS. 5A-5B. AMC differential methylated regions are enriched for genes and gene pathways regulating behavior and synapses.
Figure 6A:
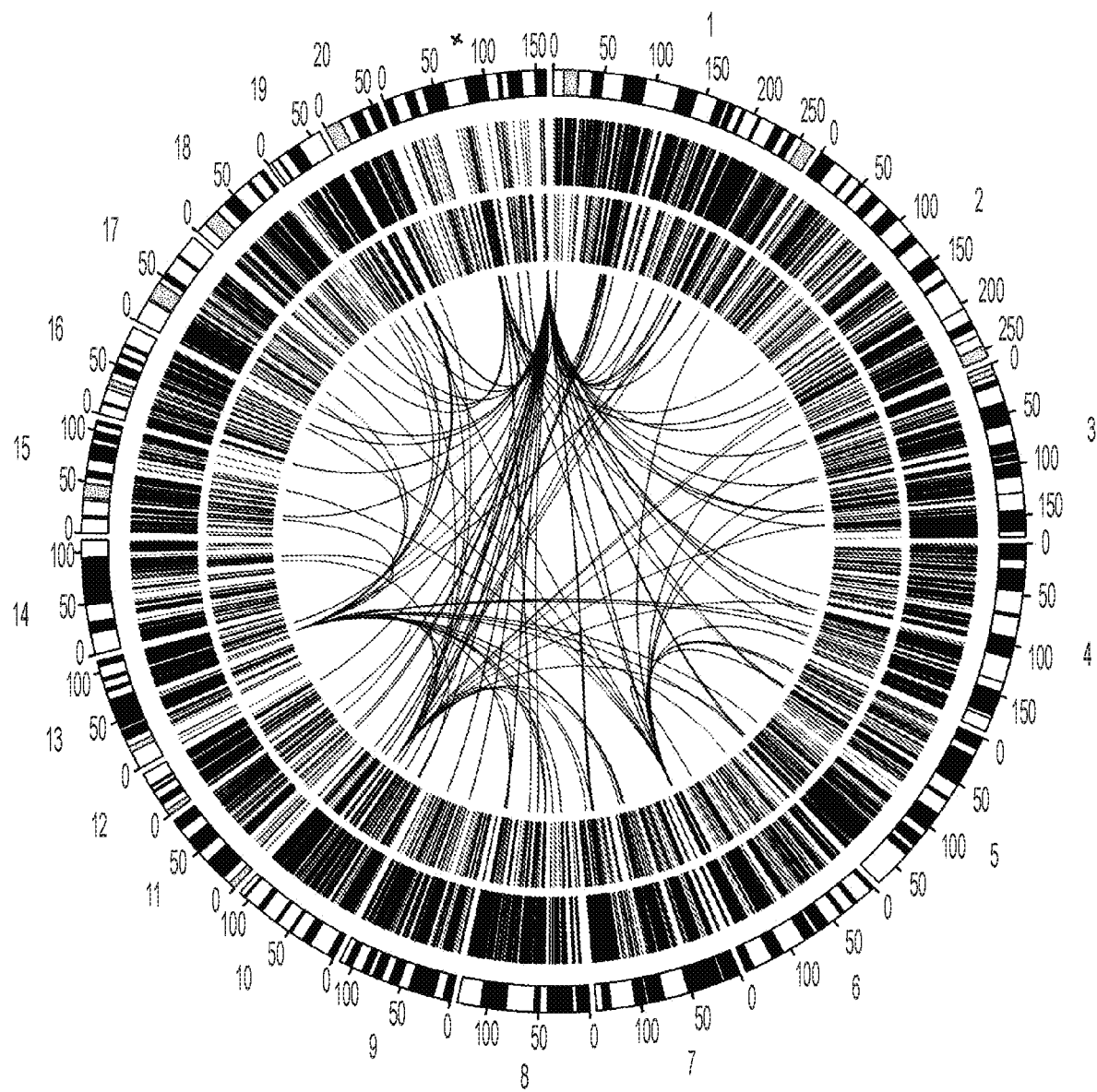
FIGS. 6A-6C. Genome-wide alterations in methylation AMC in P9 hypothalamus.
Figures 6B, 6C:
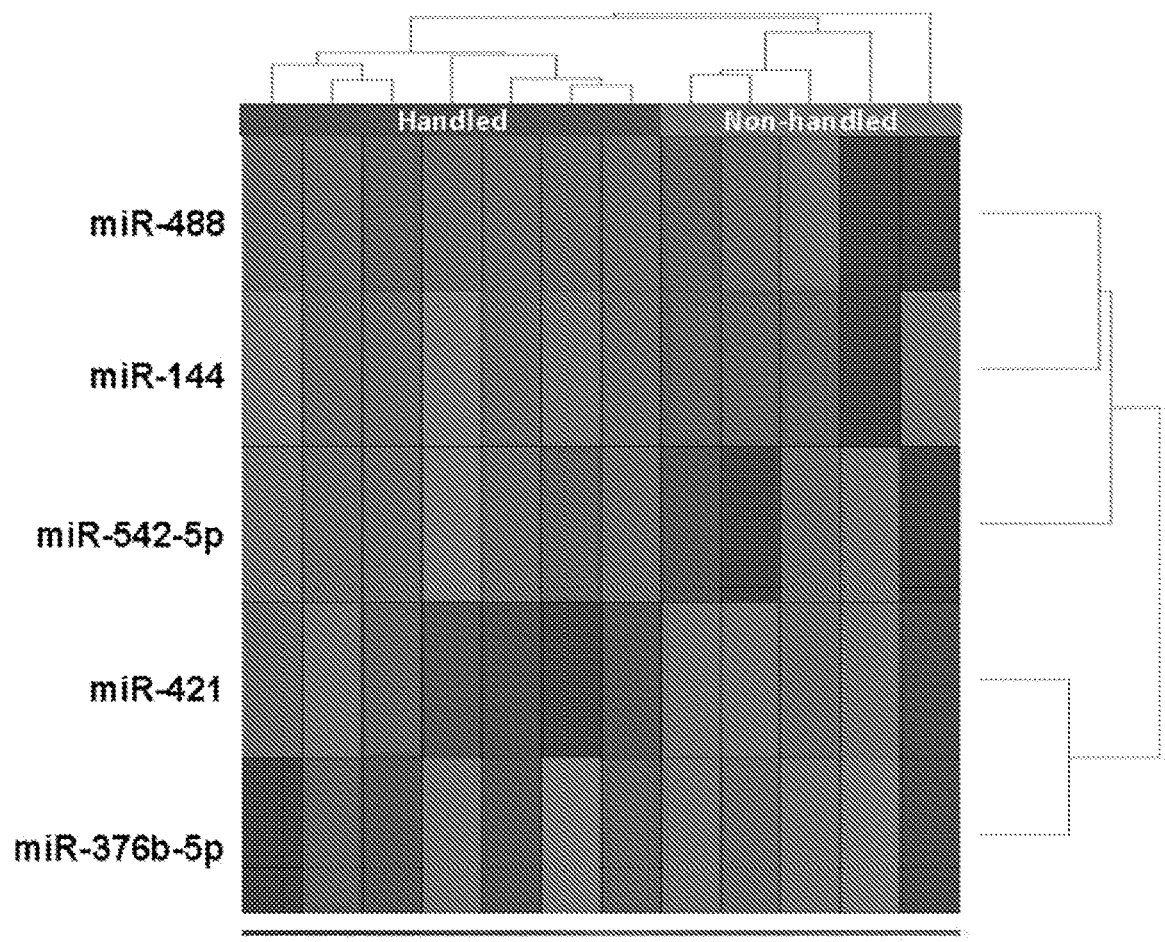

To explore genome-wide alterations in the transcriptome and methylome immediately following augmented maternal care (AMC), hypothalami from 3 male P9 rat pups from each group (AMC vs. control) were examined for genome-wide differences in DNA methylation (WGBS), gene expression (RNA-seq) and miRNA expression. Bioinformatic alignment to the rat genome (rn6) using tophat and cuffdiff identified 2,464 differentially expressed genes that were significant (q<0.05) after FDR correction. WGBS analysis demonstrated a significant global hypomethylation genome-wide in the handled (AMC) samples compared to nonhandled control at P9 but not P50 (FIG. 4). To identify specific genes associated with AMC-induced methylation changes, a custom bioinformatics approach [5,6] identified a total of 9,439 differentially methylated regions (DMR) between AMC versus control P9 hypothalami of which 5,286 were associated with annotated genes, that were enriched for behavior and synapse functions (FIG. 5). RNA-seq analysis of AMC P9 hypothalami revealed 2,337 differentially expressed genes, 473 of which also overlapped DMRs. FIG. 6 includes a circos plot showing chromosomal regions of differential methylation, gene expression, and gene targets of 5 differentially expressed miRNAs, including 2 X-linked miRNAs and another from the imprinted Dlk1/Meg3/Rian locus. Enriched gene ontology terms from RNA-seq analyses included translation and oxidative stress processes, as well as synapse part, indicating central role for AMC in processing controlling synaptic protein translation and oxidative stress response.

Interestingly, several genes up-regulated with AMC are associated with psychiatric disorders (Slc6a4, Htr2c, Gria3, Gria4, Grin2a, Gabra1, and Gabrb3). The imprinted Ube3a gene, implicated in Angelman syndrome, Dup15q syndrome, and autism [1], was also significantly upregulated in the AMC group. Genome-wide alterations to DNA methylation, chromatin, and expression of synaptic genes associated with UBE3A overexpression in Dup15q brain and cell lines have recently been demonstrated [5,6]. Specifically, the AMC-associated global hypomethylation observed in the P9 but not P50 hypothalamus (FIG. 4) is similar to the global hypomethylation observed in Dup15q brain and neurons [6], and could be associated with transient changes to Ube3a as a result of P2-P8 handling. In addition, transcripts for a number of epigenetic chromatin regulators, glutamatergic and GABAergic neurotransmitter receptors, and protocadherin genes involved in neuronal identity [102,103] were higher in P9 AMC pups, consistent with genes and gene ontologies found to be aberrantly methylated and expressed in Dup15q brain [6]. In contrast, transcripts that were lower in the AMC P9 hypothalamus included the stress response genes, Crh and Crhr1 (CRH receptor), as well as galanin (Gal) and its receptor Gpr151. Galanin is implicated in major depressive disorders (MDD) [104,105] and its levels are significantly elevated in MDD brains from suicide victims, with increased promoter methylation [106].

Gene ontologies of AMC altered genes identified a number of functions relevant to resiliency, including oxidative stress (FIG. 6). UBE3A is a central mediator in oxidative stress responses, as cells without Ube3a have an impaired senescent and apoptotic response to sub-lethal and lethal doses of oxidative stress [81]. Furthermore, maternal Ube3a deficient AS mice exhibit increased superoxide in hippocampus that was effectively reduced by a mitochondrial-specific antioxidant, methansulfonate [107]. AS mice have increased anxiety-like behaviors, and when the offspring of maternal Ube3a mutant dams are compared to those of dams with paternal Ube3a deficiency, their WT offspring have lower brain levels of GR expression [78]. Together, these results are consistent with the hypothesis that UBE3A could be a central mediator of the HPA responses to AMC genome-wide by acting through a combination of oxidative stress and chromatin mechanisms observed in Dup15q syndrome [6].

To verify that altered Ube3a was a robust and reproducible finding in response to AMC and to examine differential Ube3a isoforms, RNA was isolated from P9 hypothalami of rat pups following AMC at two different laboratories (Baram and Stolzenberg) and quantitative RT-PCR was performed. FIG. 7 demonstrates that full length Ube3a2/3 isoforms (containing the ubiquitin ligase catalytic domain) are significantly increased in hypothalamic of AMC handled pups, but the truncated alternatively polyadenylated transcript (Ube3a1) described in Valluy et al. [73], is decreased in AMC pups. Also, one of the miRNAs upregulated with AMC, miR-542-5p is predicted to bind to the unique Ube3a1-S 3'UTR, similar to miR-134 described in Valluy et al. [73].

Although parentally imprinting is predicted to have evolved to maximize maternal resources, surprisingly little research has investigated imprinted genes in response to alterations in maternal care. A genome-wide analysis of the overlap with AMC altered genes and imprinted genes was therefore performed. A total of 29 AMC DMRs mapped to 24 imprinted genes, 3 genes which also showed transcription differences (Nnat, Begain, Tssc4). Nnat encodes the paternally expressed membrane protein Neuronatin with high expression in neonatal postmitotic neurons that declines in adulthood [108].

To explore any of the other imprinted genes identified in AMC may be directly affected by Ube3a expression differences observed with AMC, the imprinted gene lists were compared with a UBE3A siRNA knockdown experiment in a human neuronal cell line model of Dup15q (SH-15M) [6]. FIG. 8 demonstrates the number of imprinted genes altered in transcription or DNA methylation in rat AMC or human UBE3A siRNA knockdown (UBE3A KD), showing overlap of Ube3a and Dlk1, as well as a significant overlap of 11 DMRs overlapping between imprinted genes altered by siRNA UBE3A KD and rat AMC. These results support the hypothesis to be further tested that modulation of Ube3a imprinting and expression by early life experience may influence a network of imprinted genes, resulting in long-lived behavioral differences. Imprinted gene networks involving Zac1 [109,110] and H19 [53,111] as hub regulators have been demonstrated in embryonic stages, but to date there is no published evidence of early postnatal imprinted gene networks in brain or involving UBE3A as a hub regulator.

The finding that Ube3a was significantly upregulated in response to AMC was exciting, not only because Ube3a is an imprinted gene that is both regulated by and regulates neuronal synaptic activity [71-73], but also because it may be an important molecular link between the global hypomethylation and changes to oxidative stress and protein translation pathways in the hypothalamus in the first week of life. As demonstrated previously, the paternal allele regulating the neuron-specific expression of the long paternally expressed Ube3a-ATS transcript undergoes dramatic chromatin decondensation from P1-P14 in mouse neurons (FIG. 9) [22]. While extremely rare in the genome, the large-scale chromatin decondensation was observed at the only other imprinted locus also containing clusters of both snoRNAs and miRNAs, Dlk/Gtl2. Interestingly, the noncoding truncated isoform of Ube3a (Ube3a1) prevents exuberant dendritic growth and promotes spine maturation in rat hippocampal neurons by acting as an endogenous competitor of miR134 and its dendritic-promoting effects [73]. miR134 is located within the imprinted miRNA cluster downstream of the Dlk1/Gtl2 locus (FIG. 9). While miR134 was not one of the five significant AMC differential miRNAs (FIG. 6), two of the five do have connections to these imprinted loci. miR-376b-5p, which is located within the Gtl2 maternally expressed miRNA cluster, is known to target BDNF [112] and the mTOR pathway [113].

Furthermore, a predicted recognition site for miR-542-5p was identified within the Ube3a1 isoform-specific 3'UTR (FIG. 7).

Figure 10D:
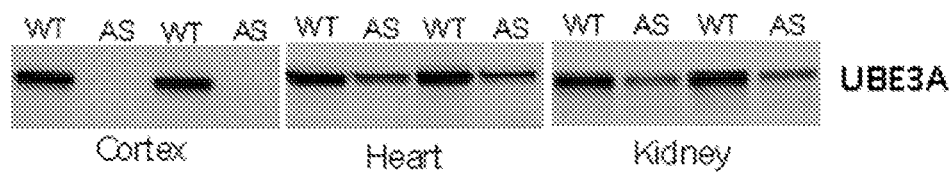

While the results from this work implicate a role for Ube3a and at least one additional imprinted locus (Dlk/Gtl2/miRNA) in the P9 AMC hypothalamus, to directly test the hypothesis that Ube3a imprinting and expression patterns are central to the genomic effects on DNA methylation and imprinted miRNA alterations, a novel rat Ube3a deletion model will be used. FIG. 10 shows the sequence and Western blot analyses of two successfully generated founder lines that have completely deleted the entire Ube3a gene body. Rats with maternal, but not paternal, Ube3a deletions of both founders have AS phenotypes of hindlimb clasping and motor deficits that develop in adulthood.

The first objective (Aim 1) involves testing several key Ube3a-related hypotheses from preliminary findings that AMC is associated with a shift in Ube3a long versus short isoforms in the P9 hypothalamus. Specifically, which Ube3a isoforms show differential allelic expression at P2 and which show differentially allelic expression in handled (H) versus non-handled (NH) P9 hypothamic neurons? Are the transcriptional changes, particularly those at other imprinted genes in AMC versus control hypothalami dependent on maternal or paternal Ube3a alleles? Finally, are the imprinted noncoding RNAs regulating Ube3a in early postnatal life required for the DNA methylation differences in the P9 hypothalamus with AMC?

The second objective (Aim 2) involves testing the hypothesis that the paternal allele of Ube3a is necessary for the behavioral and molecular phenotypes resulting from AMC. Specifically, do handled pups that are genetically deficient for the paternal Ube3a allele fail to show behavioral differences compared to non-handled wild-type or deletion offspring? While adult behavioral phenotypes are not expected from paternal Ube3a deletion in this AS model, significant interaction effects between Ube3a genotype and handling in some behaviors are expected.

The third objective (Aim 3) seeks to address the larger translational question: could a Ube3a-based epigenetic therapy be beneficial for those who did not benefit from AMC in neonatal life? In more specific terms, if the critical period of the first week of life (P2-P8) is missed for the benefits of AMC, could paternal Ube3a expression be "reset" back to the biallelic expression pattern observed in early life by using a therapeutic intervention engineered for turning on the silent paternal allele in AS?

Figure 11:
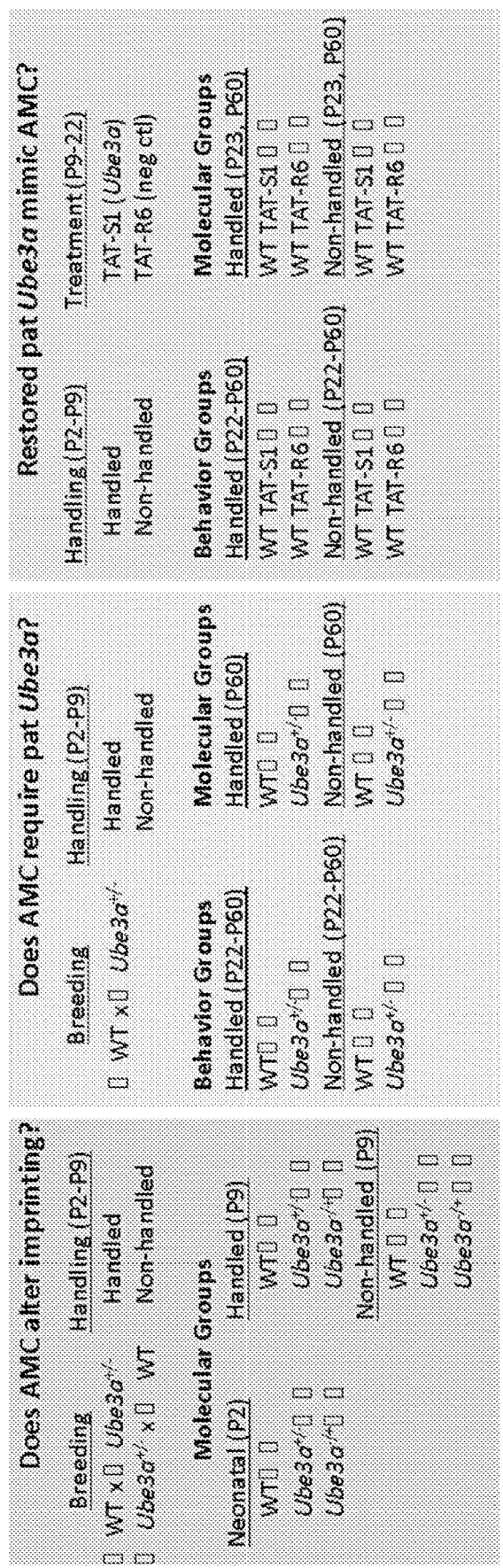
FIG. 11. Rat breeding, handling, and treatment groups by Aim. Design of rat pup sex, genotype, and treatment groups for each aim. Aim 1 investigates molecular assays while Aims 2 and 3 will investigate behavioral assays as well.
Figure 12A:
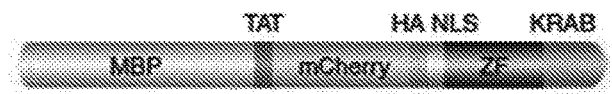
FIGS. 12A-12E. Design and testing of a paternal UBE3A-based therapeutic in a AS mouse model.
Figure 12B:
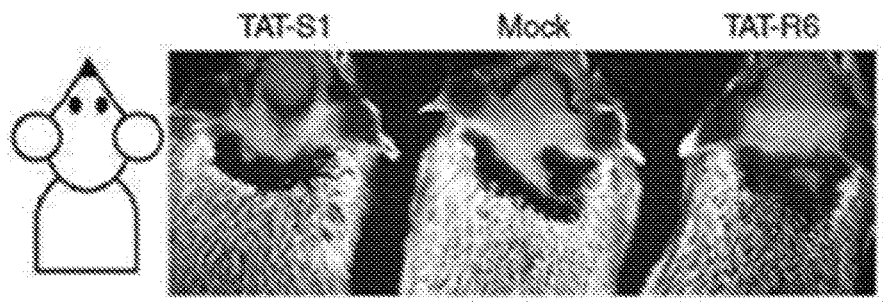
Figure 12C:
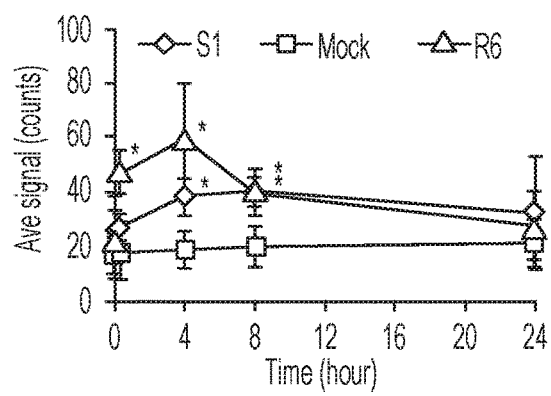
Figure 12D:
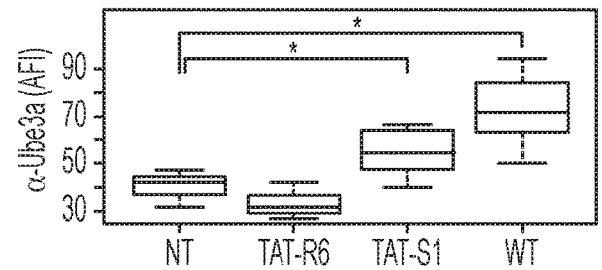
Figure 12E:
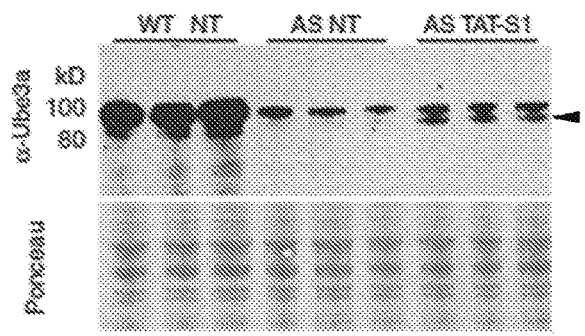

Aim 1: Investigation of Augmented Maternal Care Effects on Imprinted Expression of Ube3a and the Downstream Impacts of Altered UBE3A Levels on Genome-Wide Transcription and Methylation Pup handling and maternal behavior observations:

Male Ube3a deletion rats (Ube3a$^{+/-}$, FIG. 11) will be colony bred to purchased Sprague Dawley WT rat dams using a paternal inheritance pattern to avoid phenotypes associated with the maternally inherited AS disease model that develop in adulthood [78]. FIG. 11 outlines the breeding and handling scheme for Aim 1, which is to breed the Ube3a deletion both maternally and paternally to independently examine Ube3a isoforms expressed from each parental allele in response to handling and AMC. Aim 1 will examine both maternally and paternally Ube3a deleted rat pups but only at P2 and P9 before any AS phenotype is detected. Dams will be observed for parturition daily until day of birth (P0). The AMC handling procedure will follow a published protocol [114]. Each cohort of 8 timed pregnant dams in each of the two breeding schemes will be split into two equal sized groups: 1) augmented maternal care (H), in which pups will be handled for 15 min minutes daily from P2 through P8, and 2) controls that will not be touched between P2 and P8 (NH). To spread the genetic diversity of the colony across different dams, all pups will be collected together at P2 and randomly cross-fostered by placing 10 pups (5 M and 5 F) per dam in clean cages with new nesting materials. Litter effects will be therefore controlled and randomized in the experimental design. The remaining P2 pups (~2-8 per cohort expected) will be euthanized and brains will be frozen for molecular assays in Aim 1. Cages will remain unchanged during P2-P9 for both experimental groups. For the handled (H) group, each day at the same time (1 h after lights on), dams and pups will be placed in separate bedded cages for 15 min with a heating pad under the pup cage to prevent hypothermia. Pups will be then returned to the home cage, followed by the dam. Maternal behavior will be scored as described for 5 observation periods (3 in the light phase, 2 in the dark phase) daily for P2-P9 postpartum by individuals unaware of the experimental group of the animals. Within each observation period, the behavior of the mother will be scored every 3 minutes as described previously [115-117]: the mother off pups; mother licking/grooming any pup; and mother nursing pups in either an arched-back posture, a "blanket" posture (dam lies over the pups), or a passive posture (dam lies either on back or side).

Tissue Sampling:

At P9, rat pups will be euthanized and brains will be quickly removed and flash frozen on dry ice. Hypothalamus samples will be collected using 1 mm punch biopsies based in part on previously published methods for rats [118], an atlas for the developing rat brain [119]. Punch samples will be used for RNA, DNA, and protein isolations (1-2 pups of each sex and genotype per litter each for RNA, DNA, and protein). Additional hypothalamus punch samples will arranged in tissue arrays in paraffin blocks for in situ analyses as described previously [120,121]. RNA will be isolated using miRNeasy mini kit with on-column DNase digestion (Qiagen). Protein isolations will be performed to preserve post-translational modifications of histones, as described previously [6]. Genotyping for the Ube3a deletion will be performed on DNA samples. Each sample will be stored with the age, dam ID, genotype (including parental origin), and sex.

Ube3a Isoform Analyses of Maternal and Paternal Alleles:

RNA samples from P9 hypothalami of each treatment group, sex, litter, and genotype will be selected for quantitative RT-PCR analyses using combinations of primers designed to the unique 5' ends of Ube3a isoforms 1-3 encoded in exons 2-4, the middle exons 5-10 common to all known isoforms, and the alternative 3' UTRs (Ube3a1 or Ube3a2/3, as in FIG. 7). Western blot analyses will be performed on protein isolates from the same samples with detection using different anti-UBE3A antibodies detecting different protein domains (Sigma E8655, monoclonal to full length UBE3A2 that detects a paternal-specific truncated protein [2]; Sigma 3E5, monoclonal to aa 315-415 of UBE3A1/3 or aa 336-436 of UBE3A2 that detects both nuclear and cytoplasmic UBE3A [122]; and Bethyl A300-352, polyclonal directed to aa 400-450 of human/rat UBE3A3). Immunofluorescence will be performed using the same panel of Ube3a antibodies on sections of the tissue array and counterstained with DAPI to determine subcellular localization. Select antibodies will be used on Western blots to detect known downstream ubiquinated targets of UBE:3A in the nucleus (RING1B, H2A, and H2A.Z) or cytoplasm (HHR23, TSC2, and Arc) with GAPDH as a loading control, detected, quantitated, and compared for statistical significance as described previously [6]. The results from these analyses will determine which transcript and protein isoforms are expressed on the maternal versus paternal allele, which isoforms and alleles are changed in response to P2-P8 handling, and how maternal vs paternal Ube3a deletions affect nuclear or cytoplasmic protein targets.

Genome-Wide Analyses of Changes to mRNA, lncRNA, miRNA, and DNA Methylation Levels:

The previous analyses of the effects of UBE3A overexpression in Dup15q syndrome has demonstrated genome-wide changes to additional transcripts and DNA methylation levels [6]. RNA-seq has an advantage over microarray based transcriptome assays because of the ability to detect strand-specific exons and promoters, noncoding transcripts, and align with methylomic assays, but is not ideal for detecting processed miRNAs, which will be detected by microRNA-seq, which has the advantage over the Nanostring method used in FIG. 6 in its ability to detect non-annotated or edited miRNAs. For RNA-seq, rRNA will be removed from total RNA by ribodepletion and libraries will be constructed using the NEBNext Ultra Directional RNA Library Prep with a unique barcode (NEBNext Multiplex Oligos) for each sample. For microRNA-seq, libraries will be prepared using the TruSeq small RNA library prep kit (Illumina) that preferentially targets microRNAs and other small RNAs with a 3' hydroxyl group resulting from enzymatic cleavage by Dicer or other RNA processing enzymes. Library quality will be assessed by bioanalyzer and libraries with unique barcodes will then be quantified and pooled for sequencing (6/lane). Sequencing will be performed on an Illumina HiSeq 4000 to generate 100 bp paired end reads. Data analysis pipelines for detecting differential gene expression between sexes and treatment groups in the RNA-seq experiments will include Tophat2 gene counts with FeatureCounts, and differential analysis in EdgeR, as described previously [123]. Analysis of microRNA-seq will be conducted using CAP-miRSeq pipeline, which includes alignment with miRDeep2 mapper and edgeR to examine differential miRNA expression [124]. Differential gene expression will be validated using qRT-PCR. Long noncoding Ube3a-ats, Ube3a1, and spliced snoRNA host gene transcripts will be analyzed from the RNA-seq data sets and validated by qRT-PCR. Based on prior studies, Ube3a1, Ube3a2 and multiple miRNAs are expected to increase with synaptic activity [71,73,100]. Imprinting of Ube3a will be determined by direct comparison of strand-specific analysis of Ube3a and Ube3a-ats transcripts from RNA-seq from Ube3a maternal and paternal deletion offspring, and the sense-to-antisense ratio compared between P2 and P9, as well as P9 AMC versus control.

Because of the known impact on global and locus-specific DNA methylation patterns of UBE3A overexpression (in Dup15q brain and neurons) [6] and the preliminary results shown (FIGS. 4-5), DNA methylation analyses will be performed to compare maternal versus paternal encoded Ube3a isoforms, as well as the effects of AMC in P9 hypothalami. Whole genome bisulfite sequencing (WGBS) is the most unbiased method to determine both global and gene-specific differences between samples and is sensitive enough to detect methylation differences over 5 kb regions with low (8-10×) coverage with at least 2 biological replicates [125]. Experience in WGBS and bioinformatics methods for differential methylation will be useful [5-9,126,127]. Briefly, WGBS libraries will be constructed using the Illumina EpiGnome/TruSeq DNA Methylation kit and barcodes. Sequencing of barcoded and pooled libraries will be performed on an Illumina HiSeq4000 to obtain 100 bp single end reads and sequenced to ~10× coverage. After adapter trimming and quality assessment, all WGBS reads will be mapped to the reference rat genome (rn6) using the Bisulfite Seeker program [128] and subsequent analysis will be done with custom HMMs, Perl, and R scripts [126,127]. DMRs will be identified using false discovery correction FWER <0.05, as described previously [5,6]. For Aim 1 hypotheses, DMRs and genomic features (CpG islands, gene bodies, promoters) will be compared for differential methylation between H and NH treatment groups, genotype (Ube3a$^{+/+,+/-,-/+}$) and sex. Significant differential methylation will be validated with custom designed pyrosequencing assays to specific gene loci and independent samples.

In Situ Immunofluorescence and Fluorescence it Situ Hybridization of Heterogeneous Cell Populations:

Since the hypothalamus contains a heterogeneous mix of neuronal and glial cell types, many of the differences identified at the genome-wide level in whole hypothalamic tissues may be due to changes in transcription, methylation, and imprinting in specific subpopulations of cells that shift in abundance as a result of AMC. This possibility will be investigated directly by performing combined immunofluorescence (IF) staining on hypothalamus sections using UBE3A antibodies and antibody marker of specific cell types (POMC, Oxytocin, CRH, AGRP, NeuN, GFAP). All IF antibody combinations will be detected with species-specific fluorescently labeled secondary antibodies and visualized by fluorescence microscopy. Fluorescence levels of specific cell populations will be quantitated by laser scanning cytometry [120,129-132]. Fluorescence in situ hybridization (FISH) will be performed to detect imprinted patterns of chromatin decondensation in rat hypothalamus P2 and P9 samples in order to confirm imprinting effects on chromatin at both imprinted snoRNA repeat containing loci (Ube3a and Dlk1, FIG. 9) in rat neurons but not glia. Differences between parental allele lengths between similar neuronal populations in H versus NH samples will be performed. Rat-specific FISH probes to the syntenic regions of the two imprinted regions in FIG. 9 will be created from a contig of BAC probes (CHORI BAC repository, 4 BAC contigs per locus) and hybridized to fixed and paraffin-embedded hypothalamus sections as described previously [22,133]. The FISH signals of both alleles will be measured on at least 50 nuclei per slide and 3 biological replicates, scored blinded to sample group identity.

Based on what has been observed in mouse brain, P9 hypothalamus is expected to have a greater ratio of Ube3a antisense to sense transcript levels than P2 [22,99,100].

Based on the model in FIG. 3, it is also predicted there will be an increased Ube3a-ats to sense ratio in AMC compared to control pups at P9. Increased imprinting of Ube3a correlates with higher UBE3A protein levels between tissues [99], a hypothesis that will be further tested by the immunofluorescence analyses described below. Based on prior analysis in mouse, FISH signal size differences between maternal and paternal imprinted loci are expected to be distinguishable in P9 but not P2 nuclei [22], and the paternal decondensed allele is expected to be significantly larger in AMC. UBE3A protein levels are expected to be higher in neurons compared to glia, P9 compared to P2 neurons, and AMC compared to control P9 neurons in one or more hypothalamic neuronal subtypes.

Cell heterogeneity and variation within and between cell types in the hypothalamus is a potential confounding factor to be considered in the data analyses. If the cell heterogeneity issue is insurmountable for establishing true epigenetic differences between treatment groups, the specific neuronal cell populations determined to be most dynamic by in situ analyses will be sorted from fresh hypothalamus. Bioinformatic analysis methods may be altered as needed for the less well-annotated rat genome, with assistance from the UCD Genome Center Bioinformatics core. Appropriate statistical tests for multiple comparisons will be selected [6]. In addition to the biological variables already controlled for in these analyses (age, sex, and litter), time of day will be carefully controlled, with all handling treatments and all samples collected at the same time of day. As a control for potential off-target effects of the CRISPR/Cas9 deletion, critical results could be validated in the second Ube3a deletion line (FIG. 10).

Aim 2: Investigate the Necessity of the Paternal Ube3a Allele in Behavioral Outcomes Following AMC Pup Handling and Maternal Behavior Observations:

For Aim 2, crosses to create WT versus paternal Ube3a deletion littermates will be performed (FIG. 11) as described for Aim 1 up until P9. For Aim 2, tail snips from all rat pups will be used for DNA isolation and genotyping after P9 and pups allowed to stay undisturbed except for cage changes until weaning. At weaning, pups will be housed separately by sex and genotype.

Behavioral Testing:

4 treatment/genotype groups (H Ube3a$^{+/+}$, H Ube3a$^{+/-}$, NH Ube3a$^{+/+}$, and NH Ube3a$^{+/+}$), 12 M and 12 F (2 per litter) of each group, will be tested. Behavioral tests were chosen based on those previously observed to be significant with augmented maternal care and that focus on social, emotional, and cognitive measures of resilience.

Anxiety-Like Behavior (P22):

Anxiety-like phenotypes will be assessed using the gold standard of rodent anxiety-like behavior, the elevated plus-maze. Individual subject rats are placed in the center of a plus-shaped Plexiglas maze and allowed to freely explore the maze for 5 min. The maze consists of two open (50× 10×40 cm) and two closed (50×10×40 cm) arms emanating from a central platform to form a plus shape. The apparatus is elevated on a stand 60 cm high. Time spent in the open versus closed arms of the maze and total entries between arms, as an internal control for locomotor activity, are recorded.

Juvenile Social Approach and Social Novelty (P28):

A single experimental rat is individually placed into the center chamber of a 3-chambered Plexiglas apparatus, with the chambers connected by open doors. The experimental rat is allowed to freely explore the chambers for 15 min. Then an unfamiliar, same sex, "stimulus" rat is placed in a wire cage in one side chamber (side randomized). The experimental rat is allowed to move freely throughout the apparatus, and the amount of time spent in each chamber and the number of entries into the chambers is recorded for 15 min. A second unfamiliar stimulus rat is then placed in a wire cage in the previously empty chamber. The test rat is then given a choice between chambers (i.e., familiar or unfamiliar rat). Animal behaviors are videotape and scored for time spent with the familiar or stranger rat [116,134].

Juvenile social dyad interaction test (P35): Rats from the same sex and experimental groups are placed in pairs in a transparent Plexiglas box and social interactions are videotaped over a 10 min period. This is a non-invasive observational study of active and passive play, chasing, wrestling, pinning, grooming, digging, exploring, pushing under or crawling over, inactivity, circling, following, sniffing, freezing, attack, and rearing [135].

Novel Open Field Locomotion (P40):

As a test of anxiety, rats are individually placed in the center of the Plexiglas Coulbourn Instruments TruScan Locomotor apparatus (43.2 cm×43.2 cm×30.5 cm) and allowed to freely explore the chamber for 90 min. Activity is measured automatically using infrared photobeam.

Novel Object Exploration Test (P45):

As a test of short-term memory, rats are individually placed in an empty Plexiglas arena and allowed to explore for 30 min. They are removed from the arena, put back in their home cages for 5 min, and 1-4 small objects (e.g., cup, plastic or ceramic toy, beaker, etc.) are placed equidistant from one another in the arena. Rats are again placed into the arena and allowed up to 30 min to freely explore the objects. They are then removed from the arena, placed in their individual cage and returned to the vivarium. 24 h later they are returned to the arena where one of the objects will have been replaced with a novel object, or relative location change and exploration of the novel object/location will be videotaped and later scored.

Barnes Maze (P50):

This cognitive test for spatial memory consists of a white Plexiglas circular table with 18 holes equally spaced around the periphery, and a dark escape box positioned under one of the holes. Rats will be placed at the center of the table under a black Plexiglas box for 1 min, after which time the box will be removed and the rat will be allowed 5 min to find and enter the hole with the escape box. Rats will be given 2 trials/day over 7 consecutive days to learn the location of the escape box. Time to locate the escape box, distance traveled, and locomotor speed will be measured. In addition, the search strategy used by animals (i.e., spatial versus non-spatial) will be analyzed as described previously [136,137].

Porsolt Forced Swim Test (P60):

Rats will be placed in a plastic cylinder (20×40 cm) filled to a depth of 13 cm with tap water at 25° C. Rats first swim, but then stop swimming and adopt an immobile floating posture. Immobility, defined as floating with only one foot moving to prevent sinking, is scored every 5 sec for the last 4 min of a 6 min test session. Total time spent immobile is used as an index of depression-related phenotype [138].

Molecular Assays:

At P60, all rat littermates not used for behavioral testing will be killed and hypothalamus dissected and frozen. DNA, RNA, protein, and tissue preparations will be processed for molecular and genomic analyses as described in Aim 1.

Sample Size and Statistical Power:

Statistical analyses of behavioral tests will be litter-based and sex-based, meaning these biological variables will be balanced between groups and examined as covariates. Group differences between treatment groups, genotypes, and sex for each behavior will be tested by nested ANOVA. In addition, ANOVA or ANCOVA models with either Tukey's or Benjamini-Hochberg corrected multiple posthoc tests will be performed for interactions and corrections for multiple hypothesis testing, as described previously [6,139]. In addition, maternal behavior scores will be correlated with offspring behavioral tests both dependent and independent of groups to examine individual variations using Spearman rank correlations. For behavioral studies, a minimum of 12 animals per treatment group is required: power analysis using a 10% coefficient of variation indicates that a sample size of 12 per group is required to be 80% certain of detecting a 10% difference between 2 of 6 means at $p<0.01$. Since WGBS data and transcriptomic data correlate much more tightly between biological replicates than behavioral data, 3-4 samples for sequencing will be the initiated as a starting point, and functional validations and follow-up by RT-PCR and pyrosequencing will be performed on a larger group of independent samples from different litters (as in FIG. 7).

WT rats receiving AMC (H Ube3a$^{+/+}$) are expected to show significant differences in social and cognitive behaviors and decreased anxiety based on prior studies [11-15,93]. Paternal Ube3a deletion is expected to impair the behavioral response in the AMC offspring (H Ube3a$^{+/-}$), and make the behaviors more like the control group (NH Ube3a$^{+/+}$). Without handling, paternal Ube3a deletion (NH Ube3a$^{+/-}$) is expected to have only minor impact on behavior compared to WT littermates, since only maternal deficiency of Ube3a in mouse or humans has been associated with behavioral impairments in juvenile and adult animals [140,141]. At the molecular level, P60 hypothalamus is expected to maintain some but not all of the transcriptional and methylation differences observed between H and NH WT offspring, and the genomic and molecular patterns of mutant handled (H Ube3a$^{+/-}$) rats are expected to resemble controls (NH Ube3a$^{+/+}$).

While the expectation from humans and mice with large paternal deletions is that the loss of the paternal Ube3a is not associated with any phenotype [133,134], this specific type of complete Ube3a only deletion has not been examined in any other mammal, so if a behavioral phenotype associated with paternal Ube3a loss is found, this would be of benefit to the field. If paternal Ube3a deletion does not alter behavioral phenotypes associated with AMC, this would still be a definitive and result of interest with relevance to understanding the specific function of parental specific isoforms of Ube3a. This finding would however be unrelated to the hypotheses in Aim 3 that affect expression of the paternally expressed noncoding RNAs upstream of Ube3a-ats. As in Aim 1, biological variables such as time of day, litter, and sex will be carefully controlled to enable reproducibility of findings.

Aim 3: Modulate Paternal Ube3a Expression in Weanling Rats Who Did not Receive AMC from P2-P8

An artificial transcription factor designed to recognize the open chromatin of paternal PWS-IC and reduce expression of the paternally encoding transcripts (Snrpn, Snord116, Snord115, and Ube3a-ats) has been engineered, thereby increasing paternal Ube3a expression in the opposite orientation [2]. By Bind-N-Seq analysis [142], the Binding motif (S1) has a 56-fold specificity enrichment over background ($p<0.001$) [2]. FIG. 12 shows the evidence in mouse that the cell penetrating peptide design of the TAT-S1 ATF allows a rapid localization to the brain following i.p. injection. Interestingly, the major form of Ube3a being expressed differentially is the cytoplasmically localized shorter UBE3A isoform (red arrow in FIG. 12E), most likely paternal UBE3A-1, which is expressed as small fraction of total UBE3A in WT and AS brain. This aim will test the hypothesis that modulating paternal Ube3a isoforms and a biallelic pattern of Ube3a expression from P9 to P23 (weanling) in WT rat pups will allow the AMC long-lived behavioral effects from daily pup handling to be observed even in those not handled from P2-P8.

Pup Handling and Maternal Behavior Observation:

For Aim 3, all crosses will be between WT Sprague Dawley rats for the groups outlined in FIG. 11. The AMC paradigm and maternal behavior scoring will be performed as described for Aim 1 until P9. From P9 through P23, all pups in both H and NH groups will receive i.p. injections of either TAT-S1 or the same construct lacking the KRAB effector domain (TAT-NE) at 200 mg/kg, 3×per week, for 2 weeks. During the P9-P23 treatment regimen, maternal behaviors will also be scored as described for Aim 1, and all groups are expected to experience AMC in response to handling on injection days. Both treatment groups will include an equal number of H versus NH (from P2-P8) and M versus F.

Behavioral Testing:

4 treatment/AMC groups (H TAT-S1, H TAT-NE, NH TAT-S1, NH TAT-NE), 12 M, 12 F (2 per litter) of each group, will be tested for the battery of behaviors described in Aim 2.

Molecular Assays:

At P23 and P60, rat littermates not used for behavioral testing will be sacrificed and hypothalamus dissected and frozen. DNA, RNA, protein, and tissue preparations will be processed for molecular and genomic analyses as described in Aim 1.

Based on the observed effect of the TAT-S1 ATF in mouse, in molecular assays, a change to the paternally derived Ube3a isoforms in TAT-S1 versus TAT-S6 in P23 hypothalamus is expected. Differential genome-wide methylation and transcription associated with other imprinted loci are also expected. If the hypothesis that restoring Ube3a expression patterns back to those of neonatal life will also improve the long-lasting effects on social, emotional, and cognitive behaviors, observations of significant behavioral differences between NH TAT-S1 vs NH TAT-NE and NH TAT-NE vs H TAT-NE, with NH TAT-S1 looking more similar to H TAT-NE in one or more of these behaviors, corresponding to UBE3A differences at P23 would be expected.

Figure 13:
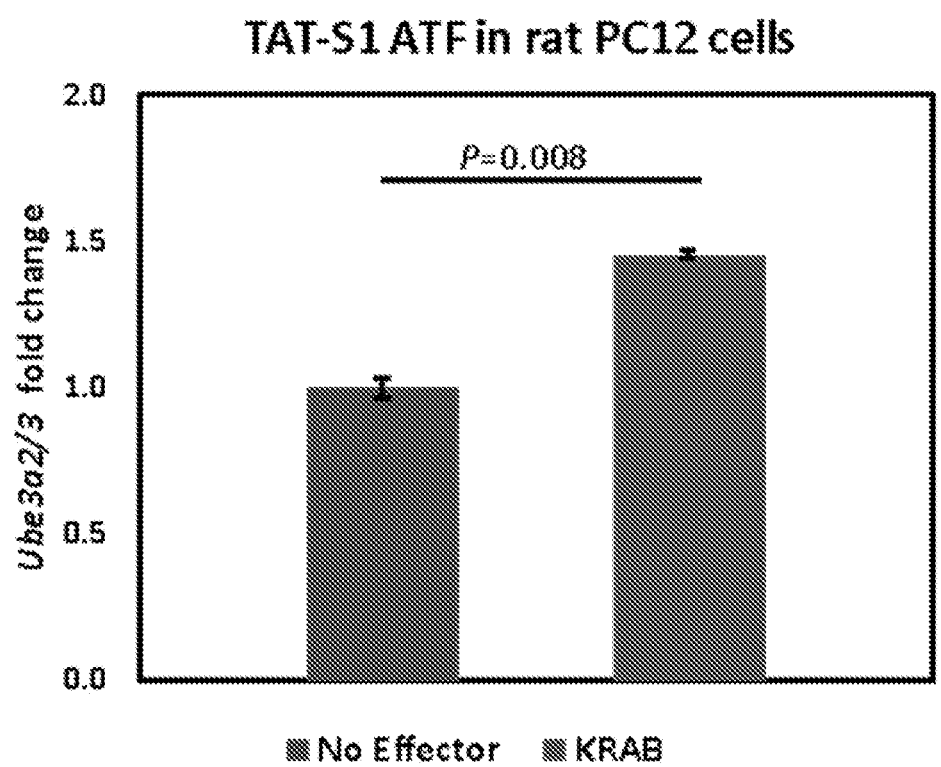
FIG. 13. TAT-S1 increases Ube3a in rat neuronal cells. Rat PC12 cells were transfected with a puromycin inducible TAT-S1 construct shown in FIG. 12A (KRAB) or the TAT-NE (no effector). 24 hours post-transfection, puromycin was added and RNA isolated at 72 hours. The Ube3a2/3 TaqMan assay is described in FIG. 7. N=2 replicates per condition.

Since the TAT-S1 ATF has only been previously tested in vivo in mouse, specificity problems could be found with use in rat, which only differs by 1 bp in the 17 bp recognition site. A pilot analysis of rat PC12 cells showed a significant increase in full length Ube3a transcript following TAT-S1 compared to TAT-NE (FIG. 13), suggesting efficacy in rat. However, if Bind-N-Seq analysis [142] shows multiple binding sites, the ATF will be redesinged specifically for rat. Off-target effects of TAT-S1 are not expected because of the high significance of enrichment for its target [2], but genomic data sets will be interrogated for enrichment of S1 motifs as further assurance. There also could be toxicity effects associated with injecting rat pups with a similar dosage previously found to be well tolerated in adult mice. A lower dosage could be attempted or an alternative delivery method attempted, such as osmotic pump directly to the brain.

Sprague-Dawley post natal day 50 (P50) adult rats will be ordered for timed pregnancies in the experimental studies. The Ube3a deletion line already on a Sprague-Dawley background will be bred to female rats from the same commercial source to maintain an outbred background of the mutant colony. Estrous females will be identified by vaginal lavage and mated with sexually experienced males. Successful mating will be confirmed with sperm plugs. Timed-pregnant Sprague Dawley rats will be housed in groups and observed for parturition daily until day of birth (P0). On P2, pups from all litters will be briefly gathered and 10 pups assigned at random to each dam (5F and 5M), as described previously [114]. Dams and their litters will be housed separately in 46×18×30 cm Plexiglas cages with nesting material and divided into four equal sized groups: 1) augmented maternal care (H), in which pups will be handled for 15 min minutes daily from P2 through P8, 2) nonhandled controls (NH) that will not be touched between P2 and P8, 3) augmented maternal care (H-Veh) that will be handled as in group #1 while the dam is fed cornflake with a drop of corn oil, and 4) augmented maternal care (H-Top) that will be handled as in group #1 while the dam is fed cornflake with a drop of corn oil with topotecan (dosage determine in Aim 2). For the H groups, each day at the same time, dams and pups will be placed in separate bedded cages for 15 min with a heating pad under the pup cage to prevent hypothermia. Pups will be then returned to the home cage, followed by the dam. Maternal behavior will be scored as described previously [115] for 10 3-min observation periods daily for P2-P8 postpartum by individuals unaware of the experimental group of the animals. The following behaviors will be scored: mother off pups; mother licking/grooming any pup; and mother nursing pups in either an arched-back posture, a "blanket" posture (in which the mother lies over the pups), or a passive posture (in which the mother is lying either on her back or side).

Rats (2 M and 2 F per litter) will be behaviorally phenotyped from P22-P60 days of age. The behaviors to be examined have been intensively studied to provide insights into behavioral components of social deficits, anxiety, and learning disorders.

Anxiety will be tested in the elevated plus maze and the open field test. For the elevated plus maze, rats are individually placed in the center of a plus-shaped Plexiglas maze and allowed to freely explore the maze for 5 min. The maze consists of two open (50×10×40 cm) and two closed (50×10×40 cm) arms emanating from a central platform to form a plus shape. Time spent in the open and closed arms is recorded and compared to total distance traveled and number of arm entries to normalize for activity. In the open field test, rats are individually placed in the center of the Plexiglas Coulbourn Instruments TruScan Locomotor apparatus (43.2 cm×43.2 cm×30.5 cm) and allowed to freely explore the chamber for 90 min. In this paradigm, total activity and time exploring the center of the chamber is scored as a measure of anxiety and locomotion.

Social interaction tests are widely used in rats and mice as a model of social withdrawal, a component of several mood disorders. In the social interaction test, non-littermate rats from the same sex and age are placed together in pairs in a transparent Plexiglas box and social interactions are video-taped over a 10 min period. This is a non-invasive observational assay. Examples of behaviors to be scored are grooming, digging, exploring, crawling over, inactivity, circling, following, sniffing, freezing, attack, and rearing. In the social approach test, a single "test" rat is individually placed into the center chamber of a 3-chambered Plexiglas apparatus, with the chambers connected by open doors. The test rat is allowed to freely explore the chambers for 15 min. Then an unfamiliar, same sex, "stimulus" rat is placed in a wire cage in one side chamber (side randomized). The test rat is allowed to move freely throughout the apparatus, and the amount of time spent in each chamber and the number of entries into the chambers is recorded for 15 min. A second unfamiliar rat is then placed in a wire cage in the previously empty chamber. The test rat is then given a choice between chambers (i.e., familiar or unfamiliar rat). Animal behaviors are videotape and scored for time spent with the novel rat compared to the empty wire cage as a measure of "sociability" and the time spent between the familiar compared to stranger rat as a measure of social novelty preference.

In the novel object recognition tests, rats are individually placed in an empty Plexiglas arena and allowed to explore for 30 min. They are removed from the arena, put back in their home cages for 5 min, and 1-4 small objects (e.g., cup, plastic or ceramic toy, beaker, etc.) are placed equidistant from one another in the arena. Rats are again placed into the arena and allowed up to 30 min to freely explore the objects. They are then removed from the arena, placed in their individual cage and returned to the vivarium. Twenty-four hours later they are returned to the arena where one of the objects will have been replaced with a novel object, or relative location change (e.g., transposed with one of the other objects) and exploration of the novel object/location will be videotaped and later scored.

The Barnes maze consists of a white Plexiglas circular table (122 cm dia) illuminated from above with 2 LED lights (500W each). The table has 18 holes (7.5 cm dia) equally spaced around the periphery, and a dark escape box is positioned under one of the holes. Rats will be placed at the center of the table under a black Plexiglas box for 1 min, after which time the box will be removed and the rat will be allowed 5 min to find and enter the hole with the escape box. Rats will be given 2 trials/day over 7 consecutive days to learn the location of the escape box. Time to locate the escape box, distance traveled and locomotor speed (distance traveled/escape latency) will be measured. In addition, the search strategy used by animals (i.e., spatial versus non-spatial) will be analyzed as described previously.

The Porsolt forced swim test will be used to evaluate resilience (i.e., behavioral despair) as described previously [138]. Rats will be placed in a plastic cylinder (20×40 cm) filled to a depth of 13 cm with tap water at 25° C. Rats first swim, but then stop swimming and adopt an immobile floating posture. Immobility, defined as floating with only one foot moving to prevent sinking, is scored every 5 sec for the last 4 min of a 6 min test session. Total time spent immobile is used as an index of depression. Testing is carried out in the presence of an observed and animals that sink are immediately removed from the water. At the end of the test the rat is dried and returned to its home cage.

Statistical analyses of behavioral tests will be litter-based and sex-based. Group differences between treatment groups, as well as males and females for each behavior will be tested by nested ANOVA. In addition, maternal behavior scores will be correlated with offspring behavioral tests both dependent and independent of groups to examine individual variations within the population using Spearman rank correlations. The litter-based testing will allow a comparison of behaviors to molecular tests performed on littermates of the same sex.

While the ultimate goal of this work is to find epigenetic signatures of early life experiences relevant to human mental health, it is necessary to use an appropriate animal model that can be experimentally controlled and brain sampled to first identify genes with distinct early life epigenomic signatures. Non-human primates show strong behavioral effects of early life stress and maternal care [82,83], but the characterization of brain samples from multiple developmental time points and animal replicates is more expensive and time consuming than in rodents. Mouse is a good choice for controlled genetic studies, but genetically outbred rats were chosen over inbred mouse strains for a number of reasons. First, the maternal care paradigms in rat are more robust and reproducible than in mouse, and the most common background for knockout mice (C57Bl6/J) have poor maternal care behaviors [84]. Second, rat brain is larger and more easily dissected into specific brain regions for epigenomic studies than mouse brain. Third, Sprague Dawley litters are generally larger (average 10.5) than litters of inbred mouse strains, allowing the sampling of littermates of the same dam for RNA, DNA, chromatin, and behavioral analyses. Fourth, Sprague Dawley rats are outbred, similar to humans, eliminating a problem with mouse strain specific behaviors and allowing for the potential to investigate individual differences in methylation and gene expression with individual genetic differences.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. LaSalle, J. M., Reiter, L. T. & Chamberlain, S. J. Epigenetic regulation of UBE3A and roles in human neurodevelopmental disorders. Epigenomics 7, 1213-28 (2015).
2. Bailus, B. J. et al. Protein Delivery of an Artificial Transcription Factor Restores Widespread Ube3a Expression in an Angelman Syndrome Mouse Brain. Mol Ther 24, 548-55 (2016).
3. Schroeder, D. I. et al. The human placenta methylome. Proceedings of the National Academy of Sciences of the United States of America 110, 6037-6042 (2013).
4. Schroeder, D. I. et al. Early Developmental and Evolutionary Origins of Gene Body DNA Methylation Patterns in Mammalian Placentas. PLoS Genet 11, e1005442 (2015).
5. Dunaway, K. et al. Dental Pulp Stem Cells Model Early Life and Imprinted DNA Methylation Patterns. Stem Cells (2016).
6. Dunaway, K. W. et al. Cumulative Impact of Polychlorinated Biphenyl and Large Chromosomal Duplications on DNA Methylation, Chromatin, and Expression of Autism Candidate Genes. Cell Rep 17, 3035-3048 (2016).
7. Rube, H. T. et al. Sequence features accurately predict genome-wide MeCP2 binding in vivo. Nat Commun 7, 11025 (2016).
8. Schroeder, D. I. et al. Placental methylome analysis from a prospective autism study. Mol Autism 7, 51 (2016).
9. Crary-Dooley, F. K. et al. A comparison of existing global DNA methylation assays to low-coverage whole-genome bisulfite sequencing for epidemiological studies. Epigenetics, 0 (2017).

10. Suderman, M. et al. Conserved epigenetic sensitivity to early life experience in the rat and human hippocampus. Proc Natl Acad Sci USA 109 Suppl 2, 17266-72 (2012).
11. Levine, S. Maternal and environmental influences on adrenocortical response to stress in weanling rats. Science 156, 258-260 (1967).
12. Schreiber, H. et al. Early handling and maternal behavior: effect on d-amphetamine responsiveness in rats. Pharmacol. Biochem. Behav. 9, 785-789 (1978).
13. Hennessy, M. B., Vogt, J. & Levine, S. Strain of foster mother determines long-term effects of early handling evidence for maternal mediation. Physiol. Psychol. 10, 153-157 (1982).
14. McIntosh, J., Anisman, H. & Merali, Z. Short- and long-periods of neonatal maternal separation differentially affect anxiety and feeding in adult rats: gender-dependent effects. Developmental Brain Research 113, 97-106 (1999).
15. Liu, D., Caldji, C., Sharma, S., Plotsky, P. M. & Meaney, M. J. Influence of neonatal rearin conditions on stress-induced adrenocorticotropin responses and norepinepherine release in the hypothalamic paraventricular nucleus. J. Neuroendocrinol. 12, 5-12 (2000).
16. Wilkins, J. F. Genomic imprinting and conflict-induced decanalization. Evolution 65, 537-53 (2011).
17. Haig, D. Coadaptation and conflict, misconception and muddle, in the evolution of genomic imprinting. Heredity (Edinb) 113, 96-103 (2014).
18. Moore, T. Review: Parent-offspring conflict and the control of placental function. Placenta 33 Suppl, S33-6 (2012).
19. Ivanova, E. & Kelsey, G. Imprinted genes and hypothalamic function. J Mol Endocrinol 47, R67-74 (2011).
20. Ubeda, F. & Gardner, A. A model for genomic imprinting in the social brain: elders. Evolution 66, 1567-81 (2012).
21. Yamasaki, K. et al. Neurons but not glial cells show reciprocal imprinting of sense and antisense transcripts of Ube3a. Hum Mol Genet 12, 837-47 (2003).
22. Leung, K. N., Vallero, R. O., DuBose, A. J., Resnick, J. L. & LaSalle, J. M. Imprinting regulates mammalian snoRNA-encoding chromatin decondensation and neuronal nucleolar size. Hum Mol Genet 18, 4227-38 (2009).
23. LaSalle, J. M., Reiter, L. T. & Chamberlain, S. J. Epigenetic regulation of UBE3A and roles in human neurodevelopmental disorders. Epigenomics (2015).
24. Noh, K. M., Allis, C. D. & Li, H. Reading between the Lines: "ADD"-ing Histone and DNA Methylation Marks toward a New Epigenetic "Sum". ACS Chem Biol 11, 554-63 (2016).
25. LaSalle, J. M., Powell, W. T. & Yasui, D. H. Epigenetic layers and players underlying neurodevelopment. Trends in Neurosciences 36, 460-470 (2013).
26. Ramocki, M. B. & Zoghbi, H. Y. Failure of neuronal homeostasis results in common neuropsychiatric phenotypes. Nature 455, 912-918 (2008).
27. Schanen, N. C. Epigenetics of autism spectrum disorders. Hum Mol Genet 15 Spec No 2, R138-50 (2006).
28. Jirtle, R. L. & Skinner, M. K. Environmental epigenomics and disease susceptibility. Nat Rev Genet 8, 253-62 (2007).
29. Dolinoy, D. C., Weidman, J. R. & Jirtle, R. L. Epigenetic gene regulation: linking early developmental environment to adult disease. Reprod Toxicol 23, 297-307 (2007).
30. LaSalle, J. M. The Odyssey of MeCP2 and parental imprinting. Epigenetics 2, 5-10 (2007).
31. Currenti, S. A. Understanding and Determining the Etiology of Autism. Cell Mol Neurobiol (2009).
32. Rutten, B. P. & Mill, J. Epigenetic mediation of environmental influences in major psychotic disorders. Schizophr Bull 35, 1045-56 (2009).
33. Roth, T. L., Lubin, F. D., Sodhi, M. & Kleinman, J. E. Epigenetic mechanisms in schizophrenia. Biochim Biophys Acta 1790, 869-77 (2009).
34. Graff, J. & Mansuy, I. M. Epigenetic dysregulation in cognitive disorders. Eur J Neurosci 30, 1-8 (2009).
35. Henquet, C., Di Forti, M., Morrison, P., Kuepper, R. & Murray, R. M. Gene-environment interplay between cannabis and psychosis. Schizophr Bull 34, 1111-21 (2008).
36. Skene, P. J. et al. Neuronal MeCP2 is expressed at near histone-octamer levels and globally alters the chromatin state. Mol Cell 37, 457-68.
37. Nelson, E. D., Kavalali, E. T. & Monteggia, L. M. Activity-dependent suppression of miniature neurotransmission through the regulation of DNA methylation. J Neurosci 28, 395-406 (2008).
38. Martinowich, K. et al. DNA methylation-related chromatin remodeling in activity-dependent BDNF gene regulation. Science 302, 890-893 (2003).
39. Chen, W. G. et al. Derepression of BDNF transcription involves calcium-dependent phosphorylation of MeCP2. Science 302, 885-9 (2003).
40. Amir, R. E. et al. Rett syndrome is caused by mutations in X-linked MECP2, encoding methyl-CpG-binding protein 2. Nat. Genet. 23, 185-8 (1999).
41. Wilkins, J. F. Genomic imprinting of Grb10: coadaptation or conflict? PLoS Biol 12, e1001800 (2014).
42. Wolf, J. B. & Hager, R. A maternal-offspring coadaptation theory for the evolution of genomic imprinting. PLoS Biol 4, e380 (2006).
43. Buiting, K., Williams, C. & Horsthemke, B. Angelman syndrome—insights into a rare neurogenetic disorder. Nat Rev Neurol 12, 584-93 (2016).
44. Winter, J. MicroRNAs of the miR379-410 cluster: New players in embryonic neurogenesis and regulators of neuronal function. Neurogenesis (Austin) 2, e1004970 (2015).
45. Valdmanis, P. N. et al. Upregulation of the microRNA cluster at the Dlk1-Dio3 locus in lung adenocarcinoma. Oncogene 34, 94-103 (2015).
46. Stelzer, Y., Sagi, I., Yanuka, O., Eiges, R. & Benvenisty, N. The noncoding RNA IPW regulates the imprinted DLK1-DIO3 locus in an induced pluripotent stem cell model of Prader-Willi syndrome. Nature Genetics 46, 551-7 (2014).
47. Vincent, R. N., Gooding, L. D., Louie, K., Chan Wong, E. & Ma, S. Altered DNA methylation and expression of PLAGL1 in cord blood from assisted reproductive technology pregnancies compared with natural conceptions. Fertil Steril 106, 739-748 e3 (2016).
48. Martinet, C. et al. H19 controls reactivation of the imprinted gene network during muscle regeneration. Development 143, 962-71 (2016).
49. Jung, Y. & Nolta, J. A. BMI1 Regulation of Self-Renewal and Multipotency in Human Mesenchymal Stem Cells. Curr Stem Cell Res Ther 11, 131-40 (2016).
50. Ribarska, T. et al. Deregulation of an imprinted gene network in prostate cancer. Epigenetics 9, 704-17 (2014).
51. Monnier, P. et al. H19 lncRNA controls gene expression of the Imprinted Gene Network by recruiting MBD1. Proc Natl Acad Sci USA 110, 20693-8 (2013).
52. Haga, C. L. & Phinney, D. G. MicroRNAs in the imprinted DLK1-DIO3 region repress the epithelial-to-mesenchymal transition by targeting the TWIST1 protein signaling network. J Biol Chem 287, 42695-707 (2012).

53. Fauque, P. et al. Modulation of imprinted gene network in placenta results in normal development of in vitro manipulated mouse embryos. Hum Mol Genet 19, 1779-90 (2010).
54. McGowan, P. O. et al. Broad epigenetic signature of maternal care in the brain of adult rats. PLoS One 6, e14739.
55. Korosi, A. & Baram, T. Z. The pathways from mother's love to baby's future. Front Behav Neurosci 3, 27 (2009).
56. Champagne, F. A., Francis, D. D., Mar, A. & Meaney, M. J. Variations in maternal care in the rat as a mediating influence for the effects of environment on development. Physiology & behavior 79, 359-71 (2003).
57. Meaney, M. J. et al. Postnatal handling increases the expression of cAMP-inducible transcription factors in the rat hippocampus: the effects of thyroid hormones and serotonin. J Neurosci 20, 3926-35 (2000).
58. Weaver, I. C. et al. The transcription factor nerve growth factor-inducible protein a mediates epigenetic programming: altering epigenetic marks by immediate-early genes. J Neurosci 27, 1756-68 (2007).
59. Oberlander, T. F. et al. Prenatal exposure to maternal depression, neonatal methylation of human glucocorticoid receptor gene (NR3C1) and infant cortisol stress responses. Epigenetics 3, 97-106 (2008).
60. McGowan, P. O. et al. Epigenetic regulation of the glucocorticoid receptor in human brain associates with childhood abuse. Nat Neurosci 12, 342-8 (2009).
61. Cheung, I. et al. Developmental regulation and individual differences of neuronal H3K4me3 epigenomes in the prefrontal cortex. Proc Natl Acad Sci USA 107, 8824-9.
62. Arnold, A. P. & Breedlove, S. M. Organizational and activational effects of sex steroids on brain and behavior: a reanalysis. Horm Behav 19, 469-98 (1985).
63. Gatewood, J. D. et al. Sex chromosome complement and gonadal sex influence aggressive and parental behaviors in mice. J Neurosci 26, 2335-42 (2006).
64. Jessen, H. M. & Auger, A. P. Sex differences in epigenetic mechanisms may underlie risk and resilience for mental health disorders. Epigenetics 6, 857-61.
65. Auger, A. P., Jessen, H. M. & Edelmann, M. N. Epigenetic organization of brain sex differences and juvenile social play behavior. Horm Behav 59, 358-63.
66. Plaschkes, I., Silverman, F. W. & Priel, E. DNA topoisomerase I in the mouse central nervous system: Age and sex dependence. The Journal of comparative neurology 493, 357-69 (2005).
67. Weaver, I. C. et al. Epigenetic programming by maternal behavior. Nat Neurosci 7, 847-54 (2004).
68. Roth, T. L., Lubin, F. D., Funk, A. J. & Sweatt, J. D. Lasting epigenetic influence of early-life adversity on the BDNF gene. Biol Psychiatry 65, 760-9 (2009).
69. Egger, G., Liang, G., Aparicio, A. & Jones, P. A. Epigenetics in human disease and prospects for epigenetic therapy. Nature 429, 457-63 (2004).
70. Jones, K. A., Han, J. E., DeBruyne, J. P. & Philpot, B. D. Persistent neuronal Ube3a expression in the suprachiasmatic nucleus of Angelman syndrome model mice. Sci Rep 6, 28238 (2016).
71. Greer, P. L. et al. The Angelman Syndrome protein Ube3A regulates synapse development by ubiquitinating arc. Cell 140, 704-16 (2010).
72. Filonova, I., Trotter, J. H., Banko, J. L. & Weeber, E. J. Activity-dependent changes in MAPK activation in the Angelman Syndrome mouse model. Learning & memory 21, 98-104 (2014).
73. Valluy, J. et al. A coding-independent function of an alternative Ube3a transcript during neuronal development. Nature neuroscience (2015).
74. Jiang, Y. H. et al. Mutation of the Angelman ubiquitin ligase in mice causes increased cytoplasmic p53 and deficits of contextual learning and long-term potentiation. Neuron 21, 799-811 (1998).
75. Yashiro, K. et al. Ube3a is required for experience-dependent maturation of the neocortex. Nature neuroscience 12, 777-83 (2009).
76. Sun, J. et al. UBE3A Regulates Synaptic Plasticity and Learning and Memory by Controlling SK2 Channel Endocytosis. Cell reports 12, 449-461 (2015).
77. Godavarthi, S. K., Dey, P., Maheshwari, M. & Jana, N. R. Defective glucocorticoid hormone receptor signaling leads to increased stress and anxiety in a mouse model of Angelman syndrome. Human Molecular Genetics 21, 1824-34 (2012).
78. Grier, M. D., Carson, R. P. & Lagrange, A. H. Of mothers and myelin: Aberrant myelination phenotypes in mouse model of Angelman syndrome are dependent on maternal and dietary influences. Behavioural brain research 291, 260-267 (2015).
79. LaVoie, M. J., Cortese, G. P., Ostaszewski, B. L. & Schlossmacher, M. G. The effects of oxidative stress on parkin and other E3 ligases. J Neurochem 103, 2354-68 (2007).
80. Mishra, A. et al. E6-AP promotes misfolded polyglutamine proteins for proteasomal degradation and suppresses polyglutamine protein aggregation and toxicity. J Biol Chem 283, 7648-56 (2008).
81. Wolyniec, K., Levav-Cohen, Y., Jiang, Y. H., Haupt, S. & Haupt, Y. The E6AP E3 ubiquitin ligase regulates the cellular response to oxidative stress. Oncogene 32, 3510-9 (2013).
82. Seay, B., Hansen, E. & Harlow, H. F. Mother-infant separation in monkeys. J Child Psychol Psychiatry 3, 123-32 (1962).
83. Suomi, S. J. Early determinants of behaviour: evidence from primate studies. Br Med Bull 53, 170-84 (1997).
84. Millstein, R. A. & Holmes, A. Effects of repeated maternal separation on anxiety-and depression-related phenotypes in different mouse strains. Neurosci Biobehav Rev 31, 3-17 (2007).
85. Levine, S. Infantile experience and resistance to physiological stress. Science 126, 405-406 (1957).
86. Plotsky, P. M. & Meaney, M. J. Early postnatal experience alters hypothalamic corticotropin-releasing factor CRF mRNA, median eminence CRF content and stress-induced release in adult rats. Mol. Brain Res. 18, 195-200 (1993).
87. Francis, D. D., Diorio, J., Plotsky, P. M. & Meaney, M. J. Environmental enrichment reverses the effects of maternal separation on stress reactivity. Journal of Neuroscience 22, 7840-7843 (2002).
88. Roth, T. L. & Sullivan, R. M. Memory of early maltreatment: neonatal behavioral and neural correlates of maternal maltreatment within the context of classical conditioning. Biol Psychiatry 57, 823-831 (2005).
89. Liu, D. et al. Maternal care, hippocampal glucocorticoid receptors, and hypothalamic-pituitary-adrenal responses to stress. Science 277, 1659-1662 (1997).
90. Avishai-Eliner, S., Eghbal-Ahmadi, M., Tabachnik, E., Brunson, K. L. & Baram, T. Z. Down-regulation of hypothalamic corticotropin-releasing hormone messenger ribonucleic acid (mRNA) precedes early-life experience-induced changes in hippocampal glucocorticoid receptor mRNA. Endocrinology 142, 89-97 (2001).
91. Fenoglio, K. A., Chen, Y. & Baram, T. Z. Neuroplasticity of the hypothalamic-pituitary-adrenal axis early in life requires recurrent recruitment of stress-regulating brain regions. The Journal of neuroscience: the official journal of the Society for Neuroscience 26, 2434-42 (2006).
92. Singh-Taylor, A., Korosi, A., Molet, J., Gunn, B. G. & Baram, T. Z. Synaptic rewiring of stress-sensitive neurons by early-life experience: a mechanism for resilience? Neurobiology of stress 1, 109-115 (2015).
93. Francis, D., Diorio, J., Liu, D. & Meaney, M. J. Nongenomic transmission across generations of maternal behavior and stress responses in the rat. Science 286, 1155-1158 (1999).
94. Caldji, C., Francis, D., Sharma, S., Plotsky, P. M. & Meaney, M. J. The effects of early rearing environment on the development of GABA(A) and central benzodiazepine receptor levels and novelty-induced fearfulness in the rat. Neuropsychopharmacology 22, 219-229 (2000).
95. Bagot, R. C. et al. Variations in postnatal maternal care and the epigenetic regulation of metabotropic glutamate receptor 1 expression and hippocampal function in the rat. Proceedings of the National Academy of Sciences of the United States of America 109 Suppl 2, 17200-7 (2012).
96. Meaney, M. J., Aitken, D. H., Bhatnagar, S. & Sapolsky, R. M. Postnatal handling attenuates certain neuroendocrine, anatomical, and cognitive dysfunctions associated with aging in female rats. Neurobiology of aging 12, 31-8 (1991).
97. Fenoglio, K. A. et al. Enduring, handling-evoked enhancement of hippocampal memory function and glucocorticoid receptor expression involves activation of the corticotropin-releasing factor type 1 receptor. Endocrinology 146, 4090-6 (2005).
98. Levine, S. & Mody, T. The long-term psychobiological consequences of intermittent postnatal separation in the squirrel monkey. Neurosci. Biobehav. Rev. 27, 83-89 (2003).
99. Numata, K., Kohama, C., Abe, K. & Kiyosawa, H. Highly parallel SNP genotyping reveals high-resolution landscape of mono-allelic Ube3a expression associated with locus-wide antisense transcription. Nucleic Acids Research 39, 2649-57 (2011).
100. Meng, L., Person, R. E. & Beaudet, A. L. Ube3a-ATS is an atypical RNA polymerase II transcript that represses the paternal expression of Ube3a. Human Molecular Genetics 21, 3001-12 (2012).
101. Crawley, J. N., Heyer, W. D. & LaSalle, J. M. Autism and Cancer Share Risk Genes, Pathways, and Drug Targets. Trends Genet 32, 139-46 (2016).
102. McGowan, P. O. et al. Broad epigenetic signature of maternal care in the brain of adult rats. PLoS One 6, e14739 (2011).
103. Kostadinov, D. & Sanes, J. R. Protocadherin-dependent dendritic self-avoidance regulates neural connectivity and circuit function. eLife 4(2015).
104. Wray, N. R. et al. Genome-wide association study of major depressive disorder: new results, meta-analysis, and lessons learned. Mol Psychiatry 17, 36-48 (2012).
105. Wang, Y. J. et al. Association of galanin and major depressive disorder in the Chinese Han population. PLoS One 8, e64617 (2013).
106. Barde, S. et al. Alterations in the neuropeptide galanin system in major depressive disorder involve levels of transcripts, methylation, and peptide. Proc Natl Acad Sci USA 113, E8472-E8481 (2016).
107. Santini, E. et al. Mitochondrial Superoxide Contributes to Hippocampal Synaptic Dysfunction and Memory Deficits in Angelman Syndrome Model Mice. J Neurosci 35, 16213-20 (2015).
108. Pitale, P. M., Howse, W. & Gorbatyuk, M. Neuronatin Protein in Health and Disease. J Cell Physiol 232, 477-481 (2017).
109. Varrault, A. et al. Zac1 regulates an imprinted gene network critically involved in the control of embryonic growth. Dev Cell 11, 711-22 (2006).
110. Arima, T. et al. ZAC, LIT1 (KCNQ1OT1) and p57KIP2 (CDKN1C) are in an imprinted gene network that may play a role in Beckwith-Wiedemann syndrome. Nucleic Acids Res 33, 2650-60 (2005).
111. Gabory, A. et al. H19 acts as a trans regulator of the imprinted gene network controlling growth in mice. Development 136, 3413-21 (2009).
112. Pan, Z. et al. M3 subtype of muscarinic acetylcholine receptor promotes cardioprotection via the suppression of miR-376b-5p. PLoS One 7, e32571 (2012).
113. Korkmaz, G., le Sage, C., Tekirdag, K. A., Agami, R. & Gozuacik, D. miR-376b controls starvation and mTOR inhibition-related autophagy by targeting ATG4C and BECN1. Autophagy 8, 165-76 (2012).
114. Korosi, A. et al. Early-life experience reduces excitation to stress-responsive hypothalamic neurons and reprograms the expression of corticotropin-releasing hormone. J Neurosci 30, 703-13.
115. Myers, M. M., Brunelli, S. A., Shair, H. N., Squire, J. M. & Hofer, M. A. Relationships between maternal behavior of SHR and WKY dams and adult blood pressures of cross-fostered F1 pups. Dev Psychobiol 22, 55-67 (1989).
116. Popik, P., Vetulani, J. & van Ree, J. M. Low doses of oxytocin facilitate social recognition in rats. Psychopharmacology 106, 71-4 (1992).
117. Popik, P., Vos, P. E. & Van Ree, J. M. Neurohypophyseal hormone receptors in the septum are implicated in social recognition in the rat. Behavioural pharmacology 3, 351-358 (1992).
118. Palkovits, M. & Brownstein, M. J. Maps and guide to microdissection of the rat brain, 223 (Elsevier, New York, 1988).
119. Ashwell, K. W. S. & Paxinos, G. Atlas of the developing rat nervous system, 1 v. (various pagings) (Boston: Academic Press; imprint of Elsevier, Amsterdam New York, N.Y., 2008).
120. Braunschweig, D., Simcox, T., Samaco, R. C. & LaSalle, J. M. X-Chromosome inactivation ratios affect wild-type MeCP2 expression within mosaic Rett syndrome and Mecp2−/+ mouse brain. *Human Molecular Genetics* 13, 1275-86 (2004).
121. Nagarajan, R. P., Hogart, A. R., Gwye, Y., Martin, M. R. & Lasalle, J. M. Reduced MeCP2 expression is frequent in autism frontal cortex and correlates with aberrant MECP2 promoter methylation. Epigenetics 1, 172-182 (2006).
122. Burette, A. C. et al. Subcellular organization of UBE3A in neurons. J Comp Neurol 525, 233-251 (2017).
123. Mortazavi, A., Williams, B. A., McCue, K., Schaeffer, L. & Wold, B. Mapping and quantifying mammalian transcriptomes by RNA-Seq. Nat Methods 5, 621-8 (2008).
124. Sun, Z. et al. CAP-miRSeq: a comprehensive analysis pipeline for microRNA sequencing data. BMC Genomics 15, 423 (2014).

125. Ziller, M. J., Hansen, K. D., Meissner, A. & Aryee, M. J. Coverage recommendations for methylation analysis by whole-genome bisulfite sequencing. Nat Methods 12, 230-2, 1 p following 232 (2015).
126. Schroeder, D. I. et al. The human placenta methylome. Proceedings of the National Academy of Sciences of the United States of America 110, 6037-42 (2013).
127. Schroeder, D. I., Lott, P., Korf, I. & LaSalle, J. M. Large-scale methylation domains mark a functional subset of neuronally expressed genes. Genome Research 21, 1583-91 (2011).
128. Chen, P. Y., Cokus, S. J. & Pellegrini, M. BS Seeker: precise mapping for bisulfite sequencing. BMC Bioinformatics 11, 203 (2010).
129. Nagarajan, R. P., Hogart, A. R., Gwye, Y., Martin, M. R. & LaSalle, J. M. Reduced MeCP2 expression is frequent in autism frontal cortex and correlates with aberrant MECP2 promoter methylation. Epigenetics: official journal of the DNA Methylation Society 1, e1-11 (2006).
130. Thatcher, K. N. & LaSalle, J. M. Dynamic changes in Histone H3 lysine 9 acetylation localization patterns during neuronal maturation require MeCP2. Epigenetics: official journal of the DNA Methylation Society 1, 24-31 (2006).
131. Maezawa, I., Swanberg, S., Harvey, D., LaSalle, J. M. & Jin, L. W. Rett syndrome astrocytes are abnormal and spread MeCP2 deficiency through gap junctions. J Neurosci 29, 5051-61 (2009).
132. Swanberg, S. E., Nagarajan, R. P., Peddada, S., Yasui, D. H. & LaSalle, J. M. Reciprocal co-regulation of EGR2 and MECP2 is disrupted in Rett syndrome and autism. Hum Mol Genet 18, 525-34 (2009).
133. Powell, W. T. et al. R-loop formation at Snord116 mediates topotecan inhibition of Ube3a-antisense and allele-specific chromatin decondensation. Proceedings of the National Academy of Sciences of the United States of America 110, 13938-43 (2013).
134. Engelmann, M., Wotjak, C. T. & Landgraf, R. Social discrimination procedure: an alternative method to investigate juvenile recognition abilities in rats. Physiology & behavior 58, 315-21 (1995).
135. File, S. E. & Seth, P. A review of 25 years of the social interaction test. European journal of pharmacology 463, 35-53 (2003).
136. Barnes, C. A. Memory deficits associated with senescence: a neurophysiological and behavioral study in the rat. Journal of comparative and physiological psychology 93, 74-104 (1979).
137. Lee, D. J. et al. Medial septal nucleus theta frequency deep brain stimulation improves spatial working memory after traumatic brain injury. Journal of neurotrauma 30, 131-9 (2013).
138. Castagne, V., Moser, P., Roux, S. & Porsolt, R. D. Rodent models of depression: forced swim and tail suspension behavioral despair tests in rats and mice. Current protocols in neuroscience/editorial board, Jacqueline N. Crawley . . . [et al.] Chapter 8, Unit 8 10A (2011).
139. Vogel Ciernia, A. et al. Early motor phenotype detection in a female mouse model of Rett syndrome is improved by cross-fostering. Hum Mol Genet (2017).
140. Matsuura, T. et al. De novo truncating mutations in E6-AP ubiquitin-protein ligase gene (UBE3A) in Angelman syndrome. Nat Genet 15, 74-7 (1997).
141. Kishino, T., Lalande, M. & Wagstaff, J. UBE3A/E6-AP mutations cause Angelman syndrome. Nat Genet 15, 70-3 (1997).
142. Zykovich, A., Korf, I. & Segal, D. J. Bind-n-Seq: high-throughput analysis of in vitro protein-DNA interactions using massively parallel sequencing. Nucleic Acids Res 37, e151 (2009).

We claim:

1. A transgenic rat whose genome comprises a homozygous deletion of its endogenous E3 ubiquitin ligase (Ube3a) gene, wherein the transgenic rat does not express Ube3a and exhibits physiological and/or behavioral features associated with Angelman Syndrome.

2. The transgenic rat of claim 1, wherein the genome of the transgenic rat has a further genetic modification.

3. A cell, tissue, or organ isolated from the transgenic rat of claim 1, wherein the cell's genome lacks the Ube3a gene or the tissue or the organ comprises one or more cells having a genome lacking the E3 ubiquitin ligase Ube3a gene.

4. A method for assessing the effect of an agent on a transgenic rat model, comprising exposing the transgenic rat of claim 1, or an isolated cell, tissue, or organ thereof, to the agent; and determining an effect of the agent on the transgenic rat model, cell, tissue, or organ.

5. The method of claim 4, wherein the agent comprises a small molecule, polypeptide, or nucleic acid.

6. The method of claim 4, wherein the agent comprises a combination of two or more agents, wherein the rat is exposed to the combination of agents simultaneously or consecutively.

7. The method of claim 4, wherein said exposing comprises administering the agent to the transgenic rat by a route selected from the group consisting of intravascular, intravenous, intra-arterial, intracranial, intrathecal, epidural, intraperitoneal, intramuscular, intracutaneous, oral, intragastric via gavage, intranasal, intratracheal, inhalational, intra-ocular, intrathoracic, intracardiac, topical, rectal, subcutaneous, intradermal, and transdermal.

8. The method of claim 4, wherein the transgenic rat ingests the agent.

9. The method of claim 4, wherein said determining comprises determining the effect of the agent on one or more physiological and/or behavioral parameters associated with Angelman Syndrome selected from behavioral impairment in ultrasonic vocalizations (USV), impaired gait comprising changes in paw angle, leg width, front and rear leg swing and combinations thereof.

10. The method of claim 9, wherein the one or more parameters further comprises one or more from among seizure, motor coordination, learning, memory, and synaptic function.

\* \* \* \* \*